US007713737B2

(12) United States Patent
Mrsny

(10) Patent No.: US 7,713,737 B2
(45) Date of Patent: May 11, 2010

(54) METHODS AND COMPOSITIONS FOR NEEDLELESS DELIVERY OF MACROMOLECULES

(75) Inventor: Randall J. Mrsny, Los Altos Hills, CA (US)

(73) Assignee: Trinity Biosystems, Inc., Menlo Park, CA (US)

(*) Notice: Subject to any disclaimer, the term of this patent is extended or adjusted under 35 U.S.C. 154(b) by 65 days.

(21) Appl. No.: 11/244,349

(22) Filed: Oct. 4, 2005

(65) Prior Publication Data

US 2006/0153798 A1 Jul. 13, 2006

Related U.S. Application Data

(60) Provisional application No. 60/615,970, filed on Oct. 4, 2004, provisional application No. 60/684,484, filed on May 24, 2005, provisional application No. 60/718,907, filed on Sep. 19, 2005.

(51) Int. Cl.
| | |
|---|---|
| *C12N 5/00* | (2006.01) |
| *C12N 15/00* | (2006.01) |
| *C12P 21/06* | (2006.01) |
| *C07H 21/04* | (2006.01) |
| *C07K 14/00* | (2006.01) |
| *C07K 16/00* | (2006.01) |
| *C12P 21/08* | (2006.01) |
| *A61K 38/24* | (2006.01) |

(52) U.S. Cl. .................. 435/325; 435/320.1; 435/69.1; 536/23.4; 530/351; 530/387.1; 530/388.1; 530/388.2; 530/399

(58) Field of Classification Search ....................... None
See application file for complete search history.

(56) References Cited

U.S. PATENT DOCUMENTS

| | | | | |
|---|---|---|---|---|
| 5,328,984 | A * | 7/1994 | Pastan et al. | 424/134.1 |
| 5,541,287 | A | 7/1996 | Yau et al. | |
| 6,022,966 | A | 2/2000 | Gustavson et al. | |
| 6,072,041 | A | 6/2000 | Davis et al. | |
| 6,086,900 | A * | 7/2000 | Draper | 424/282.1 |
| 2003/0054012 | A1 | 3/2003 | Fitzgerald et al. | |
| 2004/0001801 | A1 | 1/2004 | Madison et al. | |
| 2004/0071731 | A1 | 4/2004 | Fitzgerald | |
| 2004/0228831 | A1 * | 11/2004 | Belinka et al. | 424/78.27 |
| 2005/0079171 | A1 | 4/2005 | FitzGerald et al. | |
| 2006/0104993 | A1 | 5/2006 | Mrsny | |
| 2006/0110409 | A1 * | 5/2006 | Shone et al. | 424/239.1 |
| 2007/0003578 | A1 | 1/2007 | Fitzgerald | |
| 2007/0141070 | A1 | 6/2007 | Mrsny | |
| 2007/0148131 | A1 | 6/2007 | Mrsny | |

FOREIGN PATENT DOCUMENTS

| | | | |
|---|---|---|---|
| WO | WO86/06635 | | 11/1986 |
| WO | WO95/07297 | | 3/1995 |
| WO | WO98/20135 | | 5/1998 |
| WO | WO98/42876 | | 10/1998 |
| WO | WO 98/42876 | * | 10/1998 |
| WO | WO00/46246 | | 8/2000 |
| WO | WO01/30392 | | 5/2001 |
| WO | WO01/31020 | | 5/2001 |

OTHER PUBLICATIONS

Backer et al. 2002. Bioconjugate Chem. 13:462-467.* www.cancerweb.ncl.ac.uk/cgi-bin/omd?elastase, Nov. 18, 1997, downloaded Sep. 10, 2007.* www.cancerweb.ncl.ac.uk/cgi-bin/omd?leukocyte+elastase Dec. 12, 1998, downloaded Sep. 10, 2007.*

Gray et al. 1984. PNAS 81:2645-2649.*
Mayer et al. 2003. J. Cell Sci. 116:1763-1773.*
Pirila et al. 2001, BBRC 287:766-774.*
Mook et al 2003. Journal of Histochem and Cytochem.*
Moll et al. 1990. Cancer Res. 50:6995-7002.*
U.S. Appl. No. 09/462,682, filed Apr. 28, 2000, Fitzgerald.
U.S. Appl. No. 10/110,880, filed Apr. 16, 2002, Fitzgerald et al.
U.S. Appl. No. 11/664,786, filed Apr. 3, 2007, Mrsny.
U.S. Appl. No. 11/664,787, filed Apr. 3, 2007, Mrsny.
Andreasen, P.A. et al., "Receptor-mediated endocytosis of Plasminogen activators and activator/inhibitor complexes." FEBS Letters, vol. 338, No. 3; pp. 239-245 (1994).
Cavallaro, U. et al., "Targeting plant toxins to the urokinase and α-2-macroglobulin receptors." Semin Cancer Biol., vol. 6, No. 5; pp. 269-278 (1995).
Daugherty, A.L. et al., "Epithelial application of *Pseudomonas aeruginosa* exotoxin A results in a selective targeting to cells in the liver, spleen and lymph node." J. Controlled Release, vol. 65, Nos. 1-2; pp. 297-302 (2000).
Fitzgerald, D.J. et al., "Characterization of V3 loop-Pseudonomas exotoxin chimeras. Candidate vaccines for human immunodeficiency virus-1." J. Biol. Chem., vol. 273, No. 16; pp. 9951-9958 (1998).

(Continued)

*Primary Examiner*—Gary B Nickol
*Assistant Examiner*—Shulamith H Shafer
(74) *Attorney, Agent, or Firm*—Jones Day

(57) ABSTRACT

Methods and compositions for needleless delivery of macromolecules to the bloodstream of a subject are provided herein. In one aspect, the invention provides a delivery construct, comprising a receptor binding domain, a transcytosis domain, a macromolecule to be delivered to a subject, and a cleavable linker. In certain aspects, the cleavable linker can be cleavable by an enzyme present in higher concentration at or near the basal-lateral membrane of a polarized epithelial cell or in the plasma than elsewhere in the body, for example, at the apical side of the polarized epithelial cell. In other aspects, the invention provides nucleic acids encoding delivery constructs of the invention, kits comprising delivery constructs of the invention, cells expressing delivery constructs of the invention, and methods of using delivery constructs of the invention.

31 Claims, 23 Drawing Sheets

OTHER PUBLICATIONS

Figure 1B:
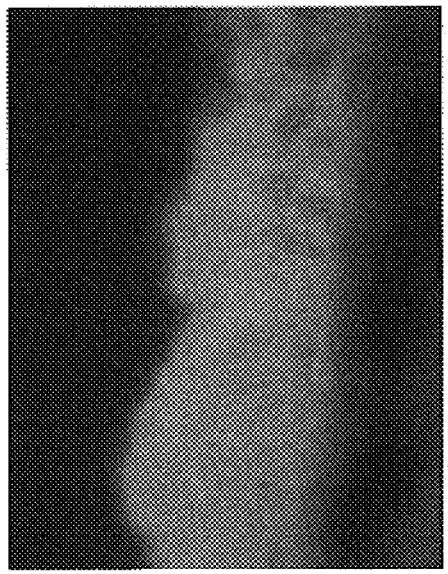

Herz J. and D.K. Strickland, "LRP: a multifunctional scavenger and signaling receptor." J Clin Invest, vol. 108, No. 6; pp. 779-784 (2001).

Maziere, J.C. et al., "Processing and characterization of the low density lipoprotein receptor in the human colonic carcinoma cell subclone HT29-18: a potential pathway for delivering therapeutic drugs and genes." Biosci. Rep., vol. 12, No. 6; pp. 483-494 (1992).

Melman, L. et al., "High affinity binding of receptor-associated protein to heparin and low density lipoprotein receptor-related protein requires similar basic amino acid sequence motifs." J. Biol. Chem., vol. 276, No. 31; pp. 29338-29446(2001).

Mrsny R.J. et al., "Mucosal administration of a chimera composed of pseudomonas exotoxin and the gp120 V3 loop sequence of HIV-1 induces both salivary and serum antibody responses." Vaccine, vol. 17, Nos. 11-12; pp. 1425-1433 (1999).

Versluis, A.J. et al., "Stable incorporation of a lipophilic daunorubicin prodrug into apolipoprotein E-exposing liposomes induces uptake of prodrug via low-density lipoprotein receptor in vivo." J. Pharmacol. Experiment Therap., vol. 289, No. 1; pp. 1-7 (1999).

Zdanovsky, A.G. et al., "Targeting pseudomonas and diphtheria toxins to the alpha-2-macroglobulin receptor via RAP-toxin and PAI-I-toxin fusions." Prot. Engin., vol. 8, No. Supple., pp. 123 (1995).

Herbert et al., 1996, "Augmentation by Eosinophils of Gelatinase Activity in the Airway Mucosa: Comparative Effects as a Putative Mediator of Epithelial Injury," British Journal of Pharmacology, vol. 117:667-674.

Mrsny et al., 2002, "Bacterial Toxins as Tools for Mucosal Vaccination," Therapeutic Focus, vol. 7(4):247-258.

Murdoch and McCormick, 1992, "Enhanced Degradation of Collagen Within Apical vs. Basal Wall of Ovulatory Ovine Follicle," Dept. Of Animal Science, Univ. of Wyoming, © the American Physiological Society, Follicular Collagen and Ovulation, E221-E225.

Ogata et al., 1990, "Processing of Pseudomonas Exotoxin by a Cellular Protease Results in the Generation of a 37,000-Da Toxin Fragment that is Translocated to the Cytosol," The Journal of Biological Chemistry, vol. 265(33):20678-20685.

Siccardi et al., 2004, "Regulation of intestinal epithelial function: a link between opportunities for macromolecular drug delivery and inflammatory bowel disease," Advanced Drug Delivery Reviews, 57:219-235.

European Supplemental Search Report, dated Nov. 14, 2008, in European Application No. 05816333.8.

* cited by examiner

Figures 1A-D

Figure 3

*Pseudomonas Aeruginosa* Exotoxin A Amino Acid Sequence

Start of Domain I ↓
```
  1 mhliphwipl vaslgllagg ssasa aeeaf dlwnecakac vldlkdgvrs srmsvdpaia 61 dtngqgvlhy smvleggnda lklaidnals itsdgltirl eggvepnkpv rysytrqarg 121 swslnwlvpi ghekpsnikv fihelnagnq lshmspiyti emgdellakl ardatffvra 181 hesnemqptl aishagvsvv maqtqprrek rwsewasgkv lclldpldgv ynylaqqrcn
```

Start of Domain II ↓
```
241 lddtwegkiy rvlagnpakh dldikptvis hrlhfpeggs laaltahqac hlpletftrh
```

⇓Furin clip site
```
301 rqpr↱gweqle qcgypvqrlv alylaarlsw nqvdqvirna laspgsggdl geaireqpeq
```
Start of Domain III↓
```
361 arlaltlaaa eserfvrqgt gndeagaana dvvsltcpva agecagpads gdallernyp 421 tgaeflgdgg dvsfstrgtq nwtverllqa hrqleergyv fvgyhgtfle aaqsivfggv 481 rarsqdldai wrgfyiagdp alaygyaqdq epdargrirn gallrvyvpr sslpgfyrts 541 ltlaapeaag evErlighpl plrldaitgp eeeggrleti lgwplaertv vipsaiptdp 601 rnvggdldps sipdkeqais alpdyasqpg kppredlk
```

Figures 11A and 11B
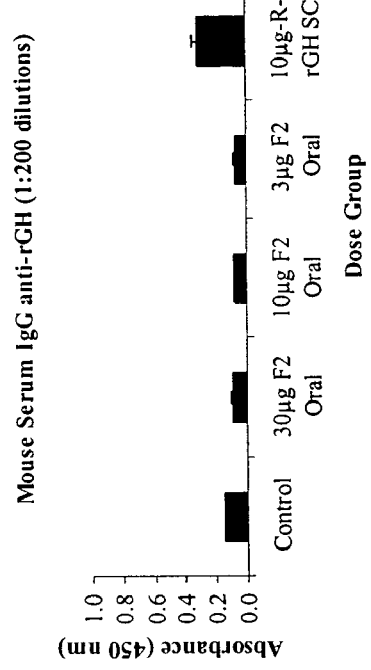
Figure 11A
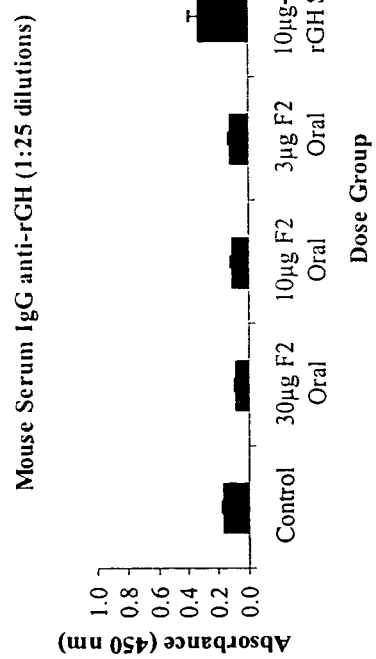
Figure 11B

Figures 11C and 11D
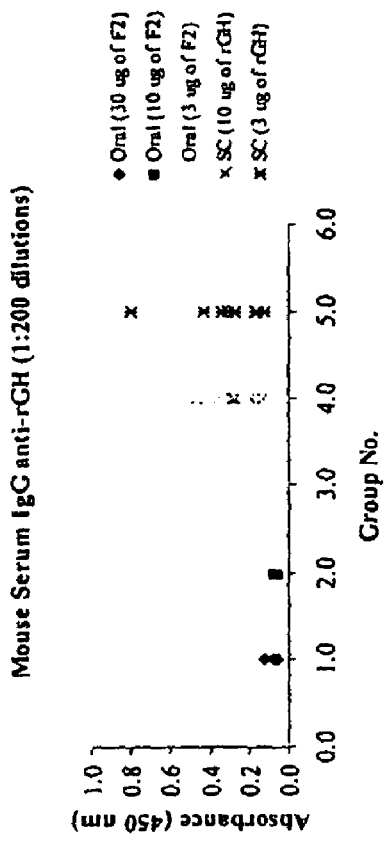
Figure 11D
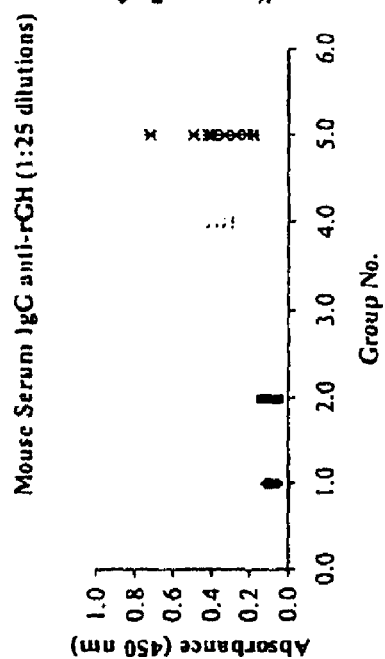
Figure 11C

Figure 12

```
atggccgaag aagctttcga cctctggaac gaatgcgcca aagcctgcgt gctcgacctc    60
aaggacggcg tgcgttccag ccgcatgagc gtcgacccgg ccatcgccga caccaacggc   120
cagggcgtgc tgcactactc catggtcctg gagggcggca acgacgcgct caagctggcc   180
atcgacaacg ccctcagcat caccagcgac ggcctgacca tccgcctcga aggcggcgtc   240
gagccgaaca agccggtgcg ctacagctac acgcgccagg cgcgcggcag ttggtcgctg   300
aactggctgg taccgatcgg ccacgagaag ccctcgaaca tcaaggtgtt catccacgaa   360
ctgaacgccg gcaaccagct cagccacatg tcgccgatct acaccatcga gatgggcgac   420
gagttgctgg cgaagctggc gcgcgatgcc accttcttcg tcagggcgca cgagagcaac   480
gagatgcagc cgacgctcgc catcagccat gccggggtca gcgtggtcat ggcccagacc   540
cagccgcgcc gggaaaagcg ctggagcgaa tgggccagcg gcaaggtgtt gtgcctgctc   600
gacccgctgg acggggtcta caactacctc gcccagcaac gctgcaacct cgacgatacc   660
tgggaaggca agatctaccg ggtgctcgcc ggcaacccgg cgaagcatga cctggacatc   720
aaacccacgg tcatcagtca tcgcctgcac tttcccgagg gcggcagcct ggccgcgctg   780
accgcgcacc aggcttgcca cctgccgctg gagactttca cccgtcatcg ccagccgcgc   840
ggctgggaac aactcgagca gtgcggctat ccggtgcagc ggctggtcgc cctctacctg   900
gcggcgcggc tgtcgtggaa ccaggtcgac caggtgatcc gcaacgccct ggccagcccc   960
ggcagcggcg gcgacctggg cgaagcgatc cgcgagcagc cggagcaggc ccgtctggcc  1020
ctgaccctgg ccgccgccga gagcgagcgc ttcgtccggc agggcaccgg caacgacgag  1080
gccggcgcgg caaacctgca gggaggatta cgccagcctc gattcccgac catcccgctg  1140
tcccgtctgt tcgacaacgc tatgctgcgt gctcaccgtc tgcaccagct ggctttcgac  1200
acctaccagg agttcgaaga agcatacatc ccgaagaac agaaatactc cttcctgcaa  1260
aacccgcaga cctccctgtg cttctccgaa tcgatcccga ccccgtccaa ccgtgaagaa  1320
acccagcaga atccaacct ggagctcctg cgtatctccc tgctgctgat ccagtcctgg  1380
ctcgagccgg ttcagttcct gcgttccgtt tcgctaact ccctggttta cggtgctagc  1440
gactccaacg tttacgacct gctgaaagac ctggaagaag gtatccagac cctgatgggt  1500
cgtctggaag acggttcccc gcgtaccggt cagatcttca aacagaccta ctccaaattc  1560
gacaccaact cccacaacga cgacgctctg ctgaaaaact acggtctgct gtactgcttc  1620
cgtaaagaca tggacaaagt tgaaaccttc ctgcgtatcg ttcagtgccg ttccgttgaa  1680
ggttcctgcg gtttctaa                                                1698
```

Figure 13A

```
Met Ala Glu Glu Ala Phe Asp Leu Trp Asn Glu Cys Ala Lys Ala Cys
 1            5                    10                  15
Val Leu Asp Leu Lys Asp Gly Val Arg Ser Ser Arg Met Ser Val Asp
           20                  25                  30
Pro Ala Ile Ala Asp Thr Asn Gly Gln Gly Val Leu His Tyr Ser Met
           35                  40                  45
Val Leu Glu Gly Gly Asn Asp Ala Leu Lys Leu Ala Ile Asp Asn Ala
     50                  55                  60
Leu Ser Ile Thr Ser Asp Gly Leu Thr Ile Arg Leu Glu Gly Gly Val
65                  70                  75                  80
Glu Pro Asn Lys Pro Val Arg Tyr Ser Tyr Thr Arg Gln Ala Arg Gly
               85                  90                  95
Ser Trp Ser Leu Asn Trp Leu Val Pro Ile Gly His Glu Lys Pro Ser
               100                 105                 110
Asn Ile Lys Val Phe Ile His Glu Leu Asn Ala Gly Asn Gln Leu Ser
           115                 120                 125
His Met Ser Pro Ile Tyr Thr Ile Glu Met Gly Asp Glu Leu Leu Ala
     130                 135                 140
Lys Leu Ala Arg Asp Ala Thr Phe Phe Val Arg Ala His Glu Ser Asn
145                 150                 155                 160
Glu Met Gln Pro Thr Leu Ala Ile Ser His Ala Gly Val Ser Val Val
               165                 170                 175
Met Ala Gln Thr Gln Pro Arg Arg Glu Lys Arg Trp Ser Glu Trp Ala
               180                 185                 190
Ser Gly Lys Val Leu Cys Leu Leu Asp Pro Leu Asp Gly Val Tyr Asn
           195                 200                 205
Tyr Leu Ala Gln Gln Arg Cys Asn Leu Asp Asp Thr Trp Glu Gly Lys
     210                 215                 220
Ile Tyr Arg Val Leu Ala Gly Asn Pro Ala Lys His Asp Leu Asp Ile
225                 230                 235                 240
Lys Pro Thr Val Ile Ser His Arg Leu His Phe Pro Glu Gly Gly Ser
               245                 250                 255
Leu Ala Ala Leu Thr Ala His Gln Ala Cys His Leu Pro Leu Glu Thr
               260                 265                 270
Phe Thr Arg His Arg Gln Pro Arg Gly Trp Glu Gln Leu Glu Gln Cys
           275                 280                 285
Gly Tyr Pro Val Gln Arg Leu Val Ala Leu Tyr Leu Ala Ala Arg Leu
     290                 295                 300
Ser Trp Asn Gln Val Asp Gln Val Ile Arg Asn Ala Leu Ala Ser Pro
305                 310                 315                 320
Gly Ser Gly Gly Asp Leu Gly Glu Ala Ile Arg Glu Gln Pro Glu Gln
               325                 330                 335
Ala Arg Leu Ala Leu Thr Leu Ala Ala Glu Ser Glu Arg Phe Val
               340                 345                 350
Arg Gln Gly Thr Gly Asn Asp Glu Ala Gly Ala Ala Asn Leu Gln Gly
           355                 360                 365
Gly Leu Arg Gln Pro Arg Phe Pro Thr Ile Pro Leu Ser Arg Leu Phe
     370                 375                 380
```

Figure 13B

```
Asp Asn Ala Met Leu Arg Ala His Arg Leu His Gln Leu Ala Phe Asp
385             390             395             400
Thr Tyr Gln Glu Phe Glu Glu Ala Tyr Ile Pro Lys Glu Gln Lys Tyr
                405             410             415
Ser Phe Leu Gln Asn Pro Gln Thr Ser Leu Cys Phe Ser Glu Ser Ile
            420             425             430
Pro Thr Pro Ser Asn Arg Glu Glu Thr Gln Gln Lys Ser Asn Leu Glu
        435             440             445
Leu Leu Arg Ile Ser Leu Leu Leu Ile Gln Ser Trp Leu Glu Pro Val
    450             455             460
Gln Phe Leu Arg Ser Val Phe Ala Asn Ser Leu Val Tyr Gly Ala Ser
465             470             475             480
Asp Ser Asn Val Tyr Asp Leu Leu Lys Asp Leu Glu Glu Gly Ile Gln
                485             490             495
Thr Leu Met Gly Arg Leu Glu Asp Gly Ser Pro Arg Thr Gly Gln Ile
            500             505             510
Phe Lys Gln Thr Tyr Ser Lys Phe Asp Thr Asn Ser His Asn Asp Asp
        515             520             525
Ala Leu Leu Lys Asn Tyr Gly Leu Leu Tyr Cys Phe Arg Lys Asp Met
    530             535             540
Asp Lys Val Glu Thr Phe Leu Arg Ile Val Gln Cys Arg Ser Val Glu
545             550             555             560
Gly Ser Cys Gly Phe
                565
```

Figure 14

```
atggccgaag aagctttcga cctctggaac gaatgcgcca aagcctgcgt gctcgacctc   60
aaggacggcg tgcgttccag ccgcatgagc gtcgacccgg ccatcgccga caccaacggc  120
cagggcgtgc tgcactactc catggtcctg gagggcggca acgacgcgct caagctggcc  180
atcgacaacg ccctcagcat caccagcgac ggcctgacca tccgcctcga aggcggcgtc  240
gagccgaaca agccggtgcg ctacagctac acgcgccagg cgcgcggcag ttggtcgctg  300
aactggctgg taccgatcgg ccacgagaag ccctcgaaca tcaaggtgtt catccacgaa  360
ctgaacgccg gcaaccagct cagccacatg tcgccgatct acaccatcga gatgggcgac  420
gagttgctgg cgaagctggc gcgcgatgcc accttcttcg tcagggcgca cgagagcaac  480
gagatgcagc cgacgctcgc catcagccat gccggggtca gcgtggtcat ggcccagacc  540
cagccgcgcc gggaaaagcg ctggagcgaa tgggccagcg gcaaggtgtt gtgcctgctc  600
gacccgctgg acggggtcta caactacctc gcccagcaac gctgcaacct cgacgatacc  660
tgggaaggca agatctaccg ggtgctcgcc ggcaacccgg cgaagcatga cctggacatc  720
aaacccacgg tcatcagtca tcgcctgcac tttcccgagg cggcagcct  ggccgcgctg  780
accgcgcacc aggcttgcca cctgccgctg gagactttca cccgtcatcg ccagccgcgc  840
ggctgggaac aactcgagca gtgcggctat ccggtgcagc ggctggtcgc cctctacctg  900
gcggcgcggc tgtcgtggaa ccaggtcgac caggtgatcc gcaacgccct ggccagcccc  960
ggcagcggcg gcgacctggg cgaagcgatc cgcgagcagc cggagcaggc cgtctggcc  1020
ctgaccctgg ccgccgccga gagcgagcgc ttcgtccggc agggcaccgg caacgacgag 1080
gccggcgcgg caaacctgca ggaggcttac gccagcctc  gatgcgatct gcctcagacc 1140
cacagcctgg gcagcaggag gaccctgatg ctgctggctc agatgaggag aatcagcctg 1200
tttagctgcc tgaaggatag gcacgatttt ggctttcctc aagaggagtt tggcaaccag 1260
tttcagaagg ctgagaccat ccctgtgctg cacgagatga tccagcagat ctttaacctg 1320
tttagcacca aggatagcag cgctgcttgg gatgagaccc tgctggataa gttttacacc 1380
gagctgtacc agcagctgaa cgatctggag gcttgcgtga tccagggcgt gggcgtgacc 1440
gagacccctc tgatgaagga ggatagcatc ctggctgtga ggaagtactt tcagaggatc 1500
accctgtacc tgaaggagaa gaagtacagc ccctgcgctt gggaagtcgt gagggctgag 1560
atcatgagga gctttagcct gagcaccaac ctgcaagaga gcttgaggtc taaggagtaa 1620
```

Figure 15A

```
Met Ala Glu Glu Ala Phe Asp Leu Trp Asn Glu Cys Ala Lys Ala Cys
 1           5                   10                  15
Val Leu Asp Leu Lys Asp Gly Val Arg Ser Ser Arg Met Ser Val Asp
            20                  25                  30
Pro Ala Ile Ala Asp Thr Asn Gly Gln Gly Val Leu His Tyr Ser Met
            35                  40                  45
Val Leu Glu Gly Gly Asn Asp Ala Leu Lys Leu Ala Ile Asp Asn Ala
 50                      55                  60
Leu Ser Ile Thr Ser Asp Gly Leu Thr Ile Arg Leu Glu Gly Gly Val
 65              70                  75                      80
Glu Pro Asn Lys Pro Val Arg Tyr Ser Tyr Thr Arg Gln Ala Arg Gly
                85                  90                  95
Ser Trp Ser Leu Asn Trp Leu Val Pro Ile Gly His Glu Lys Pro Ser
                100                 105                 110
Asn Ile Lys Val Phe Ile His Glu Leu Asn Ala Gly Asn Gln Leu Ser
            115                 120                 125
His Met Ser Pro Ile Tyr Thr Ile Glu Met Gly Asp Glu Leu Leu Ala
            130                 135                 140
Lys Leu Ala Arg Asp Ala Thr Phe Phe Val Arg Ala His Glu Ser Asn
145                 150                 155                 160
Glu Met Gln Pro Thr Leu Ala Ile Ser His Ala Gly Val Ser Val Val
                165                 170                 175
Met Ala Gln Thr Gln Pro Arg Arg Glu Lys Arg Trp Ser Glu Trp Ala
            180                 185                 190
Ser Gly Lys Val Leu Cys Leu Leu Asp Pro Leu Asp Gly Val Tyr Asn
            195                 200                 205
Tyr Leu Ala Gln Gln Arg Cys Asn Leu Asp Asp Thr Trp Glu Gly Lys
    210                 215                 220
Ile Tyr Arg Val Leu Ala Gly Asn Pro Ala Lys His Asp Leu Asp Ile
225                 230                 235                 240
Lys Pro Thr Val Ile Ser His Arg Leu His Phe Pro Glu Gly Gly Ser
                245                 250                 255
Leu Ala Ala Leu Thr Ala His Gln Ala Cys His Leu Pro Leu Glu Thr
            260                 265                 270
Phe Thr Arg His Arg Gln Pro Arg Gly Trp Glu Gln Leu Glu Gln Cys
            275                 280                 285
Gly Tyr Pro Val Gln Arg Leu Val Ala Leu Tyr Leu Ala Ala Arg Leu
    290                 295                 300
Ser Trp Asn Gln Val Asp Gln Val Ile Arg Asn Ala Leu Ala Ser Pro
305                 310                 315                 320
Gly Ser Gly Gly Asp Leu Gly Glu Ala Ile Arg Glu Gln Pro Glu Gln
                325                 330                 335
Ala Arg Leu Ala Leu Thr Leu Ala Ala Glu Ser Glu Arg Phe Val
            340                 345                 350
Arg Gln Gly Thr Gly Asn Asp Glu Ala Gly Ala Ala Asn Leu Gln Gly
            355                 360                 365
Gly Leu Arg Gln Pro Arg Cys Asp Leu Pro Gln Thr His Ser Leu Gly
    370                 375                 380
```

Figure 15B

```
Ser Arg Arg Thr Leu Met Leu Leu Ala Gln Met Arg Arg Ile Ser Leu
385              390              395              400
Phe Ser Cys Leu Lys Asp Arg His Asp Phe Gly Phe Pro Gln Glu Glu
            405              410              415
Phe Gly Asn Gln Phe Gln Lys Ala Glu Thr Ile Pro Val Leu His Glu
        420              425              430
Met Ile Gln Gln Ile Phe Asn Leu Phe Ser Thr Lys Asp Ser Ser Ala
        435              440              445
Ala Trp Asp Glu Thr Leu Leu Asp Lys Phe Tyr Thr Glu Leu Tyr Gln
    450              455              460
Gln Leu Asn Asp Leu Glu Ala Cys Val Ile Gln Gly Val Gly Val Thr
465              470              475              480
Glu Thr Pro Leu Met Lys Glu Asp Ser Ile Leu Ala Val Arg Lys Tyr
            485              490              495
Phe Gln Arg Ile Thr Leu Tyr Leu Lys Glu Lys Lys Tyr Ser Pro Cys
        500              505              510
Ala Trp Glu Val Val Arg Ala Glu Ile Met Arg Ser Phe Ser Leu Ser
    515              520              525
Thr Asn Leu Gln Glu Ser Leu Arg Ser Lys Glu
530              535
```

Figure 17A

```
Met Ala Glu Glu Ala Phe Asp Leu Trp Asn Glu Cys Ala Lys Ala Cys
1               5                   10                  15
Val Leu Asp Leu Lys Asp Gly Val Arg Ser Ser Arg Met Ser Val Asp
                20                  25                  30
Pro Ala Ile Ala Asp Thr Asn Gly Gln Gly Val Leu His Tyr Ser Met
                35                  40                  45
Val Leu Glu Gly Gly Asn Asp Ala Leu Lys Leu Ala Ile Asp Asn Ala
        50                  55                  60
Leu Ser Ile Thr Ser Asp Gly Leu Thr Ile Arg Leu Glu Gly Gly Val
65                  70                  75                  80
Glu Pro Asn Lys Pro Val Arg Tyr Ser Tyr Thr Arg Gln Ala Arg Gly
                85                  90                  95
Ser Trp Ser Leu Asn Trp Leu Val Pro Ile Gly His Glu Lys Pro Ser
                100                 105                 110
Asn Ile Lys Val Phe Ile His Glu Leu Asn Ala Gly Asn Gln Leu Ser
        115                 120                 125
His Met Ser Pro Ile Tyr Thr Ile Glu Met Gly Asp Glu Leu Leu Ala
    130                 135                 140
Lys Leu Ala Arg Asp Ala Thr Phe Phe Val Arg Ala His Glu Ser Asn
145                 150                 155                 160
Glu Met Gln Pro Thr Leu Ala Ile Ser His Ala Gly Val Ser Val Val
                165                 170                 175
Met Ala Gln Thr Gln Pro Arg Arg Glu Lys Arg Trp Ser Glu Trp Ala
                180                 185                 190
Ser Gly Lys Val Leu Cys Leu Leu Asp Pro Leu Asp Gly Val Tyr Asn
        195                 200                 205
Tyr Leu Ala Gln Gln Arg Cys Asn Leu Asp Asp Thr Trp Glu Gly Lys
    210                 215                 220
Ile Tyr Arg Val Leu Ala Gly Asn Pro Ala Lys His Asp Leu Asp Ile
225                 230                 235                 240
Lys Pro Thr Val Ile Ser His Arg Leu His Phe Pro Glu Gly Gly Ser
                245                 250                 255
Leu Ala Ala Leu Thr Ala His Gln Ala Cys His Leu Pro Leu Glu Thr
                260                 265                 270
Phe Thr Arg His Arg Gln Pro Arg Gly Trp Glu Gln Leu Glu Gln Cys
        275                 280                 285
Gly Tyr Pro Val Gln Arg Leu Val Ala Leu Tyr Leu Ala Ala Arg Leu
    290                 295                 300
Ser Trp Asn Gln Val Asp Gln Val Ile Arg Asn Ala Leu Ala Ser Pro
305                 310                 315                 320
Gly Ser Gly Gly Asp Leu Gly Glu Ala Ile Arg Glu Gln Pro Glu Gln
                325                 330                 335
Ala Arg Leu Ala Leu Thr Leu Ala Ala Glu Ser Glu Arg Phe Val
                340                 345                 350
Arg Gln Gly Thr Gly Asn Asp Glu Ala Gly Ala Ala Asn Leu Gln Gly
        355                 360                 365
Gly Leu Arg Gln Pro Arg Phe Val Asn Gln His Leu Cys Gly Ser His
    370                 375                 380
```

Figure 17B

```
Leu Val Glu Ala Leu Tyr Leu Val Cys Gly Glu Arg Gly Phe Phe Tyr
385             390             395                     400
Thr Pro Lys Thr Arg Arg Glu Ala Glu Asp Leu Gln Val Gly Gln Val
            405             410              415
Glu Leu Gly Gly Gly Pro Gly Ala Gly Ser Leu Gln Pro Leu Ala Leu
            420             425              430
Glu Gly Ser Leu Gln Lys Arg Gly Ile Val Glu Gln Cys Cys Thr Ser
        435             440             445
Ile Cys Ser Leu Tyr Gln Leu Glu Asn Tyr Cys Asn
    450             455             460
```

Figure 18A

| | | | | | | | | | | | | | | |
|---|---|---|---|---|---|---|---|---|---|---|---|---|---|---|
|Met|Ala|Glu|Glu|Ala|Phe|Asp|Leu|Trp|Asn|Glu|Cys|Ala|Lys|Ala|Cys|
|1| | |5| | | | |10| | | | |15| |
|Val|Leu|Asp|Leu|Lys|Asp|Gly|Val|Arg|Ser|Ser|Arg|Met|Ser|Val|Asp|
| | | |20| | | | |25| | | | |30| |
|Pro|Ala|Ile|Ala|Asp|Thr|Asn|Gly|Gln|Gly|Val|Leu|His|Tyr|Ser|Met|
| | | |35| | | | |40| | | | |45| |
|Val|Leu|Glu|Gly|Gly|Asn|Asp|Ala|Leu|Lys|Leu|Ala|Ile|Asp|Asn|Ala|
| | | |50| | | | |55| | | | |60| |
|Leu|Ser|Ile|Thr|Ser|Asp|Gly|Leu|Thr|Ile|Arg|Leu|Glu|Gly|Gly|Val|
|65| | | | |70| | | | |75| | | | |80|
|Glu|Pro|Asn|Lys|Pro|Val|Arg|Tyr|Ser|Tyr|Thr|Arg|Gln|Ala|Arg|Gly|
| | | | |85| | | | |90| | | | |95| |
|Ser|Trp|Ser|Leu|Asn|Trp|Leu|Val|Pro|Ile|Gly|His|Glu|Lys|Pro|Ser|
| | | |100| | | | |105| | | | |110| |
|Asn|Ile|Lys|Val|Phe|Ile|His|Glu|Leu|Asn|Ala|Gly|Asn|Gln|Leu|Ser|
| | |115| | | | |120| | | | |125| | |
|His|Met|Ser|Pro|Ile|Tyr|Thr|Ile|Glu|Met|Gly|Asp|Glu|Leu|Leu|Ala|
| |130| | | | |135| | | | |140| | | |
|Lys|Leu|Ala|Arg|Asp|Ala|Thr|Phe|Phe|Val|Arg|Ala|His|Glu|Ser|Asn|
|145| | | | |150| | | | |155| | | | |160|
|Glu|Met|Gln|Pro|Thr|Leu|Ala|Ile|Ser|His|Ala|Gly|Val|Ser|Val|Val|
| | | | |165| | | | |170| | | | |175| |
|Met|Ala|Gln|Thr|Gln|Pro|Arg|Arg|Glu|Lys|Arg|Trp|Ser|Glu|Trp|Ala|
| | | |180| | | | |185| | | | |190| | |
|Ser|Gly|Lys|Val|Leu|Cys|Leu|Leu|Asp|Pro|Leu|Asp|Gly|Val|Tyr|Asn|
| | |195| | | | |200| | | | |205| | | |
|Tyr|Leu|Ala|Gln|Gln|Arg|Cys|Asn|Leu|Asp|Asp|Thr|Trp|Glu|Gly|Lys|
| |210| | | | |215| | | | |220| | | | |
|Ile|Tyr|Arg|Val|Leu|Ala|Gly|Asn|Pro|Ala|Lys|His|Asp|Leu|Asp|Ile|
|225| | | | |230| | | | |235| | | | |240|
|Lys|Pro|Thr|Val|Ile|Ser|His|Arg|Leu|His|Phe|Pro|Glu|Gly|Gly|Ser|
| | | | |245| | | | |250| | | | |255| |
|Leu|Ala|Ala|Leu|Thr|Ala|His|Gln|Ala|Cys|His|Leu|Pro|Leu|Glu|Thr|
| | | |260| | | | |265| | | | |270| | |
|Phe|Thr|Arg|His|Arg|Gln|Pro|Arg|Gly|Trp|Glu|Gln|Leu|Glu|Gln|Cys|
| | |275| | | | |280| | | | |285| | | |
|Gly|Tyr|Pro|Val|Gln|Arg|Leu|Val|Ala|Leu|Tyr|Leu|Ala|Ala|Arg|Leu|
| |290| | | | |295| | | | |300| | | | |
|Ser|Trp|Asn|Gln|Val|Asp|Gln|Val|Ile|Arg|Asn|Ala|Leu|Ala|Ser|Pro|
|305| | | | |310| | | | |315| | | | |320|
|Gly|Ser|Gly|Gly|Asp|Leu|Gly|Glu|Ala|Ile|Arg|Glu|Gln|Pro|Glu|Gln|
| | | | |325| | | | |330| | | | |335| |
|Ala|Arg|Leu|Ala|Leu|Thr|Leu|Ala|Ala|Glu|Ser|Glu|Arg|Phe|Val|
| | | |340| | | | |345| | | | |350| | |
|Arg|Gln|Gly|Thr|Gly|Asn|Asp|Glu|Ala|Gly|Ala|Ala|Asn|Leu|Gln|Gly|
| | |355| | | | |360| | | | |365| | | |
|Gly|Leu|Arg|Gln|Pro|Arg|Phe|Val|Asn|Gln|His|Leu|Cys|Gly|Ser|His|
| |370| | | | |375| | | | |380| | | | |
|Leu|Val|Glu|Ala|Leu|Tyr|Leu|Val|Cys|Gly|Glu|Arg|Gly|Phe|Phe|Tyr|
|385| | | | |390| | | | |395| | | | |400|
|Thr|Pro|Lys|Thr| | | | | | | | | | | | |

Figure 18B

```
Gly Ile Val Glu Gln Cys Cys Thr Ser Ile Cys Ser Leu Tyr Gln
Leu
 1               5                  10                  15
Glu Asn Tyr Cys Asn
            20
```

METHODS AND COMPOSITIONS FOR NEEDLELESS DELIVERY OF MACROMOLECULES

This application is entitled to and claims benefit of U.S. Provisional Application No. 60/615,970, filed Oct. 4, 2004, of U.S. Provisional Application No. 60/684,484, filed May 24, 2005, and of U.S. Provisional Application No. 60/718,907, filed Sep. 19, 2005, each of which is hereby incorporated by reference in its entirety.

1. FIELD OF THE INVENTION

The present invention relates, in part, to methods and compositions for needleless delivery of macromolecules to a subject. In one aspect, the methods and compositions involve administering to the subject a delivery construct comprising the macromolecule to be delivered, wherein the macromolecule is linked to the remainder of the construct with a linker that is cleavable at a basal-lateral membrane of a polarized epithelial cell.

2. BACKGROUND

Advances in biochemistry and molecular biology have resulted identification and characterization of many therapeutic macromolecules, including, for example, growth hormone, erythropoietin, insulin, IGF, and the like. Administration of these molecules can result in drastic improvements in quality of life for subjects afflict with a wide range of ailments.

However, administration of these therapeutic macromolecules remains problematic. Currently, therapeutic macromolecules are typically administered by injection. Such injections require penetration of the subject's skin and tissues and are associated with pain. Further, penetration of the skin breaches one effective nonspecific mechanism of protection against infection, and thus can lead to potentially serious infection.

Previous attempts have been made for needleless delivery of macromolecules to subjects. See, e.g., International Patent Publication No. WO 01/30,392. In these efforts, delivery vehicles are used to deliver macromolecules to a subject through polarized epithelial cells. However, these derivatives lack a cleavable linker that is cleavable by an enzyme at the basal-lateral membrane of a polarized epithelial cell. Without cleavage, the probability of induction of an immune response against the delivery vehicle and/or the macromolecule to be delivered is increased. Also, steric hindrance between the delivery vehicle and the macromolecule can reduce the activity of the macromolecule, reducing efficacy of the treatment.

Accordingly, there is an unmet need for new methods and compositions that can be used to administer macromolecules to subjects without breaching the skin of the subject. This and other needs are met by the methods and compositions of the present invention.

3. SUMMARY OF THE INVENTION

The delivery constructs of the invention comprise a macromolecule for delivery to a subject that is linked to the remainder of the construct with a cleavable linker. The linker is cleavable by an enzyme or an environmental cue that is present at the basal-lateral membrane of an epithelial cell.

Accordingly, in certain aspects, the invention provides a delivery construct comprising a receptor binding domain, a transcytosis domain, a macromolecule to be delivered to a subject, and a cleavable linker. Cleavage at the cleavable linker can separate the macromolecule from the remainder of the delivery construct. In certain embodiments, the cleavable linker can be cleavable by an enzyme that is present at a basal-lateral membrane of a polarized epithelial cell of the subject. In other embodiments, the cleavable linker can be cleavable by an enzyme that is present in the plasma of said subject.

In another aspect, the invention provides a polynucleotide that encodes a delivery construct comprising a receptor binding domain, a transcytosis domain, a macromolecule to be delivered to a subject, and a cleavable linker. Cleavage at the cleavable linker can separate the macromolecule from the remainder of the delivery construct. In certain embodiments, the cleavable linker can be cleavable by an enzyme that is present at a basal-lateral membrane of a polarized epithelial cell of the subject. In other embodiments, the cleavable linker can be cleavable by an enzyme that is present in the plasma of said subject.

In other embodiments, the polynucleotide that encodes a delivery construct comprises a nucleic acid sequence encoding a receptor binding domain, a nucleic acid sequence encoding a transcytosis domain, a nucleic acid sequence encoding a cleavable linker, and a nucleic acid sequence comprising a polylinker insertion site. The polylinker insertion site can be oriented relative to the nucleic acid sequence encoding a cleavable linker to allow to cleavage of the cleavable linker to separate a macromolecule that is encoded by a nucleic acid inserted into the polylinker insertion site from the remainder of the encoded delivery construct. In certain embodiments, the cleavable linker can be cleavable by an enzyme that is present at a basal-lateral membrane of a polarized epithelial cell of the subject. In other embodiments, the cleavable linker can be cleavable by an enzyme that is present in the plasma of said subject.

In another aspect, the invention provides an expression vector comprising a polynucleotide of the invention.

In still another aspect, the invention provides a cell comprising an expression vector of the invention.

In yet another aspect, the invention provides a composition comprising a delivery construct of the invention. In certain embodiments, the composition is a pharmaceutical composition.

In still another aspect, the invention provides a method for delivering a macromolecule to a subject. The method comprises contacting an apical surface of a polarized epithelial cell of the subject with a delivery construct of the invention. The delivery construct can comprise a receptor binding domain, a transcytosis domain, a cleavable linker, and the macromolecule to be delivered. The transcytosis domain can transcytose the macromolecule to and through the basal-lateral membrane of the epithelial cell. In certain embodiments, the cleavable linker can be cleaved by an enzyme that is present at a basal-lateral membrane of a polarized epithelial cell of the subject. In other embodiments, the cleavable linker can be cleavable by an enzyme that is present in the plasma of the subject. Cleavage at the cleavable linker can separate the macromolecule from the remainder of the delivery construct, and can deliver the macromolecule to the subject free from the remainder of the construct.

4. BRIEF DESCRIPTION OF THE DRAWINGS

FIGS. 1A-1D present micrographs showing adhesion to and transport across mouse tracheal epithelium of an exemplary delivery construct comprising green fluorescent protein (GFP) (Panels A-C), while GFP alone does not adhere to the epithelial cells (Panel D).

Figure 2:
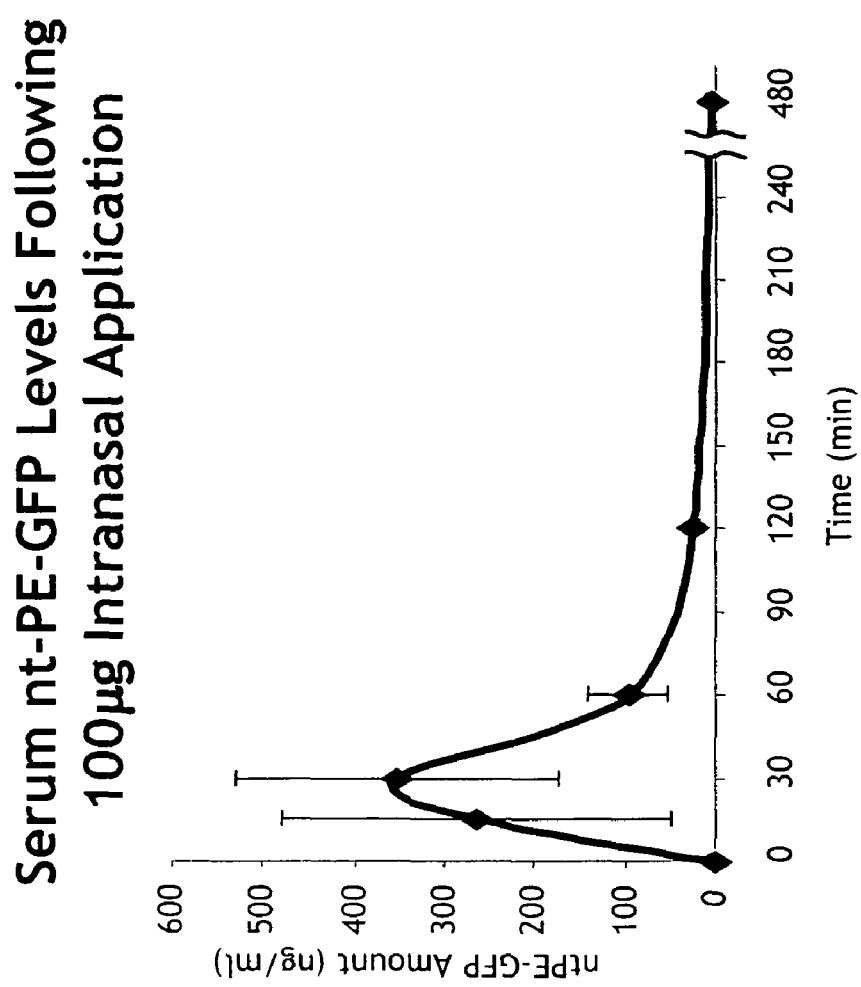

FIG. 2 presents a time course of serum nt-PE-GFP concentrations following intranasal administration of 100 µg nt-PE-GFP to anesthetized mice.

FIG. 3 presents the amino acid sequence of an exemplary PE (SEQ ID NO:41).

Figure 4:
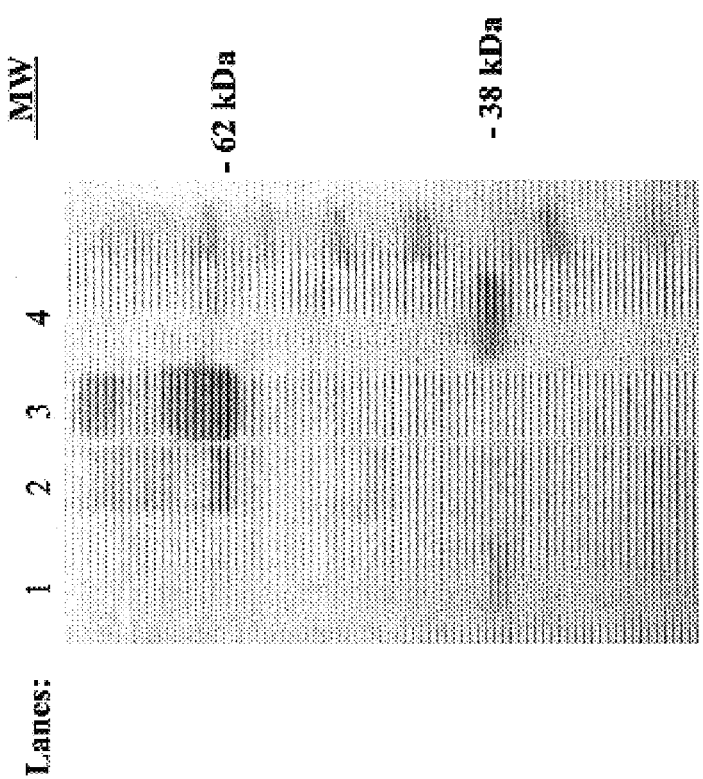

FIG. 4 presents a western blot showing transport and cleavage of an exemplary delivery construct comprising rat growth hormone (rGH) by human intestinal epithelial cell monolayers. The delivery construct was incubated in contact with the apical side of the epithelial cell monolayer for 4 hours. Media isolated from the basolateral side of the membrane post-incubation (lane 1) contained rGH of native apparent molecular weight, while media from the apical side of the membrane (lane 2) contained intact delivery construct. Lanes 3 and 4 show intact Delivery Construct 2 and recombinant rGH, respectively.

Figure 5:
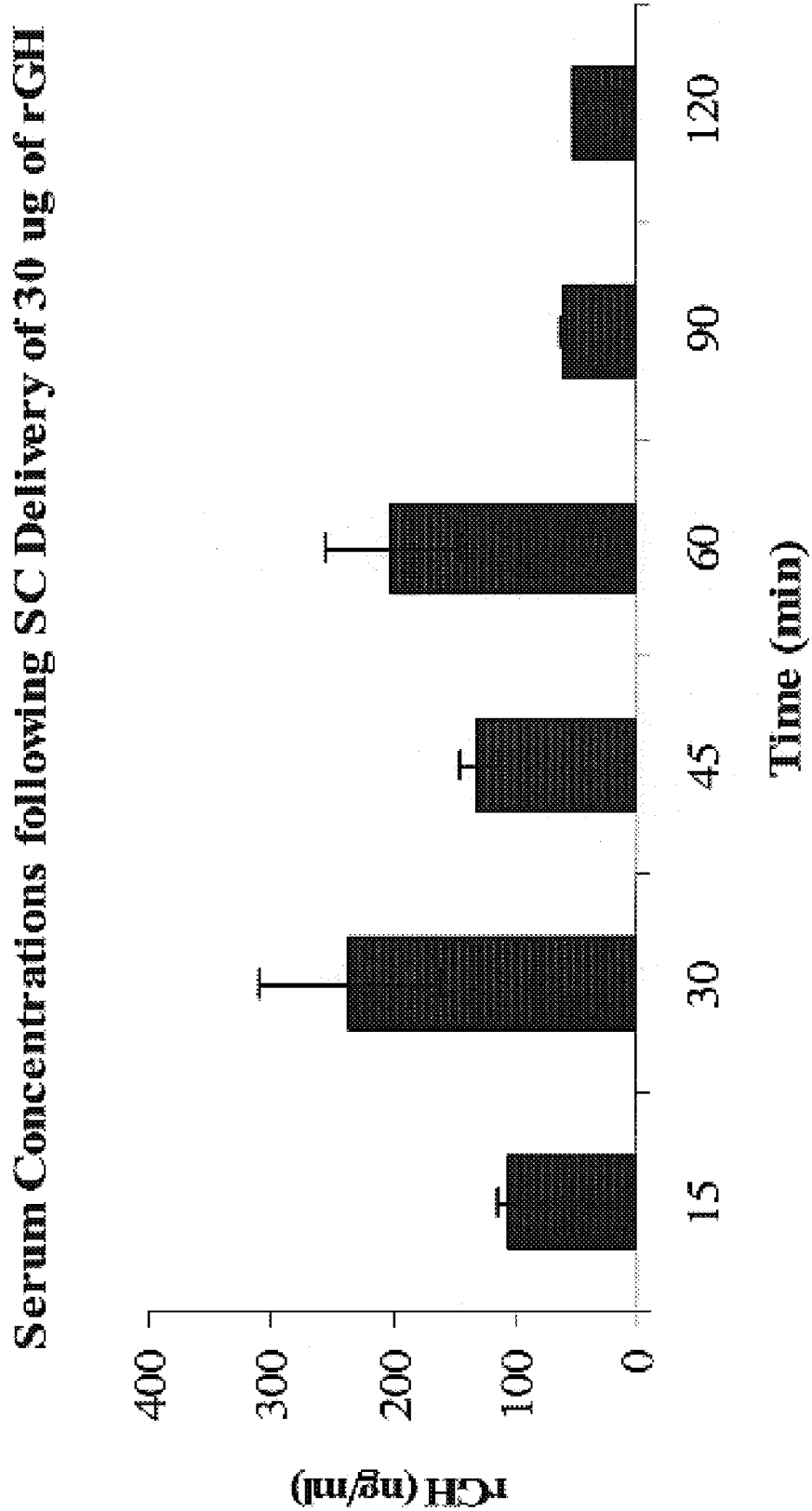

FIG. 5 presents serum rGH concentrations in BALB/c mice which were dosed by subcutaneous (SC) injection of 30 µg of non-glycosylated recombinant rat GH. Individual mice sera were tested at a dilution of 1:10, and the group average of rGH concentration were reported (n=4 mice per time point). Standard error of the mean (SEM) was indicated by the error bars.

Figure 6:
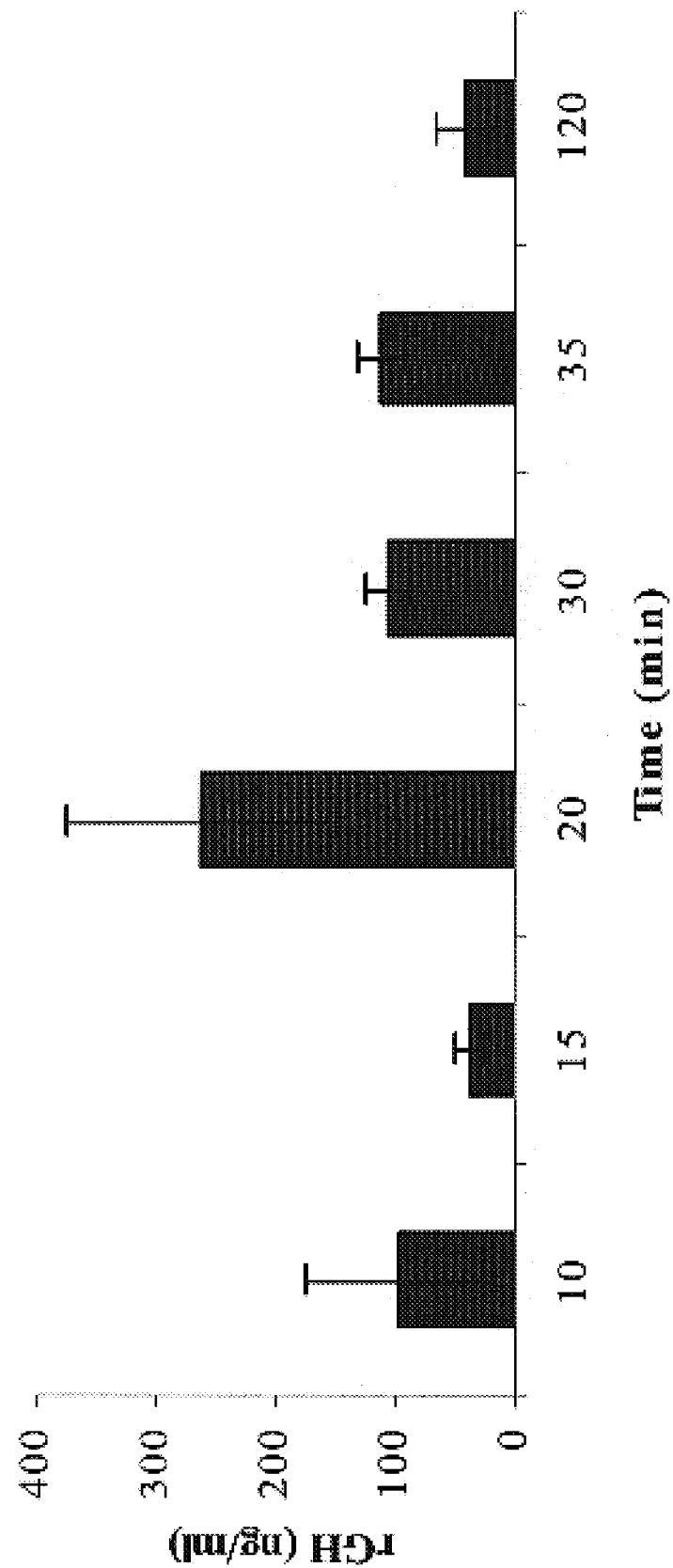

FIG. 6 presents serum rGH concentrations in BALB/c mice which were dosed orally with 100 µg of Delivery Construct 2. Individual mice sera were tested at a dilution of 1:10, and the group average of rGH concentration were reported (n=4 mice per time point). Standard error of the mean (SEM) was indicated by the error bars.

Figure 7:
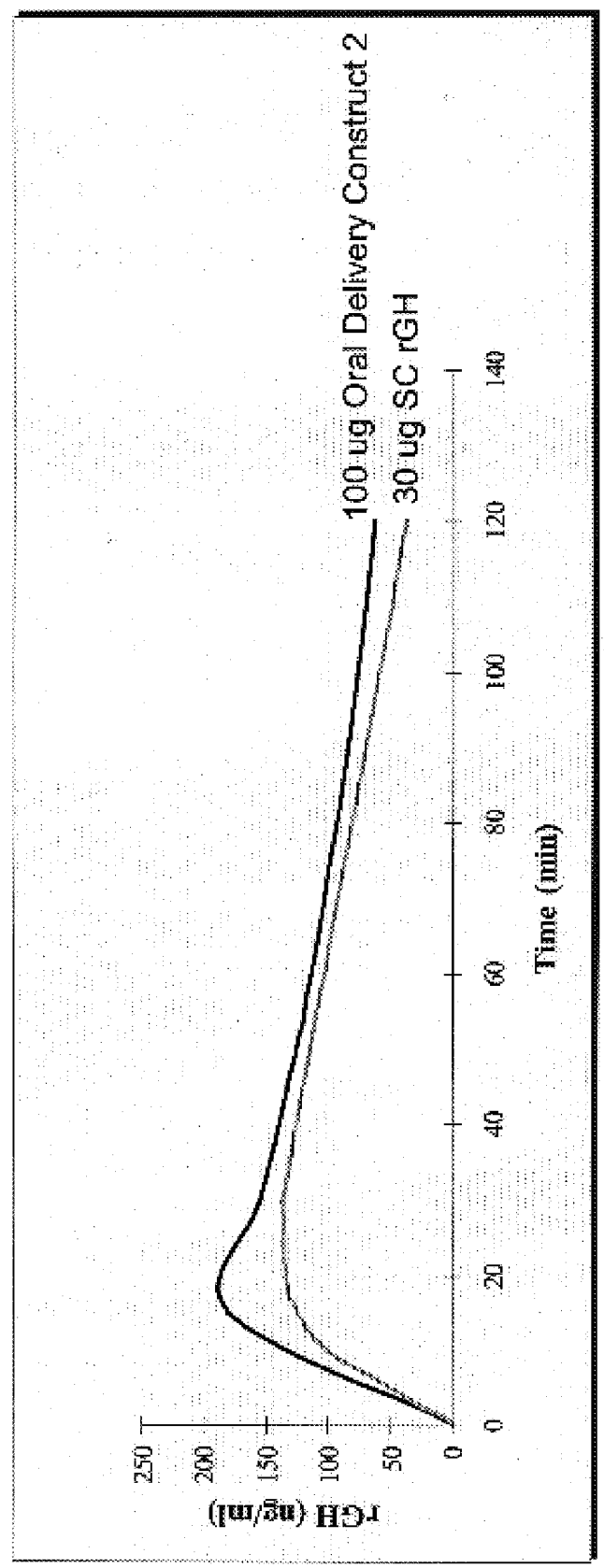

FIG. 7 presents a graphical representation comparing pharmacokinetics of rGH delivered subcutaneously and with Delivery Construct 2.

Figure 8:
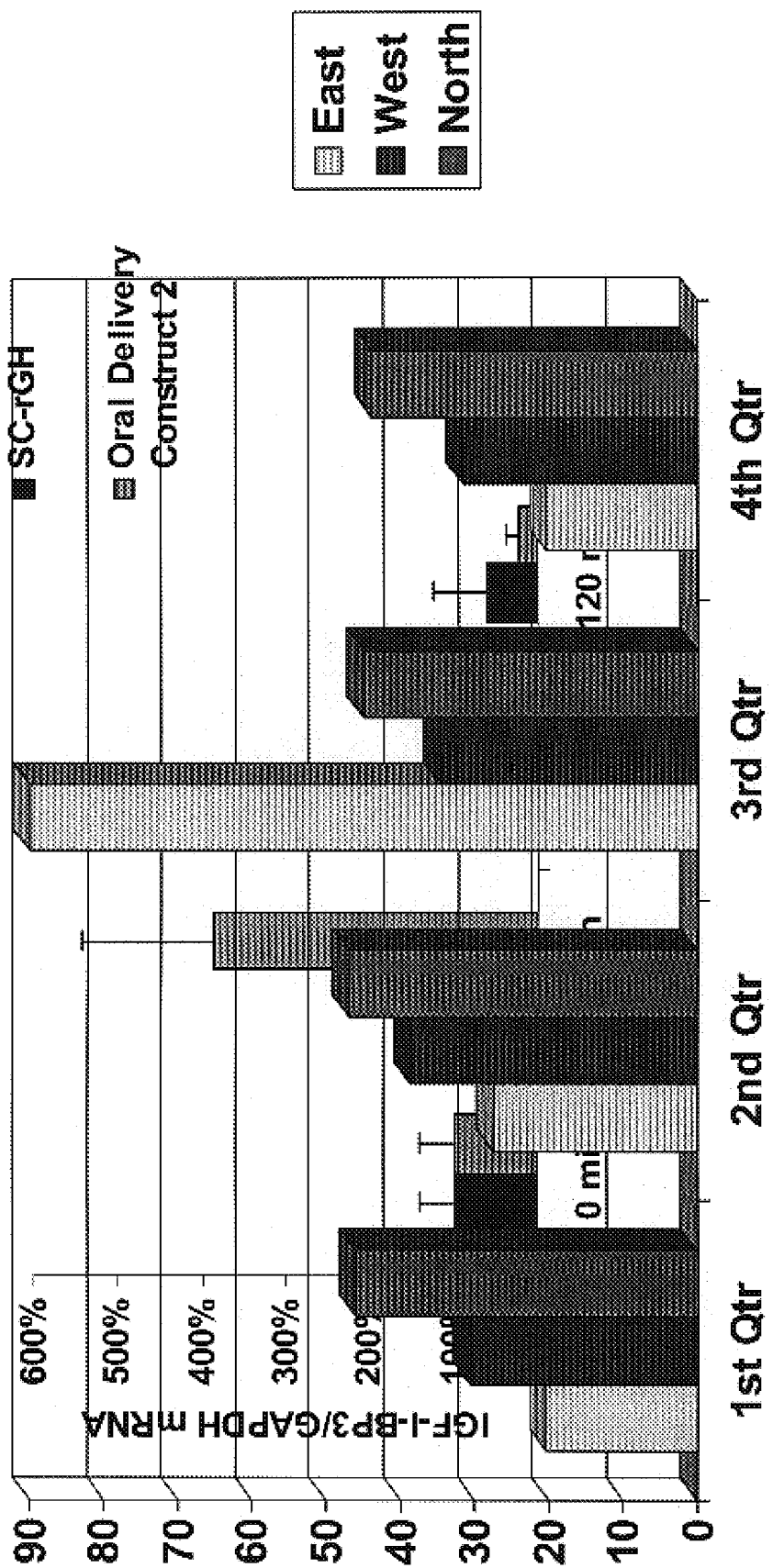

FIG. 8 shows expression levels of IGF-I-BP3 mRNA in the liver of female BALB/c mice treated with 30 µg recombinant rGH by subcutaneous injection or with 100 µg of Delivery Construct 2 by oral gavage. Total RNA extracted from the liver was subjected to quantitative RT-PCR using primers specific for IGF-I-BP3, as described above. Values were normalized to glyceraldehyde-3 phosphate dehydrogenase (GAPDH) and expressed as % of control.

Figure 9:
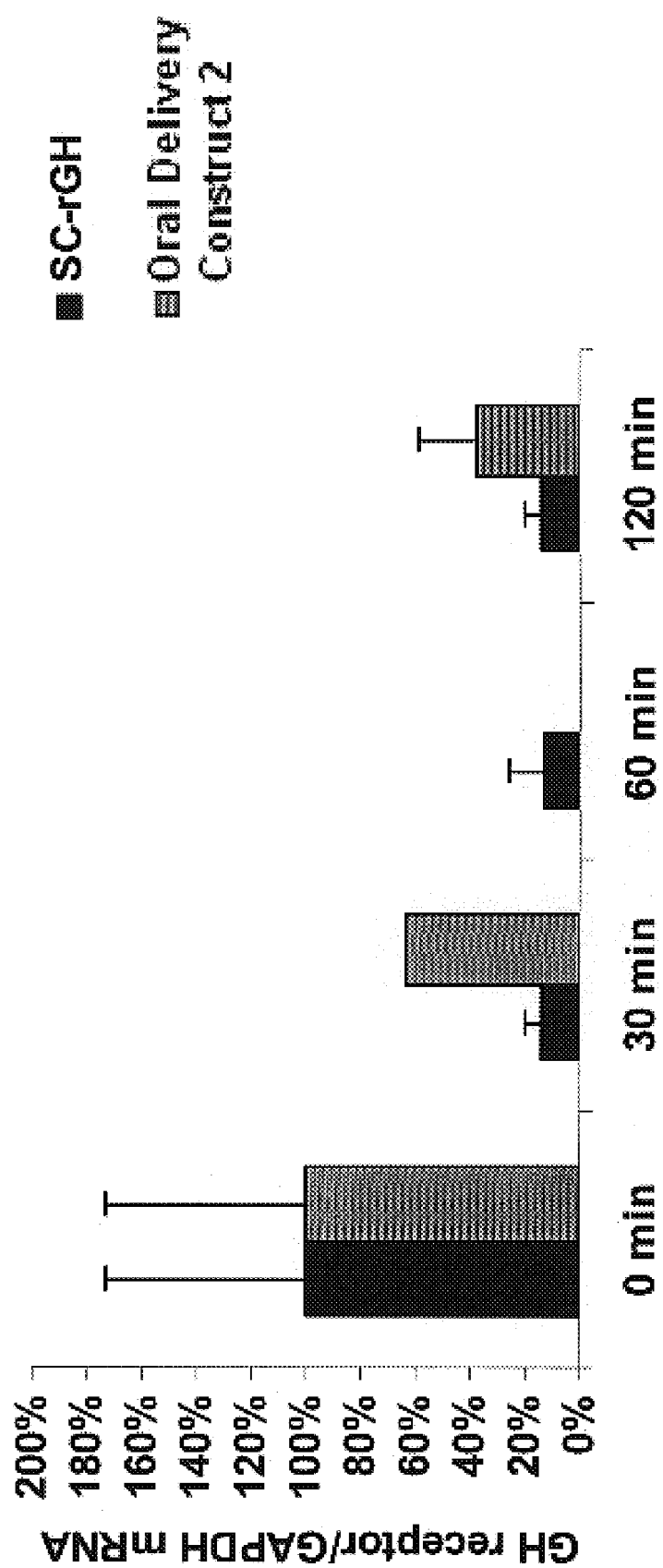

FIG. 9 shows expression levels of growth hormone (GH) receptor mRNA in the liver of female BALB/c mice treated with rGH by subcutaneous injection (30 µg) or Delivery Construct 2 by oral gavage (100 µg). Total RNA extracted from the liver was subjected to quantitative RT-PCR using primers specific for GH receptor, shown above. Values were normalized to glyceraldehyde-3 phosphate dehydrogenase (GAPDH) and expressed as % of control.

Figure 10:
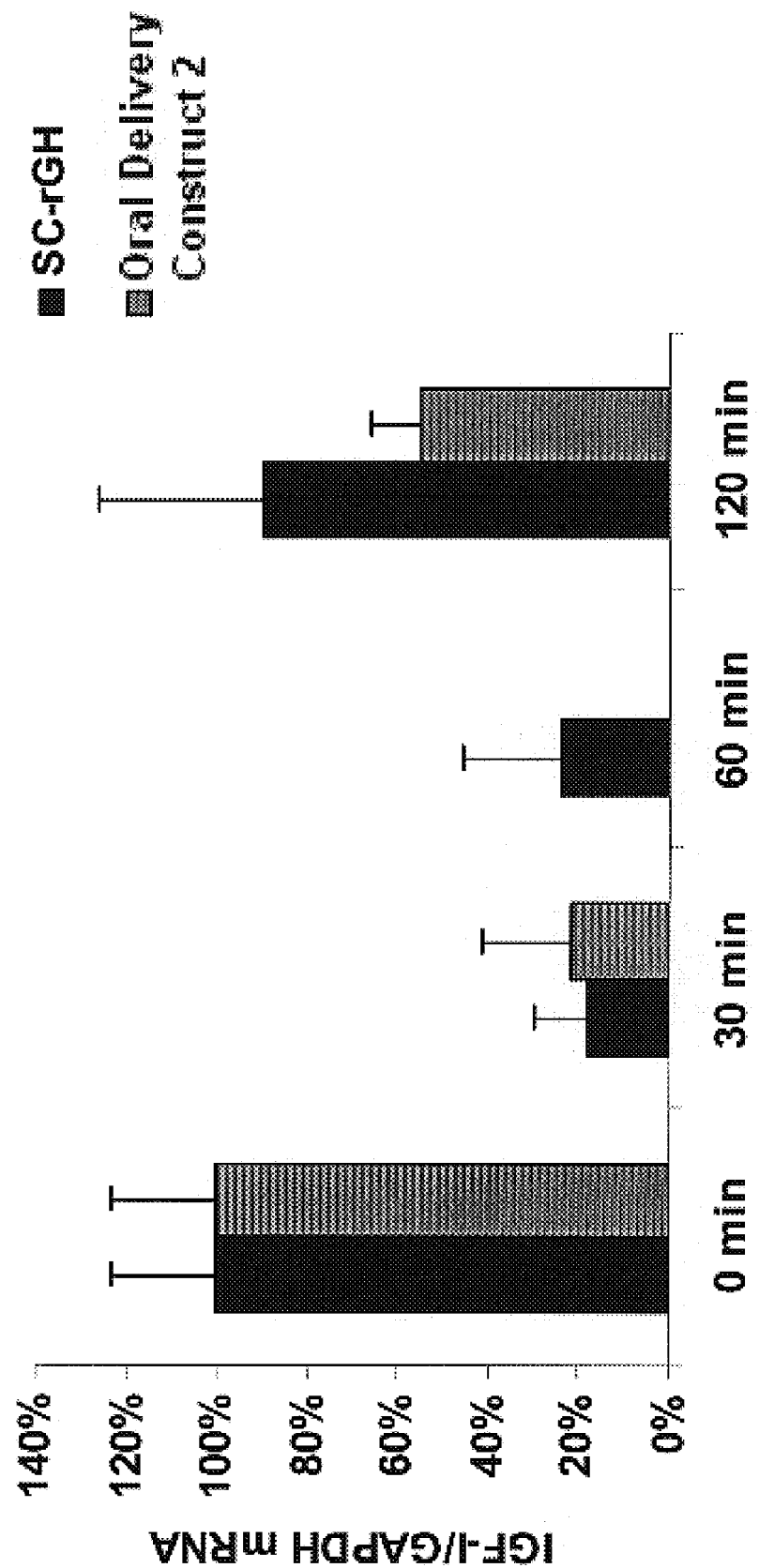

FIG. 10 shows expression levels of insulin-like growth factor I (IGF-I) mRNA in the liver of female BALB/c mice treated with rGH by subcutaneous injection (30 µg) or Delivery Construct 2 by oral gavage (100 µg). Total RNA extracted from the liver was subjected to quantitative RT-PCR using primers specific for IGF-I, shown above. Values were normalized to glyceraldehyde-3 phosphate dehydrogenase (GAPDH) and expressed as % of control.

FIGS. 11A and B show serum anti-rGH IgG antibodies (diluted 1:25 in FIG. 11A and 1:200 in FIG. 11B) of mice orally administered 3, 10, or 30 µg Delivery Construct 2 (F2) or subcutaneously administered 3 or 10 µg rGH in graphs with error bars, while FIGS. 11C and D presents the same data from individual animals.

FIG. 12 shows a nucleotide sequence that encodes Delivery Construct 6 (SEQ ID NO:34), an exemplary Delivery Construct for delivering human growth hormone (hGH).

FIGS. 13A and B show the amino acid sequence of Delivery Construct 6 (SEQ ID NO:35), an exemplary Delivery Construct for delivering hGH.

FIG. 14 shows a nucleotide sequence that encodes Delivery Construct 7 (SEQ ID NO:36), an exemplary Delivery Construct for delivering interferon-α (IFN-α).

FIGS. 15A and B show the amino acid sequence of Delivery Construct 7 (SEQ ID NO:37), an exemplary Delivery Construct for delivering IFN-α.

Figure 16:
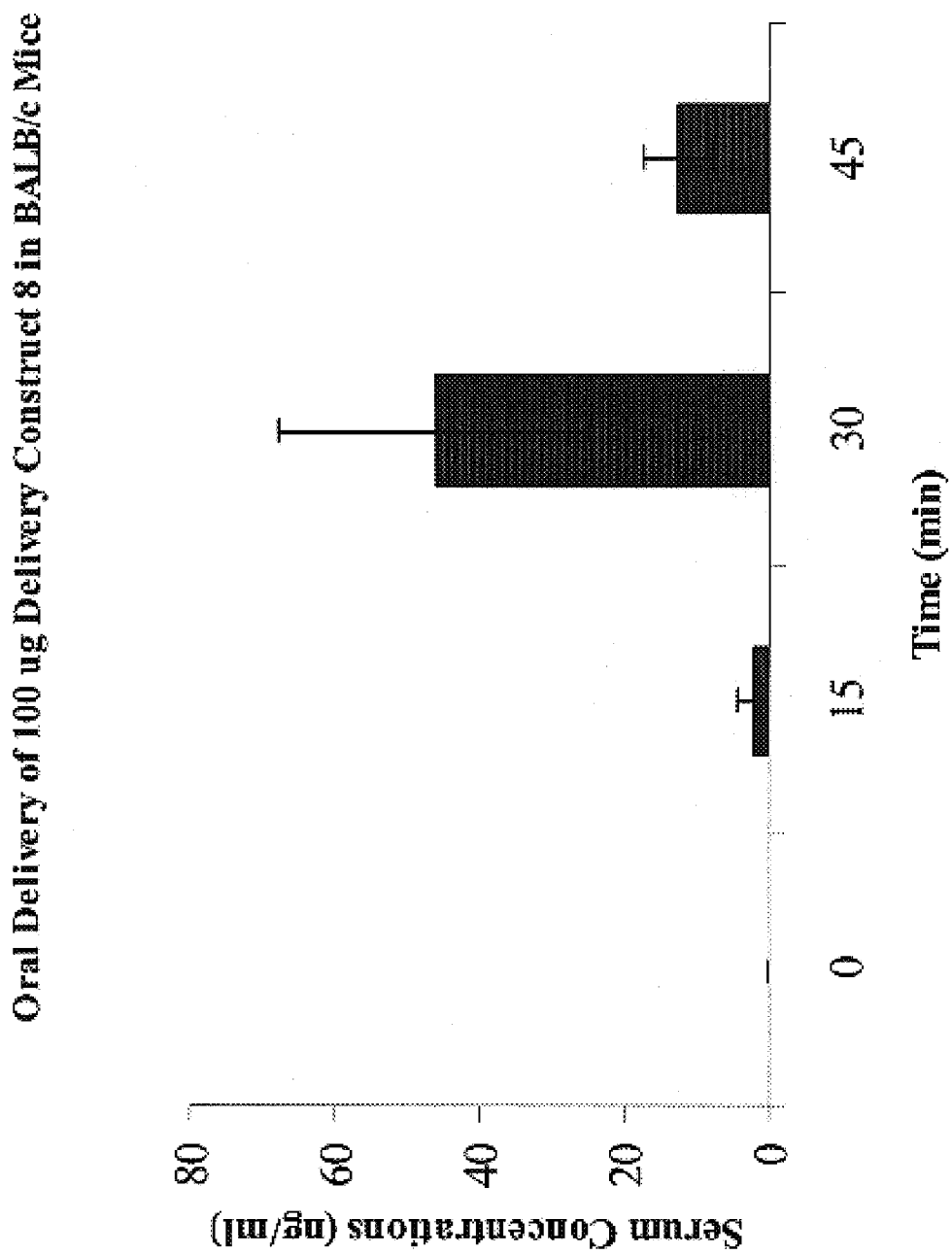

FIG. 16 shows 6 presents serum IFN-α concentrations in BALB/c mice which were dosed orally with 100 µg of Delivery Construct 8. Individual mice sera were tested at a dilution of 1:10, and the group average of IFN- a concentration were reported (n=3 mice per time point).

FIGS. 17A and B show the amino acid sequence of Delivery Construct 8 (SEQ ID NO:38), an exemplary Delivery Construct for delivering proinsulin.

FIGS. 18A and B shows the amino acid sequence of the two amino acid chains of Delivery Construct 9 (SEQ ID NOs:39 and 40, respectively), an exemplary Delivery Construct for delivering insulin. Disulfide bonds are formed between the cysteine at position 7 of SEQ ID NO:40 (shown in FIG. 18B) and the cysteine at position 381 of SEQ ID NO:39 (shown in FIG. 18A) and between the cysteine at position 20 of SEQ ID NO:40 and the cysteine at position 393 of SEQ ID NO:39.

5. DETAILED DESCRIPTION OF THE INVENTION

5.1. Definitions

Unless defined otherwise, all technical and scientific terms used herein have the meaning commonly understood by a person skilled in the art to which this invention belongs. As used herein, the following terms have the meanings ascribed to them unless specified otherwise.

A "ligand" is a compound that specifically binds to a target molecule. Exemplary ligands include, but are not limited to, an antibody, a cytokine, a substrate, a signaling molecule, and the like.

A "receptor" is compound that specifically binds to a ligand.

A ligand or a receptor (e.g., an antibody) "specifically binds to" or "is specifically immunoreactive with" another molecule when the ligand or receptor functions in a binding reaction that indicates the presence of the molecule in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to another polynucleotide comprising a complementary sequence and an antibody specifically binds under immunoassay conditions to an antigen bearing an epitope used to induce the antibody.

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. In one example, an antibody that binds a particular antigen with an affinity ($K_m$) of about 10 μM specifically binds the antigen.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc. when there is such a change in environment following transcytosis of the delivery construct across a polarized epithelial membrane.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 21st Ed. 2005, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enteral (e.g., oral, intranasal, rectal, or vaginal) or parenteral (e.g., subcutaneous, intramuscular, intravenous or intraperitoneal injection; or topical (e.g., transdermal, or transmucosal administration).

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis, treatment, or administration is a human or non-human animal, including a mammal or a primate, and preferably a human.

"Treatment" refers to prophylactic treatment or therapeutic treatment. A "prophylactic" treatment is a treatment administered to a subject who does not exhibit signs of a disease or exhibits only early signs for the purpose of decreasing the risk of developing pathology. A "therapeutic" treatment is a treatment administered to a subject who exhibits signs of pathology for the purpose of diminishing or eliminating those signs.

"Pseudomonas exotoxin A" or "PE" is secreted by Pseudomonas aeruginosa as a 67 kD protein composed of three prominent globular domains (Ia, II, and III) and one small subdomain (Ib) that connects domains II and III. See A. S. Allured et al., 1986, *Proc. Natl. Acad. Sci.* 83:1320-1324. Without intending to be bound to any particular theory or mechanism of action, domain Ia of PE is believed to mediate cell binding because domain Ia specifically binds to the low density lipoprotein receptor-related protein ("LRP"), also known as the α2-macroglobulin receptor ("α2-MR") and CD-91. See M. Z. Kounnas et al., 1992, *J. Biol. Chem.* 267: 12420-23. Domain Ia spans amino acids 1-252. Domain II of PE is believed to mediate transcytosis to the interior of a cell following binding of domain Ia to the α2-MR. Domain II spans amino acids 253-364. Certain portions of this domain may be required for secretion of PE from *Pseudomonas aeruginosa* after its synthesis. See, e.g., Vouloux et al., 2000, *J. Bacterol.* 182:4051-8. Domain Ib has no known function and spans amino acids 365-399. Domain III mediates cytotoxicity of PE and includes an endoplasmic reticulum retention sequence. PE cytotoxicity is believed to result from ADP ribosylation of elongation factor 2, which inactivates protein synthesis. Domain III spans amino acids 400-613 of PE. Deleting amino acid E553 ("ΔE553") from domain III eliminates EF2 ADP ribosylation activity and detoxifies PE. PE having the mutation ΔE553 is referred to herein as "PEΔE553." Genetically modified forms of PE are described in, e.g., U.S. Pat. Nos. 5,602,095; 5,512,658 and 5,458,878 *Pseudomonas* exotoxin, as used herein, also includes genetically modified, allelic, and chemically inactivated forms of PE within this definition. See, e.g., Vasil et al., 1986, *Infect. Immunol.* 52:538-48. Further, reference to the various domains of PE is made herein to the reference PE sequence presented as FIG. 3. However, one or more domain from modified PE, e.g., genetically or chemically modified PE, or a portion of such domains, can also be used in the chimeric immunogens of the invention so long as the domains retain functional activity. One of skill in the art can readily identify such domains of such modified PE based on, for example, homology to the PE sequence exemplified in FIG. 3 and test for functional activity using, for example, the assays described below.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the Gen-Bank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, J Mol. Biol. 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Amplification" refers to any means by which a polynucleotide sequence is copied and thus expanded into a larger number of polynucleotide molecules, e.g., by reverse transcription, polymerase chain reaction, ligase chain reaction, and the like.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology—Hybridization with Nucleic Acid Probes*, part I, chapter 2, "Overview of principles of hybridization and the strategy of nucleic acid probe assays", Elsevier, N.Y.; Sambrook et al., 2001, *Molecular Cloning: A Laboratory Manual*, Cold Spring Harbor Laboratory, 3$^{rd}$ ed., NY; and Ausubel et al., eds., Current Edition, *Current Protocols in Molecular Biology*, Greene Publishing Associates and Wiley Interscience, N.Y.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. Conventional notation is used herein to portray polypeptide sequences; the beginning of a polypeptide sequence is the amino-terminus, while the end of a polypeptide sequence is the carboxyl-terminus.

The term "protein" typically refers to large polypeptides, for example, polypeptides comprising more than about 50 amino acids. The term "protein" can also refer to dimers, trimers, and multimers that comprise more than one polypeptide.

"Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

5.2. Delivery Constructs

Generally, the delivery constructs of the present invention are polypeptides that have structural domains corresponding to domains Ia and II of PE. These structural domains perform certain functions, including, but not limited to, cell recognition and transcytosis, that correspond to the functions of the domains of PE.

In addition to the portions of the molecule that correspond to PE functional domains, the delivery constructs of this invention can further comprise a macromolecule for delivery to a biological compartment of a subject. The macromolecule can be introduced into any portion of the delivery construct that does not disrupt a cell-binding or transcytosis activity. The macromolecule is connected with the remainder of the delivery construct with a cleavable linker.

Accordingly, the delivery constructs of the invention generally comprise the following structural elements, each element imparting particular functions to the delivery construct: (1) a "receptor binding domain" that functions as a ligand for a cell surface receptor and that mediates binding of the construct to a cell; (2) a "transcytosis domain" that mediates transcytosis from a lumen bordering the apical surface of a mucous membrane to the basal-lateral side of a mucous membrane; (3) the macromolecule; and (4) a cleavable linker that connects the macromolecule to the remainder of the delivery construct.

The delivery constructs of the invention offer several advantages over conventional techniques for local or systemic delivery of macromolecules to a subject. Foremost among such advantages is the ability to deliver the macromolecule without using a needle to puncture the skin of the subject. Many subjects require repeated, regular doses of macromolecules. For example, diabetics must inject insulin several times per day to control blood sugar concentrations. Such subjects' quality of life would be greatly improved if the delivery of a macromolecule could be accomplished without injection, by avoiding pain or potential complications associated therewith.

Furthermore, many embodiments of the delivery constructs can be constructed and expressed in recombinant systems. Recombinant technology allows one to make a delivery construct having an insertion site designed for introduction of any suitable macromolecule. Such insertion sites allow the skilled artisan to quickly and easily produce delivery constructs for delivery of new macromolecules, should the need to do so arise.

In addition, connection of the macromolecule to the remainder of the delivery construct with a linker that is cleaved by an enzyme present at a basal-lateral membrane of an epithelial cell allows the macromolecule to be liberated from the delivery construct and released from the remainder of the delivery construct soon after transcytosis across the epithelial membrane. Such liberation reduces the probability of induction of an immune response against the macromolecule. It also allows the macromolecule to interact with its target free from the remainder of the delivery construct.

Other advantages of the delivery constructs of the invention will be apparent to those of skill in the art.

In certain embodiments, the invention provides a delivery construct that comprises a receptor binding domain, a transcytosis domain, a macromolecule to be delivered to a subject, and a cleavable linker. Cleavage at the cleavable linker separates the macromolecule from the remainder of the construct. The cleavable linker is cleavable by an enzyme that is present at a basal-lateral membrane of a polarized epithelial cell of the subject or in the plasma of the subject. In certain embodiments, the enzyme that is at a basal-lateral membrane of a polarized epithelial cell exhibits higher activity on the basal-lateral side of a polarized epithelial cell than it does on the apical side of the polarized epithelial cell. In certain embodiments, the enzyme that is in the plasma of the subject exhibits higher activity in the plasma than it does on the apical side of a polarized epithelial cell.

In certain embodiments, the delivery construct further comprises a second cleavable linker. In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10). In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10) and is cleavable by an enzyme that exhibits higher activity on the basal-lateral side of a polarized epithelial cell than it does on the apical side of the polarized epithelial cell. In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10) and is cleavable by an enzyme that exhibits higher activity in the plasma than it does on the apical side of a polarized epithelial cell.

In certain embodiments, the enzyme that is present at a basal-lateral membrane of a polarized epithelial cell is selected from the group consisting of Cathepsin GI, Chymotrypsin I, Elastase I, Subtilisin AI, Subtilisin AII, Thrombin I, and Urokinase I.

In certain embodiments, the receptor binding domain is selected from the group consisting of receptor binding domains from *Pseudomonas* exotoxin A, cholera toxin, botulinum toxin, diptheria toxin, shiga toxin, or shiga-like toxin; monoclonal antibodies; polyclonal antibodies; single-chain antibodies; TGFα; EGF; IGF-I; IGF-II; IGF-III; IL-1; IL-2; IL-3; IL-6; MIP-1a; MIP-1b; MCAF; and IL-8. In certain embodiments, the receptor binding domain binds to a cell-surface receptor that is selected from the group consisting of α2-macroglobulin receptor, epidermal growth factor receptor, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor. In further embodiments, the receptor binding domain of *Pseudomonas* exotoxin A is Domain Ia of *Pseudomonas* exotoxin A. In yet further embodiments, the receptor binding domain of *Pseudomonas* exotoxin A has an amino acid sequence that is SEQ ID NO.:1.

In certain embodiments, the transcytosis domain is selected from the group consisting of transcytosis domains from *Pseudomonas* exotoxin A, botulinum toxin, diptheria toxin, pertussis toxin, cholera toxin, heat-labile *E. coli* enterotoxin, shiga toxin, and shiga-like toxin. In further embodiments, the transcytosis domain is *Pseudomonas* exotoxin A transcytosis domain. In still further embodiments, the *Pseudomonas* exotoxin A transcytosis domain has an amino acid sequence that is SEQ ID NO.:2.

In certain embodiments, the macromolecule is selected from the group of a nucleic acid, a peptide, a polypeptide, a protein, and a lipid. In further embodiments, the polypeptide is selected from the group consisting of polypeptide hormones, cytokines, chemokines, growth factors, and clotting factors. In yet further embodiments, the polypeptide is selected from the group consisting of IGF-I, IGF-II, IGF-III, EGF, IFN-α, IFN-β, IFN-γ, G-CSF, GM-CSF, IL-1, IL-2, IL-3, IL-6, IL-8, IL-12, EPO, growth hormone, factor VII, vasopressin, calcitonin, parathyroid hormone, luteinizing hormone-releasing factor, tissue plasminogen activators, adrenocorticototropin, enkephalin, and glucagon-like peptide 1. In still further embodiments, the polypeptide is human growth hormone. In other embodiments, the protein is human insulin.

In certain embodiments, the delivery constructs further comprise a second macromolecule that is selected from the group consisting of a nucleic acid, a peptide, a polypeptide, a protein, a lipid, and a small organic molecule and a second cleavable linker, wherein cleavage at said second cleavable linker separates said second macromolecule from the remainder of said construct. In certain embodiments, the first macromolecule is a first polypeptide and said second macromolecule is a second polypeptide. In certain embodiments, the first polypeptide and the second polypeptide associate to form a multimer. In certain embodiments, the multimer is a dimer, tetramer, or octamer. In further embodiments, the dimer is an antibody.

5.2.1. Receptor Binding Domain

The delivery constructs of the invention generally comprise a receptor binding domain. The receptor binding domain can be any receptor binding domain known to one of skill in the art without limitation to bind to a cell surface receptor that is present on the apical membrane of an epithelial cell. Preferably, the receptor binding domain binds specifically to the cell surface receptor. The receptor binding domain should bind to the cell surface receptor with sufficient affinity to allow endocytosis of the delivery construct.

In certain embodiments, the receptor binding domain can comprise a peptide, a polypeptide, a protein, a lipid, a carbohydrate, or a small organic molecule, or a combination thereof. Examples of each of these molecules that bind to cell surface receptors present on the apical membrane of epithelial cells are well known to those of skill in the art. Suitable peptides or polypeptides include, but are not limited to, bacterial toxin receptor binding domains, such as the receptor binding domains from PE, cholera toxin, botulinum toxin, diptheria toxin, shiga toxin, shiga-like toxin, etc.; antibodies, including monoclonal, polyclonal, and single-chain antibodies, or derivatives thereof, growth factors, such as EGF, IGF-I, IGF-II, IGF-III etc.; cytokines, such as IL-1, IL-2, IL-3, IL-6, etc; chemokines, such as MIP-1a, MIP-1b, MCAF, IL-8, etc.; and other ligands, such as CD4, cell adhesion molecules from the immunoglobulin superfamily, integrins, ligands specific for the IgA receptor, etc. See, e.g., Pastan et al., 1992, *Annu. Rev. Biochem.* 61:331-54; and U.S. Pat. Nos. 5,668,255, 5,696,237, 5,863,745, 5,965,406, 6,022,950, 6,051,405, 6,251,392, 6,440,419, and 6,488,926. The skilled artisan can select the appropriate receptor binding domain based upon the expression pattern of the receptor to which the receptor binding domain binds.

Lipids suitable for receptor binding domains include, but are not limited to, lipids that themselves bind cell surface receptors, such as sphingosine-1-phosphate, lysophosphatidic acid, sphingosylphosphorylcholine, retinoic acid, etc.; lipoproteins such as apolipoprotein E, apolipoprotein A, etc., and glycolipids such as lipopolysaccharide, etc.; glycosphingolipids such as globotriaosylceramide and galabiosylceramide; and the like. Carbohydrates suitable for receptor binding domains include, but are not limited to, monosaccharides, disaccharides, and polysaccharides that comprise simple sugars such as glucose, fructose, galactose, etc.; and glycoproteins such as mucins, selectins, and the like. Suitable small organic molecules for receptor binding domains include, but are not limited to, vitamins, such as vitamin A, $B_1$, $B_2$, $B_3$, $B_6$, $B_9$, $B_{12}$, C, D, E, and K, amino acids, and other small molecules that are recognized and/or taken up by receptors present on the apical surface of epithelial cells. U.S. Pat. No. 5,807,832 provides an example of such small organic molecule receptor binding domains, vitamin $B_{12}$.

In certain embodiments, the receptor binding domain can bind to a receptor found on an epithelial cell. In further embodiments, the receptor binding domain can bind to a receptor found on the apical membrane of an epithelial cell. The receptor binding domain can bind to any receptor known to be present on the apical membrane of an epithelial cell by one of skill in the art without limitation. For example, the receptor binding domain can bind to $\alpha$2-MR, EGFR, or IGFR. An example of a receptor binding domain that can bind to $\alpha$2-MR is domain Ia of PE. Accordingly, in certain embodiments, the receptor binding domain is domain Ia of PE. In other embodiments, the receptor binding domain is a portion of domain Ia of PE that can bind to $\alpha$2-MR. Exemplary receptor binding domains that can bind to EGFR include, but are not limited to, EGF and TGF$\alpha$. Examples of receptor binding domains that can bind to IGFR include, but are not limited to, IGF-I, IGF-II, or IGF-III. Thus, in certain embodiments, the receptor binding domain is EGF, IGF-I, IGF-II, or IGF-III. In other embodiments, the receptor binding domain is a portion of EGF, IGF-I, IGF-II, or IGF-III that can bind to the EGF or IGF receptor.

In certain embodiments, the receptor binding domain binds to a receptor that is highly expressed on the apical membrane of a polarized epithelial cell but is not expressed or expressed at low levels on antigen presenting cells, such as, for example, dendritic cells. Exemplary receptor binding domains that have this kind of expression pattern include, but are not limited to, TGF$\alpha$, EGF, IGF-I, IGF-II, and IGF-III.

In certain embodiments, the delivery constructs of the invention comprise more than one domain that can function as a receptor binding domain. For example, the delivery construct can comprise PE domain Ia in addition to another receptor binding domain.

The receptor binding domain can be attached to the remainder of the delivery construct by any method or means known by one of skill in the art to be useful for attaching such molecules, without limitation. In certain embodiments, the receptor binding domain is expressed together with the remainder of the delivery construct as a fusion protein. Such embodiments are particularly useful when the receptor binding domain and the remainder of the construct are formed from peptides or polypeptides.

In other embodiments, the receptor binding domain is connected with the remainder of the delivery construct with a linker. In yet other embodiments, the receptor binding domain is connected with the remainder of the delivery construct without a linker. Either of these embodiments are useful when the receptor binding domain comprises a peptide, polypeptide, protein, lipid, carbohydrate, nucleic acid, or small organic molecule.

In certain embodiments, the linker can form a covalent bond between the receptor binding domain and the remainder of the delivery construct. In certain embodiments, the covalent bond can be a peptide bond. In other embodiments, the linker can link the receptor binding domain to the remainder of the delivery construct with one or more non-covalent interactions of sufficient affinity. One of skill in the art can readily recognize linkers that interact with each other with sufficient affinity to be useful in the delivery constructs of the invention. For example, biotin can be attached to the receptor binding domain, and streptavidin can be attached to the remainder of the molecule. In certain embodiments, the linker can directly link the receptor binding domain to the remainder of the molecule. In other embodiments, the linker itself comprises two or more molecules that associate in order to link the receptor binding domain to the remainder of the molecule. Exemplary linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect the receptor binding domain to the remainder of the delivery construct, the linkers can be attached to the receptor binding domain and/or the remainder of the delivery construct by any means or method known by one of skill in the art without limitation. For example, the linker can be attached to the receptor binding domain and/or the remainder of the delivery construct with an ether, ester, thioether, thioester, amide, imide, disulfide, peptide, or other suitable moiety. The skilled artisan can select the appropriate linker and method for attaching the linker based on the physical and chemical properties of the chosen receptor binding domain and the linker.

The linker can be attached to any suitable functional group on the receptor binding domain or the remainder of the molecule. For example, the linker can be attached to sulfhydryl (—S), carboxylic acid (COOH) or free amine (—NH2) groups, which are available for reaction with a suitable functional group on a linker. These groups can also be used to connect the receptor binding domain directly connected with the remainder of the molecule in the absence of a linker.

Further, the receptor binding domain and/or the remainder of the delivery construct can be derivatized in order to facilitate attachment of a linker to these moieties. For example, such derivatization can be accomplished by attaching suitable derivative such as those available from Pierce Chemical Company, Rockford, Ill. Alternatively, derivatization may involve chemical treatment of the receptor binding domain and/or the remainder of the molecule. For example, glycol cleavage of the sugar moiety of a carbohydrate or glycoprotein receptor binding domain with periodate generates free aldehyde groups. These free aldehyde groups may be reacted with free amine or hydrazine groups on the remainder of the molecule in order to connect these portions of the molecule. See, e.g., U.S. Pat. No. 4,671,958. Further, the skilled artisan can generate free sulfhydryl groups on proteins to provide a reactive moiety for making a disulfide, thioether, thioester, etc. linkage. See, e.g., U.S. Pat. No. 4,659,839.

Any of these methods for attaching a linker to a receptor binding domain and/or the remainder of a delivery construct can also be used to connect a receptor binding domain with the remainder of the delivery construct in the absence of a linker. In such embodiments, the receptor binding domain is coupled with the remainder of the construct using a method suitable for the particular receptor binding domain. Thus, any method suitable for connecting a protein, peptide, polypeptide, nucleic acid, carbohydrate, lipid, or small organic molecule to the remainder of the delivery construct known to one of skill in the art, without limitation, can be used to connect the receptor binding domain to the remainder of the construct. In addition to the methods for attaching a linker to a receptor binding domain or the remainder of a delivery construct, as described above, the receptor binding domain can be connected with the remainder of the construct as described, for example, in U.S. Pat. Nos. 6,673,905; 6,585,973; 6,596,475; 5,856,090; 5,663,312; 5,391,723; 6,171,614; 5,366,958; and 5,614,503.

In certain embodiments, the receptor binding domain can be a monoclonal antibody. In some of these embodiments, the chimeric immunogen is expressed as a fusion protein that comprises an immunoglobulin heavy chain from an immunoglobulin specific for a receptor on a cell to which the chimeric immunogen is intended to bind. The light chain of the immunoglobulin then can be co-expressed with the chimeric immunogen, thereby forming a light chain-heavy chain dimer. In other embodiments, the antibody can be expressed and assembled separately from the remainder of the chimeric immunogen and chemically linked thereto.

5.2.2. Transcytosis Domain

The delivery constructs of the invention also comprise a transcytosis domain. The transcytosis domain can be any transcytosis domain known by one of skill in the art to effect transcytosis of chimeric proteins that have bound to a cell surface receptor present on the apical membrane of an epithelial cell. In certain embodiments, the transcytosis domain is a transcytosis domain from PE, diptheria toxin, pertussis toxin, cholera toxin, heat-labile E. coli enterotoxin, shiga toxin, or shiga-like toxin. See, for example, U.S. Pat. Nos. 5,965,406, and 6,022,950. In preferred embodiments, the transcytosis domain is domain II of PE.

The transcytosis domain need not, though it may, comprise the entire amino acid sequence of domain II of native PE, which spans residues 253-364 of PE. For example, the transcytosis domain can comprise a portion of PE that spans residues 280-344 of domain II of PE. The amino acids at positions 339 and 343 appear to be necessary for transcytosis. See Siegall et al., 1991, *Biochemistry* 30:7154-59. Further, conservative or nonconservative substitutions can be made to the amino acid sequence of the transcytosis domain, as long as transcytosis activity is not substantially eliminated. A representative assay that can routinely be used by one of skill in the art to determine whether a transcytosis domain has transcytosis activity is described below.

Without intending to be limited to any particular theory or mechanism of action, the transcytosis domain is believed to permit the trafficking of the delivery construct through a polarized epithelial cell after the construct binds to a receptor present on the apical surface of the polarized epithelial cell. Such trafficking through a polarized epithelial cell is referred to herein as "transcytosis." This trafficking permits the release of the delivery construct from the basal-lateral membrane of the polarized epithelial cell.

5.2.3. Macromolecules for Delivery

The delivery constructs of the invention can also comprise a macromolecule. The macromolecule can be attached to the remainder of the delivery construct by any method known by one of skill in the art, without limitation. In certain embodiments, the macromolecule is expressed together with the remainder of the delivery construct as a fusion protein. In such embodiments, the macromolecule can be inserted into or attached to any portion of the delivery construct, so long as the receptor binding domain, the transcytosis domain, and macromolecule retain their activities. The macromolecule is connected with the remainder of the construct with a cleavable linker, or a combination of cleavable linkers, as described below.

In native PE, the Ib loop (domain Ib) spans amino acids 365 to 399, and is structurally characterized by a disulfide bond between two cysteines at positions 372 and 379. This portion of PE is not essential for any known activity of PE, including cell binding, transcytosis, ER retention or ADP ribosylation activity. Accordingly, domain Ib can be deleted entirely, or modified to contain a macromolecule.

Thus, in certain embodiments, the macromolecule can be inserted into domain Ib. If desirable, the macromolecule can be inserted into domain Ib wherein the cysteines at positions 372 and 379 are not cross-linked. This can be accomplished by reducing the disulfide linkage between the cysteines, by deleting the cysteines entirely from the Ib domain, by mutating the cysteines to other residues, such as, for example, serine, or by other similar techniques. Alternatively, the macromolecule can be inserted into the Ib loop between the cysteines at positions 372 and 379. In such embodiments, the disulfide linkage between the cysteines can be used to constrain the macromolecule if desirable. In any event, in embodiments where the macromolecule is inserted into domain Ib of PE, or into any other portion of the delivery construct, the macromolecule should be flanked by cleavable linkers such that cleavage at the cleavable linkers liberates the macromolecule from the remainder of the construct.

In other embodiments, the macromolecule can be connected with the N-terminal or C-terminal end of a polypeptide portion of the delivery construct. In such embodiments, the method of connection should be designed to avoid interference with other functions of the delivery construct, such as receptor binding or transcytosis. In yet other embodiments, the macromolecule can be connected with a side chain of an amino acid of the delivery construct. The macromolecule is connected with the remainder of the delivery construct with a cleavable linker, as described below. In such embodiments, the macromolecule to be delivered can be connected with the remainder of the delivery construct with one or more cleavable linkers such that cleavage at the cleavable linker(s) separates the macromolecule from the remainder of the delivery construct. It should be noted that, in certain embodiments, the macromolecule of interest can also comprise a short (1-20 amino acids, preferably 1-10 amino acids, and more preferably 1-5 amino acids) leader peptide in addition to the macromolecule of interest that remains attached to the macromolecule following cleavage of the cleavable linker. Preferably, this leader peptide does not affect the activity or immunogenicity of the macromolecule.

In embodiments where the macromolecule is expressed together with another portion of the delivery construct as a fusion protein, the macromolecule can be can be inserted into the delivery construct by any method known to one of skill in the art without limitation. For example, amino acids corresponding to the macromolecule can be inserted directly into the delivery construct, with or without deletion of native amino acid sequences. In certain embodiments, all or part of the Ib domain of PE can be deleted and replaced with the macromolecule. In certain embodiments, the cysteine residues of the Ib loop are deleted so that the macromolecule remains unconstrained. In other embodiments, the cysteine residues of the Ib loop are linked with a disulfide bond and constrain the macromolecule.

The macromolecule can be any macromolecule that is desired to be introduced into a subject. Thus, the macromolecule can be a peptide, a polypeptide, a protein, a nucleic acid, a carbohydrate, a lipid, a glycoprotein, synthetic organic and inorganic compounds, or any combination thereof. The macromolecule can also be a detectable compound such as a radiopaque compound, including air and barium and magnetic compounds. In certain embodiments, the macromolecule can be either soluble or insoluble in water. In certain embodiments, the macromolecule can be a macromolecule that can perform a desirable biological activity when introduced to the bloodstream of the subject. For example, the macromolecule can have receptor binding activity, enzymatic activity, messenger activity (i.e., act as a hormone, cytokine, neurotransmitter, or other signaling molecule), luminescent or other detectable activity, or regulatory activity, or any combination thereof. In, for example, diagnostic embodiments, the macromolecule can be conjugated to or can itself be a pharmaceutically acceptable gamma-emitting moiety, including but not limited to, indium and technetium, magnetic particles, radiopaque materials such as air or barium and fluorescent compounds.

In other embodiments, the macromolecule that is delivered can exert its effects in biological compartments of the subject other than the subject's blood. For example, in certain embodiments, the macromolecule can exert its effects in the lymphatic system. In other embodiments, the macromolecule can exert its effects in an organ or tissue, such as, for example, the subject's liver, heart, lungs, pancreas, kidney, brain, bone marrow, etc. In such embodiments, the macromolecule may or may not be present in the blood, lymph, or other biological fluid at detectable concentrations, yet may still accumulate at sufficient concentrations at its site of action to exert a biological effect.

Further, the macromolecule can be a protein that comprises more than one polypeptide subunit. For example, the protein can be a dimer, trimer, or higher order multimer. In certain embodiments, two or more subunits of the protein can be connected with a covalent bond, such as, for example, a disulfide bond. In other embodiments, the subunits of the protein can be held together with non-covalent interactions. One of skill in the art can routinely identify such proteins and determine whether the subunits are properly associated using, for example, an immunoassay. Exemplary proteins that comprise more than one polypeptide chain that can be delivered with a delivery construct of the invention include, but are not limited to, antibodies, insulin, IGF I, and the like.

Accordingly, in certain embodiments, the macromolecule is a peptide, polypeptide, or protein. In certain embodiments, the macromolecule comprises a peptide or polypeptide that comprises about 5, about 8, about 10, about 12, about 15, about 17, about 20, about 25, about 30, about 40, about 50, or about 60, about 70, about 80, about 90, about 100, about 200, about 400, about 600, about 800, or about 1000 amino acids. In certain embodiments, the macromolecule is a protein that comprises 1, 2, 3, 4, 5, 6, 7, 8, or more polypeptides. In certain embodiments, the peptide, polypeptide, or protein is a molecule that is commonly administered to subjects by injection. Exemplary peptides or polypeptides include, but are not limited to, IGF-I, IGF-II, IGF-III, EGF, IFN-α, IFN-β, IFN-γ, G-CSF, GM-CSF, IL-1, IL-2, IL-3, IL-6, IL-8, IL-12, EPO, growth hormone, clotting factors such as factor VII, vasopressin, calcitonin parathyroid hormone, luteinizing hormone-releasing factor, tissue plasminogen activators, adrenocorticototropin, enkephalin, glucagon-like peptide 1, asparaginase, and the like. In a preferred embodiment, the macromolecule is insulin. In certain preferred embodiments, the polypeptide is growth hormone. In even more preferred embodiments, the polypeptide is human growth hormone. In an equally preferred embodiment, the polypeptide is IFN-α, more preferably IFNα-2b. In an equally preferred embodiment, the polypeptide is insulin or proinsulin. In other embodiments, the polypeptide is green fluorescent protein. The sequences of all of these macromolecules are well known to those in the art, and attachment of these macromolecules to the delivery constructs is well within the skill of those in the art using standard techniques, as discussed below.

In certain embodiments, the macromolecule can be selected to not be cleavable by an enzyme present at the basal-lateral membrane of an epithelial cell. For example, the assays described in the examples can be used to routinely test whether such a cleaving enzyme can cleave the macromolecule to be delivered. If so, the macromolecule can be routinely altered to eliminate the offending amino acid sequence recognized by the cleaving enzyme. The altered macromolecule can then be tested to ensure that it retains activity using methods routine in the art.

Other examples of macromolecules that can be delivered according to the present invention include, but are not limited to, antineoplastic compounds, such as nitrosoureas, e.g., carmustine, lomustine, semustine, strepzotocin; methylhydrazines, e.g., procarbazine, dacarbazine; steroid hormones, e.g., glucocorticoids, estrogens, progestins, androgens, tetrahydrodesoxycaricosterone; immunoactive compounds such as immunosuppressives, e.g., pyrimethamine, trimethopterin, penicillamine, cyclosporine, azathioprine; and immunostimulants, e.g., levamisole, diethyl dithiocarbamate, enkephalins, endorphins; antimicrobial compounds such as antibiotics, e.g., β-lactam, penicillin, cephalosporins, carbapenims and monobactams, β-lactamase inhibitors, aminoglycosides, macrolides, tetracyclins, spectinomycin; antimalarials, amebicides; antiprotazoals; antifungals, e.g., amphotericin β, antivirals, e.g., acyclovir, idoxuridine, ribavirin, trifluridine, vidarbine, gancyclovir; parasiticides; antihalmintics; radiopharmaceutics; gastrointestinal drugs;

hematologic compounds; immunoglobulins; blood clotting proteins, e.g., antihemophilic factor, factor IX complex; anticoagulants, e.g., dicumarol, heparin Na; fibrolysin inhibitors, e.g., tranexamic acid; cardiovascular drugs; peripheral antiadrenergic drugs; centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, e.g., phentolamine; anti-anginal drugs; cardiac glycosides; inodilators, e.g., amrinone, milrinone, enoximone, fenoximone, imazodan, sulmazole; antidysrhythmics; calcium entry blockers; drugs affecting blood lipids, e.g., ranitidine, bosentan, rezulin; respiratory drugs; sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine $SO_4$, clinidium Br, glycopyrrolate, ipratropium Br, scopolamine HBr; neuromuscular blocking drugs; depolarizing drugs, e.g., atracurium besylate, hexafluorenium Br, metocurine iodide, succinylcholine Cl, tubocurarine Cl, vecuronium Br; centrally acting muscle relaxants, e.g., baclofen; neurotransmitters and neurotransmitter agents, e.g., acetylcholine, adenosine, adenosine triphosphate; amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, $K^+$ channel toxins; antiparkinson drugs, e.g., amaltidine HCl, benztropine mesylate, carbidopa; diuretic drugs, e.g., dichlorphenamide, methazolamide, bendroflumethiazide, polythiazide; antimigraine drugs, e.g, carboprost tromethamine mesylate, methysergide maleate.

Still other examples of macromolecules that can be delivered according to the present invention include, but are not limited to, hormones such as pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists; hormonal contraceptives; testicular hormones; gastrointestinal hormones, e.g., cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Still other examples of macromolecules that can be delivered according to the present invention include, but are not limited to, enzymes such as hyaluronidase, streptokinase, tissue plasminogen activator, urokinase, PGE-adenosine deaminase; intravenous anesthetics such as droperidol, etomidate, fetanyl citrate/droperidol, hexobarbital, ketamine HCl, methohexital Na, thiamylal Na, thiopental Na; antiepileptics, e.g., carbamazepine, clonazepam, divalproex Na, ethosuximide, mephenytoin, paramethadione, phenytoin, primidone.

Still other examples of macromolecules that can be delivered according to the present invention include, but are not limited to, peptides and proteins such as ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor α, transforming growth factor β, interferon (IFN); hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43.

Yet other examples of macromolecules that can be delivered according to the present invention include, but are not limited to, cytokines and cytokine receptors such as Interleukin-1 (IL-1), IL-2, IL-3, IL-4, IL-5, IL-6, IL-7, IL-8, IL-9, IL-10, IL11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL- 18 receptor, lymphokine inhibitory factor, macrophage colony stimulating factor, platelet derived growth factor, stem cell factor, tumor growth factor β, tumor necrosis factor, lymphotoxin, Fas, granulocyte colony stimulating factor, granulocyte macrophage colony stimulating factor, interferon α, interferon β, and interferon γ.

Still other examples of macromolecules that can be delivered according to the present invention include, but are not limited to, growth factors and protein hormones such as erythropoietin, angiogenin, hepatocyte growth factor, fibroblast growth factor, keratinocyte growth factor, nerve growth factor, tumor growth factor a, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II; chemokines such as ENA-78, ELC, GRO-α, GRO-β, GRO-γ, HRG, LIF, IP-10, MCP-1, MCP-2, MCP-3, MCP-4, MIP-1α, MIP-1β, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2; α-chemokine receptors, e.g., CXCR1, CXCR2, CXCR3, CXCR4, CXCR5, CXCR6, CXCR7; and β-chemokine receptors, e.g., CCR1, CCR2, CCR3, CCR4, CCR5, CCR6, CCR7.

Yet other examples of macromolecules that can be delivered according to the present invention include, but are not limited to, chemotherapeutics, such as chemotherapy or anti-tumor agents which are effective against various types of human cancers, including leukemia, lymphomas, carcinomas, sarcomas, myelomas etc., such as, for example, doxorubicin, mitomycin, cisplatin, daunorubicin, bleomycin, actinomycin D, and neocarzinostatin.

Still other examples of macromolecules that can be delivered according to the present invention include, but are not limited to, antibodies such as anti-cluster of differentiation antigen CD-1 through CD-166 and the ligands or counter receptors for these molecules; anti-cytokine antibodies, e.g., anti-IL-1 through anti-IL-18 and the receptors for these molecules; anti-immune receptor antibodies; antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fc γ-receptors, Fc α-receptors, Fc ε-receptors, Fc μ-receptors, and their ligands; anti-metalloproteinase antibodies, e.g., antibodies specific for collagenase, MMP-1 through MMP-8, TIMP-1, TIMP-2; anti-cell lysis/proinflammatory molecules, e.g., perforin, complement components, prostanoids, nitron oxide, thromboxanes; and anti-adhesion molecules, e.g., carcioembryonic antigens, lamins, fibronectins.

Yet other examples of macromolecules that can be delivered according to the present invention include, but are not limited to, antiviral agents such as reverse transcriptase inhibitors and nucleoside analogs, e.g., ddl, ddC, 3TC, ddA, AZT; protease inhibitors, e.g., Invirase, ABT-538; and inhibitors of in RNA processing, e.g., ribavirin.

Further, specific examples of macromolecules that can be delivered with the delivery constructs of the present invention Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb); Ceclor, Lorabid, Dynabac, Prozac, Darvon, Permax, Zyprexa, Humalog, Axid, Gemzar, Evista (Eli Lily); Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.); Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn); Lopid, Accrupil, Dilantin, Cognex, Neurontin, Loestrin, Dilzem, Fempatch, Estrostep, Rezulin, Lipitor, Omnicef, FemHRT, Suramin, and Clinafloxacin (Warner Lambert).

Yet further examples of macromolecules which may be delivered by the delivery constructs of the present invention may be found in: Goodman and Gilman's The Pharmacological Basis of Therapeutics, 9th ed. McGraw-Hill 1996, incorporated herein by reference in its entirety.

In certain embodiments, the macromolecule can be inactive or in a less active form when administered, then be activated in the subject. For example, the macromolecule can be a peptide or polypeptide with a masked active site. The peptide or polypeptide can be activated by removing the masking moiety. Such removal can be accomplished by peptidases or proteases in the cases of peptide or polypeptide masking agents. Alternatively, the masking agent can be a chemical moiety that is removed by an enzyme present in the subject. This strategy can be used when it is desirable for the macromolecule to be active in limited circumstances. For example, it may be useful for a macromolecule to be active only in the liver of the subject. In such cases, the macromolecule can be selected to have a masking moiety that can be removed by an enzyme that is present in the liver, but not in other organs or tissues. Exemplary methods and compositions for making and using such masked macromolecules can be found in U.S. Pat. Nos. 6,080,575, 6,265,540, and 6,670, 147.

In another example of such embodiments, the macromolecule can be a pro-macromolecule that is activated by a biological activity, for example by processing, present in the subject. For example, the exemplary macromolecule proinsulin can be delivered with a delivery construct of the present invention. Following delivery of the pro-macromolecule, it can be activated in the subject by appropriate processing enzymes. While it is believed that proinsulin is processed by enzymes (the endoproteases PC2 and PC3) present in highest concentration in secretory granules of pancreatic beta-cells, it is also believed that such enzyme are present in sufficient concentration in other compartments to permit activation of the pro-macromolecule into its fully active form. Further, it should be noted that many pro-macromolecules, including, for example, proinsulin, also exhibit activity similar to that of the fully active molecule. See, for example, Desbuquois et al., 2003, *Endocrinology* 12:5308-5321. Thus, even if not all of the pro-macromolecule is converted to the fully active form, the pro-molecule can in many cases still exert a desireable biological activity in the subject.

5.2.4. Cleavable Linkers

In the delivery constructs of the invention, the macromolecule to be delivered to the subject is connected with the remainder of the delivery construct with one or more cleavable linkers. The number of cleavable linkers present in the construct depends, at least in part, on the location of the macromolecule in relation to the remainder of the delivery construct and the nature of the macromolecule. When the macromolecule is inserted into the delivery construct, the macromolecule can be flanked by cleavable linkers, such that cleavage at both linkers separates the macromolecule. The flanking cleavable linkers can be the same or different from each other. When the macromolecule can be separated from the remainder of the delivery construct with cleavage at a single linker, the delivery constructs can comprise a single cleavable linker. Further, where the macromolecule is, e.g., a dimer or other multimer, each subunit of the macromolecule can be separated from the remainder of the delivery construct and/or the other subunits of the macromolecule by cleavage at the cleavable linker.

The cleavable linkers are generally cleavable by a cleaving enzyme that is present at or near the basal-lateral membrane of an epithelial cell. By selecting the cleavable linker to be cleaved by such enzymes, the macromolecule can be liberated from the remainder of the construct following transcytosis across the mucous membrane and release from the epithelial cell into the cellular matrix on the basal-lateral side of the membrane. Further, cleaving enzymes could be used that are present inside the epithelial cell, such that the cleavable linker is cleaved prior to release of the delivery construct from the basal-lateral membrane, so long as the cleaving enzyme does not cleave the delivery construct before the delivery construct enters the trafficking pathway in the polarized epithelial cell that results in release of the delivery construct and macromolecule from the basal-lateral membrane of the cell.

In certain embodiments, the cleaving enzyme is a peptidase. In other embodiments, the cleaving enzyme is an RNAse. In yet other embodiments, the cleaving enzyme can cleave carbohydrates. Preferred peptidases include, but are not limited to, Cathepsin GI, Chymotrypsin I, Elastase I, Subtilisin AI, Subtilisin AII, Thrombin I, and Urokinase I. Table I presents these enzymes together with an amino acid sequence that is recognized and cleaved by the particular peptidase.

TABLE 1

Peptidases Present Near Basal-Lateral Mucous Membranes

| Peptidase | Amino Acid Sequence Recognized and Cleaved | |
|---|---|---|
| Cathepsin GI | Ala-Ala-Pro-Phe | (SEQ ID NO.:4) |
| Chymotrypsin I | Gly-Gly-Phe | (SEQ ID NO.:5) |
| Elastase I | Ala-Ala-Pro-Val | (SEQ ID NO.:6) |
| Subtilisin AI | Gly-Gly-Leu | (SEQ ID NO.:7) |
| Subtilisin AII | Ala-Ala-Leu | (SEQ ID NO.:8) |
| Thrombin I | Phe-Val-Arg | (SEQ ID NO.:9) |
| Urokinase I | Val-Gly-Arg | (SEQ ID NO.:10) |

In certain embodiments, the delivery construct can comprise more than one cleavable linker, wherein cleavage at either cleavable linker can separate the macromolecule to be delivered from the delivery construct. In certain embodiments, the cleavable linker can be selected based on the sequence, in the case of peptide, polypeptide, or protein macromolecules for delivery, to avoid the use of cleavable linkers that comprise sequences present in the macromolecule to be delivered. For example, if the macromolecule comprises AAL, the cleavable linker can be selected to be cleaved by an enzyme that does not recognize this sequence.

Further, the cleavable linker preferably exhibits a greater propensity for cleavage than the remainder of the delivery construct. As one skilled in the art is aware, many peptide and polypeptide sequences can be cleaved by peptidases and proteases. In certain embodiments, the cleavable linker is selected to be preferentially cleaved relative to other amino acid sequences present in the delivery construct during administration of the delivery construct. In certain embodiments, the receptor binding domain is substantially (e.g., about 99%, about 95%, about 90%, about 85%, about 80, or about 75%) intact following delivery of the delivery construct to the bloodstream of the subject. In certain embodiments, the translocation domain is substantially (e.g., about 99%, about 95%, about 90%, about 85%, about 80, or about 75%) intact following delivery of the delivery construct to the bloodstream of the subject. In certain embodiments, the macromolecule is substantially (e.g., about 99%, about 95%, about 90%, about 85%, about 80, or about 75%) intact following delivery of the delivery construct to the bloodstream of the subject. In certain embodiments, the cleavable linker is substantially (e.g., about 99%, about 95%, about 90%, about 85%, about 80, or about 75%) cleaved following delivery of the delivery construct to the bloodstream of the subject.

In other embodiments, the cleavable linker is cleaved by a cleaving enzyme found in the plasma of the subject. Any cleaving enzyme known by one of skill in the art to be present in the plasma of the subject can be used to cleave the cleavable linker. Uses of such enzymes to cleave the cleavable linkers is less preferred than use of cleaving enzymes found near the basal-lateral membrane of a polarized epithelial cell because it is believed that more efficient cleavage will occur in near the basal-lateral membrane. However, if the skilled artisan determines that cleavage mediated by a plasma enzyme is sufficiently efficient to allow cleavage of a sufficient fraction of the delivery constructs to avoid adverse effects, such plasma cleaving enzymes can be used to cleave the delivery constructs. Accordingly, in certain embodiments, the cleavable linker can be cleaved with an enzyme that is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin, and esterase. See, e.g., U.S. Pat. No. 6,673,574. Table 2 presents these enzymes together with an amino acid sequence(s) recognized by the particular peptidase. The peptidase cleaves a peptide comprising these sequences at the N-terminal side of the amino acid identified with an asterisk.

TABLE 2

Plasma Peptidases

| Peptidase | Amino Acid Sequence Recognized and Cleaved | |
|---|---|---|
| Caspase-1 | Tyr-Val-Ala-Asp-Xaa* | (SEQ ID NO.:11) |
| Caspase-3 | Asp-Xaa-Xaa-Asp-Xaa* | (SEQ ID NO.:12) |
| Proprotein convertase 1 | Arg-(Xaa)$_n$-Arg-Xaa*; n = 0, 2, 4 or 6 | (SEQ ID NO.:13) |
| Proprotein convertase 2 | Lys-(Xaa)$_n$-Arg-Xaa*; n = 0, 2, 4, or 6 | (SEQ ID NO.:14) |
| Proprotein convertase 4 | Glp-Arg-Thr-Lys-Arg-Xaa* | (SEQ ID NO.:15) |
| Proprotein convertase 4 PACE 4 | Arg-Val-Arg-Arg-Xaa* | (SEQ ID NO.:16) |
| | Decanoyl-Arg-Val-Arg-Arg-Xaa* | (SEQ ID NO.:17) |
| Prolyloligopeptidase Endothelin cleaving enzyme in combination with dipeptidyl-peptidase IV | Pro-Xaa*-Trp-Val-Pro-Xaa | (SEQ ID NO.:18) |
| Signal peptidase | Trp-Val*-Ala-Xaa | (SEQ ID NO.:19) |
| Neprilysin in combination with dipeptidyl-peptidase IV | Xaa-Phe*-Xaa-Xaa | (SEQ ID NO.:20) |
| | Xaa-Tyr*-Xaa-Xaa | (SEQ ID NO.:21) |
| | Xaa-Trp*-Xaa-Xaa | (SEQ ID NO.:22) |

TABLE 2-continued

Plasma Peptidases

| Peptidase | Amino Acid Sequence Recognized and Cleaved | |
|---|---|---|
| Renin in combination with dipeptidyl-peptidase IV | Asp-Arg-Tyr-Ile-Pro-Phe-His-Leu*-Leu-(Val, Ala or Pro)-Tyr-(Ser, Pro, or Ala) | (SEQ ID NO.:23) |

Thus, in certain more preferred embodiments, the cleavable linker can be any cleavable linker known by one of skill in the art to be cleavable by an enzyme that is present at the basal-lateral membrane of an epithelial cell. In certain embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide. In certain embodiments, the cleavable linker is a peptide that comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10).

Alternatively, in less preferred embodiments, the cleavable linker can be any cleavable linker known by one of skill in the art to be cleavable by an enzyme that is present in the plasma of the subject to whom the delivery construct is administered. In certain embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide. In certain embodiments, the cleavable linker is a peptide that comprises an amino acid sequence that is selected from the group consisting of amino acid sequences presented in Table 2.

In certain embodiments, the delivery construct comprises more than one cleavable linker. In certain embodiments, cleavage at any of the cleavable linkers will separate the macromolecule to be delivered from the remainder of the delivery construct. In certain embodiments, the delivery construct comprises a cleavable linker cleavable by an enzyme present at the basal-lateral side of a polarized epithelial membrane and a cleavable linkers cleavable by an enzyme that is present in the plasma of the subject to whom the delivery construct is administered.

Further, Tables 4 and 5, below, present results of experiments testing the ability of peptidases to cleave substrates when applied to the basal-lateral or apical surface of a polarized epithelial membrane. The sequences recognized by these enzymes are well-known in the art. Thus, in certain embodiments, the delivery construct comprises a cleavable linker that is cleavable by an enzyme listed in Tables 4 and 5. Preferred peptidases exhibit higher activity on the basolateral side of the membrane. Particularly preferred peptidases exhibit much higher (e.g., 100%, 200%, or more increase in activity relative to the apical side) on the basolateral side. Thus, in certain embodiments, the cleavable linker is cleavable by an enzyme that exhibits 50% higher activity on the basal-lateral side of the membrane than on the apical side of the membrane. In certain embodiments, the cleavable linker is cleavable by an enzyme that exhibits 100% higher activity on the basal-lateral side of the membrane than on the apical side of the membrane. In certain embodiments, the cleavable linker is cleavable by an enzyme that exhibits 200% higher activity on the basal-lateral side of the membrane than on the apical side of the membrane. In certain embodiments, the cleavable linker is cleavable by an enzyme that exhibits 500% higher activity on the basal-lateral side of the membrane than on the apical side of the membrane. In certain embodiments, the cleavable linker is cleavable by an enzyme that exhibits 1,000% higher activity on the basal-lateral side of the membrane than on the apical side of the membrane. In certain embodiments, the cleavable linker is cleavable by an enzyme that exhibits 2,000% higher activity on the basal-lateral side of the membrane than on the apical side of the membrane. In certain embodiments, the cleavable linker is cleavable by an enzyme that exhibits 3,000% higher activity on the basal-lateral side of the membrane than on the apical side of the membrane. In certain embodiments, the cleavable linker is cleavable by an enzyme that exhibits 5,000% higher activity on the basal-lateral side of the membrane than on the apical side of the membrane. In certain embodiments, the cleavable linker is cleavable by an enzyme that exhibits 10,000% higher activity on the basal-lateral side of the membrane than on the apical side of the membrane.

Still further, the results in Tables 4 and 5 indicate that certain enzymes are present in higher concentration or exhibit greater activity in certain epithelial lineages as compared to other epithelial lineages. Thus, the experiments described below can be used to test whether the particular epithelial cell lineage through which a macromolecule will be delivered exhibits the desired cleavage activity. In certain embodiments, the cleavage activity is present in tracheal epithelial cells, but not intestinal epithelial cells. In other embodiments, the cleavage activity is present in intestinal epithelial cells but not tracheal epithelial cells. In certain embodiments, the cleavage activity is present in intestinal epithelial cells and tracheal epithelial cells.

In certain embodiments, the cleavable linker may be cleavable by any enzyme that preferentially cleaves at the basolateral side of an epithelial membrane as compared to the apical side of the membrane. Example 6.4, below, describes an assay that can be used to assess the activity of such enzymes, while Table 7, appended to the end of this document, provides short names and accession numbers for every known human protease or peptidase. Any cleavage sequence recognized by such proteases or peptidases that preferentially cleaves a test substrate on the basolateral side of an epithelial membrane, or in the plasma, as compared to the apical side of such a membrane can also be used in the methods and compositions of the present invention. In such embodiments, one of skill in the art can readily determine the amino acid sequence recognized by such peptidases or proteases according to standard procedures known in the art or according to the known sequences recognized by the proteases and peptidases.

The examples below provide methods for identifying cleaving enzymes that are present at or near the basal-lateral membrane of a polarized epithelial cell. The skilled artisan can routinely use such methods to identify additional cleaving enzymes and the chemical structure(s) identified and cleaved by such cleaving enzymes. Delivery constructs comprising such cleavable linkers and methods of delivering macromolecules using delivery constructs comprising such cleavable linkers are also within the scope of the present invention, whether or not such cleaving enzymes are presented in Table 7.

In other embodiments, the cleavable linker can be a cleavable linker that is cleaved following a change in the environment of the delivery construct. For example, the cleavable linker can be a cleavable linker that is pH sensitive and is cleaved by a change in pH that is experienced when the delivery construct is released from the basal-lateral membrane of a polarized epithelial cell. For instance, the intestinal lumen is strongly alkaline, while plasma is essentially neutral. Thus, a cleavable linker can be a moiety that is cleaved upon a shift from alkaline to neutral pH. The change in the environment of the delivery construct that cleaves the cleavable linker can be any environmental change that that is experienced when the delivery construct is released from the basal-lateral membrane of a polarized epithelial cell known by one of skill in the art, without limitation.

5.3. Methods for Delivering a Macromolecule

In another aspect, the invention provides methods for local or systemic delivery of a macromolecule to a subject. These methods generally comprise administering a delivery construct of the invention to a mucous membrane of the subject to whom the macromolecule is delivered. The delivery construct is typically administered in the form of a pharmaceutical composition, as described below.

Thus, in certain aspects, the invention provides a method for delivering a macromolecule to a subject. The method comprises contacting an apical surface of a polarized epithelial cell of the subject with a delivery construct. In certain embodiments, the delivery construct comprises a receptor binding domain, a transcytosis domain, a cleavable linker, and the macromolecule to be delivered. The transcytosis domain can transcytose the macromolecule to and through the basal-lateral membrane of said epithelial cell. The cleavable linker can be cleaved by an enzyme that is present at a basal-lateral membrane of a polarized epithelial cell of the subject or in the plasma of the subject. Cleavage at the cleavable linker separates the macromolecule from the remainder of the delivery construct, thereby delivering the macromolecule to the subject.

In certain embodiments, the enzyme that is present at or near a basal-lateral membrane of a polarized epithelial cell is selected from the group consisting of Cathepsin GI, Chymotrypsin I, Elastase I, Subtilisin AI, Subtilisin AII, Thrombin I, and Urokinase I. In certain embodiments, the cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.: 10).

In certain embodiments, the receptor binding domain is selected from the group consisting of receptor binding domains from *Pseudomonas* exotoxin A, cholera toxin, diptheria toxin, shiga toxin, or shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; and IL-8. In certain embodiments, the receptor binding domain binds to a cell surface receptor selected from the group consisting of α2-macroglobulin receptor, EGFR, IGFR, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor.

In certain embodiments, the transcytosis domain is selected from the group consisting of transcytosis domains from *Pseudomonas* exotoxin A, diptheria toxin, pertussis toxin, cholera toxin, heat-labile *E. coli* enterotoxin, shiga toxin, and shiga-like toxin.

In certain embodiments, the macromolecule is selected from the group consisting of a peptide, a polypeptide, a protein, a nucleic acid, and a lipid. In a preferred embodiment, the macromolecule is growth hormone. Even more preferably, the macromolecule is human growth hormone.

In certain embodiments, the invention provides a method for delivering a macromolecule to the bloodstream of a subject that results in at least about 30% bioavailability of the macromolecule, comprising administering a delivery construct comprising the macromolecule to the subject, thereby delivering at least about 30% of the total macromolecule administered to the blood of the subject in a bioavailable form of the macromolecule. In certain embodiments, at least about 10% of the total macromolecule administered is bioavailable to the subject. In certain embodiments, at least about 15% of the total macromolecule administered is bioavailable to the subject. In certain embodiments, at least about 20% of the total macromolecule administered is bioavailable to the subject. In certain embodiments, at least about 25% of the total macromolecule administered is bioavailable to the subject. In certain embodiments, at least about 35% of the total macromolecule administered is bioavailable to the subject. In certain embodiments, at least about 40% of the total macromolecule administered is bioavailable to the subject. In certain embodiments, at least about 45% of the total macromolecule administered is bioavailable to the subject. In certain embodiments, at least about 50% of the total macromolecule administered is bioavailable to the subject. In certain embodiments, at least about 55% of the total macromolecule administered is bioavailable to the subject. In certain embodiments, at least about 60% of the total macromolecule administered is bioavailable to the subject. In certain embodiments, at least about 65% of the total macromolecule administered is bioavailable to the subject. In certain embodiments, at least about 70% of the total macromolecule administered is bioavailable to the subject. In certain embodiments, at least about 75% of the total macromolecule administered is bioavailable to the subject. In certain embodiments, at least about 80% of the total macromolecule administered is bioavailable to the subject. In certain embodiments, at least about 85% of the total macromolecule administered is bioavailable to the subject. In certain embodiments, at least about 90% of the total macromolecule administered is bioavailable to the subject. In certain embodiments, at least about 95% of the total macromolecule administered is bioavailable to the subject. In certain embodiments, the percentage of bioavailability of the macromolecule is determined by comparing the amount of macromolecule present in a subject's blood following administration of a delivery construct comprising the macromolecule to the amount of macromolecule present in a subject's blood following administration of the macromolecule through another route of administration. In certain embodiments, the other route of administration is injection, e.g., subcutaneous injection, intravenous injection, intra-arterial injection, etc. In other embodiments, the percentage of bioavailability of the macromolecule is determined by comparing the amount of macromolecule present in a subject's blood following administration of a delivery construct comprising the macromolecule to the total amount of macromolecule administered as part of the delivery construct.

In certain embodiments, peak plasma concentrations of the delivered macromolecule in the subject are achieved about 10 minutes after administration. In certain embodiments, peak plasma concentrations of the delivered macromolecule in the subject are achieved about 15 minutes after administration. In certain embodiments, peak plasma concentrations of the delivered macromolecule in the subject are achieved about 5 minutes after administration. In certain embodiments, peak plasma concentrations of the delivered macromolecule in the subject are achieved about 20 minutes after administration. In certain embodiments, peak plasma concentrations of the delivered macromolecule in the subject are achieved about 25 minutes after administration. In certain embodiments, peak plasma concentrations of the delivered macromolecule in the subject are achieved about 30 minutes after administration. In certain embodiments, peak plasma concentrations of the delivered macromolecule in the subject are achieved about 35 minutes after administration. In certain embodiments, peak plasma concentrations of the delivered macromolecule in the subject are achieved about 40 minutes after administration. In certain embodiments, peak plasma concentrations of the delivered macromolecule in the subject are achieved about 45 minutes after administration. In certain embodiments, peak plasma concentrations of the delivered macromolecule in the subject are achieved about 50 minutes after administration. In certain embodiments, peak plasma concentrations of the delivered macromolecule in the subject are achieved about 55 minutes after administration. In certain embodiments, peak plasma concentrations of the delivered macromolecule in the subject are achieved about 60 minutes after administration. In certain embodiments, peak plasma concentrations of the delivered macromolecule in the subject are achieved about 90 minutes after administration. In certain embodiments, peak plasma concentrations of the delivered macromolecule in the subject are achieved about 120 minutes after administration.

In certain embodiments, the peak plasma concentration of the delivered macromolecule is between about 0.01 ng/ml plasma and about 10 µg/ml plasma. In certain embodiments, the peak plasma concentration of the delivered macromolecule is between about 0.01 ng/ml plasma and about 1 µg/ml plasma. In certain embodiments, the peak plasma concentration of the delivered macromolecule is between about 0.01 ng/ml plasma and about 0.1 µg/ml plasma. In certain embodiments, the peak plasma concentration of the delivered macromolecule is between about 0.01 ng/ml plasma and about 10 ng/ml plasma. In certain embodiments, the peak plasma concentration of the delivered macromolecule is between about 1 ng/ml plasma and about 10 µg/ml plasma. In certain embodiments, the peak plasma concentration of the delivered macromolecule is between about 1 ng/ml plasma and about 1 µg/ml plasma. In certain embodiments, the peak plasma concentration of the delivered macromolecule is between about 1 ng/ml plasma and about 0.5 µg/ml plasma. In certain embodiments, the peak plasma concentration of the delivered macromolecule is between about 1 ng/ml plasma and about 0.1 µg/ml plasma. In certain embodiments, the peak plasma concentration of the delivered macromolecule is between about 10 ng/ml plasma and about 1 µg/ml plasma. In certain embodiments, the peak plasma concentration of the delivered macromolecule is between about 10 ng/ml plasma and about 0.5 µg/ml plasma.

In certain embodiments, the peak plasma concentration of the delivered macromolecule is at least about 10 µg/ml plasma. In certain embodiments, the peak plasma concentration of the delivered macromolecule is at least about 5 µg/ml plasma. In certain embodiments, the peak plasma concentration of the delivered macromolecule is at least about 1 µg/ml plasma. In certain embodiments, the peak plasma concentration of the delivered macromolecule is at least about 500 ng/ml plasma. In certain embodiments, the peak plasma concentration of the delivered macromolecule is at least about 250 ng/ml plasma. In certain embodiments, the peak plasma concentration of the delivered macromolecule is at least about 100 ng/ml plasma. In certain embodiments, the peak plasma concentration of the delivered macromolecule is at least about 50 ng/ml plasma. In certain embodiments, the peak plasma concentration of the delivered macromolecule is at least about 10 ng/ml plasma. In certain embodiments, the peak plasma concentration of the delivered macromolecule is at least about 5 ng/ml plasma. In certain embodiments, the peak plasma concentration of the delivered macromolecule is at least about 1 ng/ml plasma. In certain embodiments, the peak plasma concentration of the delivered macromolecule is at least about 0.1 ng/ml plasma.

Moreover, without intending to be bound to any particular theory or mechanism of action, it is believed that oral administration of a delivery construct can deliver a higher effective concentration of the delivered macromolecule to the liver of the subject than is observed in the subject's plasma. "Effective concentration," in this context, refers to the concentration experienced by targets of the macromolecule and can be determined by monitoring and/or quantifying downstream effects of macromolecule-target interactions. While still not bound to any particular theory, it is believed that oral administration of the delivery construct results in absorption of the delivery construct through polarized epithelial cells of the digestive mucosa, e.g., the intestinal mucosa, followed by cleavage of the construct and release of the macromolecule at the basolateral side of the mucous membrane. As one of skill in the art will recognize, the blood at the basolateral membrane of such digestive mucosa is carried from this location to the liver via the portal venous system. Thus, when the macromolecule exerts a biological activity in the liver, such as, for example, activities mediated by growth hormone, insulin, IGF-I, etc. binding to their cognate receptors, the macromolecule is believed to exert an effect in excess of what would be expected based on the plasma concentrations observed in the subject. Accordingly, in certain embodiments, the invention provides a method of administering a macromolecule to a subject that comprises orally administering a delivery construct comprising the macromolecule to the subject, wherein the macromolecule is delivered to the subject's liver at a higher effective concentration than observed in the subject's plasma.

In certain embodiments, the epithelial cell is selected from the group consisting of nasal epithelial cells, oral epithelial cells, intestinal epithelial cells, rectal epithelial cells, vaginal epithelial cells, and pulmonary epithelial cells.

In certain embodiments, the subject is a mammal. In further embodiments, the subject is a rodent, a lagomorph, or a primate. In yet further embodiments, the rodent is a mouse or rat. In other embodiments, the lagomorph is a rabbit. In still other embodiments, the primate is a human, monkey, or ape. In a preferred embodiment, the subject is a human.

In another aspect, the invention provides a method for delivering a macromolecule to the bloodstream of a subject that induces a lower titer of antibodies against the macromolecule than other routes of administration. Without intending to be bound by any particular theory or mechanism of action, it is believed that entry of the macromolecule through a mucous membrane, e.g., through the intestinal mucosa, causes the immune system to tolerate the macromolecule better than if the macromolecule were, for example, injected.

Thus, a lower titer of antibodies against the macromolecule can be produced in the subject by delivering the macromolecule with a delivery construct of the invention through the mucosa rather than injecting the macromolecule, for example, subcutaneously, intravenously, intra-arterially, intraperitoneally, or otherwise. Generally, the time at which the lower titer of antibodies detected for the alternate routes of administration is detected should be roughly comparable; for example, the titer of antibodies can be determined at about 1 week, at about 2 weeks, at about 3 weeks, at about 4 weeks, at about 2 months, or at about 6 months following administration of the macromolecule with the delivery construct or by injection.

Accordingly, in certain embodiments, the invention provides a method for delivering a macromolecule to the bloodstream a subject that comprises contacting a delivery construct of the invention that comprises the macromolecule to be delivered to an apical surface of a polarized epithelial cell of the subject, such that the macromolecule is administered to the bloodstream of the subject, wherein a lower titer of antibodies specific for the macromolecule is induced in the serum of the subject than is induced by subcutaneously administering the macromolecule separately from the remainder of the delivery construct to a subject.

In certain embodiments, the macromolecule is selected from the group consisting of a peptide, a polypeptide, a protein, a nucleic acid, and a lipid. In certain embodiments, the macromolecule is selected from the group consisting of polypeptide hormones, cytokines, chemokines, growth factors, and clotting factors. In certain embodiments, the macromolecule is selected from the group consisting of IGF-I, IGF-II, IGF-III, EGF, IFN-α, IFN-β, IFN-γ, G-CSF, GM-CSF, IL-1, IL-2, IL-3, IL-6, IL-8, IL-12, EPO, growth hormone, factor VII, vasopressin, calcitonin, parathyroid hormone, luteinizing hormone-releasing factor, tissue plasminogen activators, adrenocorticototropin, enkephalin, and glucagon-like peptide 1. In certain embodiments, the macromolecule is human growth hormone. In certain embodiments, the macromolecule is human insulin. In certain embodiments, the subject is a mouse, rat, dog, goat, or human.

In certain embodiments, the titer of antibodies specific for the macromolecule induced in the serum of the subject by the macromolecule delivered by the delivery construct is less than about 95% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 90% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 85% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 80% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 75% of the titer of antibodies induced by subcutaneously administering the macromolecule separately from the remainder of the delivery construct.

In certain embodiments, the titer of antibodies specific for the macromolecule induced in the serum of the subject by the macromolecule delivered by the delivery construct is less than about 70% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 65% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 60% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 55% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 55% of the titer of antibodies induced by subcutaneously administering the macromolecule separately from the remainder of the delivery construct.

In certain embodiments, the titer of antibodies specific for the macromolecule induced in the serum of the subject by the macromolecule delivered by the delivery construct is less than about 50% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 45% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 40% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 35% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 30% of the titer of antibodies induced by subcutaneously administering the macromolecule separately from the remainder of the delivery construct.

In certain embodiments, the titer of antibodies specific for the macromolecule induced in the serum of the subject by the macromolecule delivered by the delivery construct is less than about 25% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than 20% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 15% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 10% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 5% of the titer of antibodies induced by subcutaneously administering the macromolecule separately from the remainder of the delivery construct. In certain embodiments, the titer of antibodies specific for the macromolecule induced in the serum of the subject by the macromolecule delivered by the delivery construct is less than about 1% of the titer of antibodies induced by subcutaneously administering the macromolecule separately from the remainder of the delivery construct.

5.3.1. Methods of Administration

The delivery constructs of the invention can be administered to a subject by any method known to one of skill in the art. In certain embodiments, the delivery constructs are contacted to a mucosal membrane of the subject. For example, the mucosal membrane can be present in the eye, nose, mouth, trachea, lungs, esophagus, stomach, small intestine, large intestine, rectum, anus, sweat glands, vulva, vagina, or penis of the subject. Preferably, the mucosal membrane is a mucosal membrane present in the digestive tract of the subject, such as a mucosal membrane in the mouth, esophagus, stomach, small intestine, large intestine, or rectum of the subject.

In such embodiments, the delivery constructs are preferably administered to the subject orally. Thus, the delivery construct can be formulated to protect the delivery construct from degradation in the acid environment of the stomach, if necessary. For example, many embodiments of the delivery constructs of the invention comprise polypeptide domains with defined activities. Unless such delivery constructs are protected from acid and/or enzymatic hydrolysis in the stomach, the constructs will generally be digested before delivery of substantial amounts of the macromolecule to be delivered. Accordingly, composition formulations that protect the delivery construct from degradation can be used in administration of these delivery constructs.

5.3.2. Dosage

Generally, a pharmaceutically effective amount of the delivery construct of the invention is administered to a subject. The skilled artisan can readily determine if the dosage of the delivery construct is sufficient to deliver an effective amount of the macromolecule, as described below. In certain embodiments, between about 1 µg and about 1 g of delivery construct is administered. In other embodiments, between about 10 µg and about 500 mg of delivery construct is administered. In still other embodiments, between about 10 µg and about 100 mg of delivery construct is administered. In yet other embodiments, between about 10 µg and about 1000 µg of delivery construct is administered. In still other embodiments, between about 10 µg and about 250 µg of delivery construct is administered. In yet other embodiments, between about 10 µg and about 100 µg of delivery construct is administered. Preferably, between about 10 µg and about 50 µg of delivery construct is administered.

The volume of a composition comprising the delivery construct that is administered will generally depend on the concentration of delivery construct and the formulation of the composition. In certain embodiments, a unit dose of the delivery construct composition is between about 0.05 ml and about 1 ml, preferably about 0.5 ml. The delivery construct compositions can be prepared in dosage forms containing between 1 and 50 doses (e.g., 0.5 ml to 25 ml), more usually between 1 and 10 doses (e.g., 0.5 ml to 5 ml)

The delivery construct compositions of the invention can be administered in one dose or in multiple doses. A dose can be followed by one or more doses spaced by about 1 to about 6 hours, by about 6 to about 12 hours, by about 12 to about 24 hours, by about 1 day to about 3 days, by about 1 day to about 1 week, by about 1 week to about 2 weeks, by about 2 weeks to about 1 month, by about 4 to about 8 weeks, by about 1 to about 3 months, or by about 1 to about 6 months.

The macromolecules to be delivered are generally macromolecules for which a large amount of knowledge regarding dosage, frequency of administration, and methods for assessing effective concentrations in subjects has accumulated. Such knowledge can be used to assess efficiency of delivery, effective concentration of the macromolecule in the subject, and frequency of administration. Thus, the knowledge of those skilled in the art can be used to determine whether, for example, the amount of macromolecule delivered to the subject is an effective amount, the dosage should be increased or decreased, the subject should be administered the delivery construct more or less frequently, and the like.

5.3.3. Determining Amounts of Macromolecule Delivered

The methods of the invention can be used to deliver, either locally or systemically, a pharmaceutically effective amount of a macromolecule to a subject. The skilled artisan can determine whether the methods result in delivery of such a pharmaceutically effective amount of the macromolecule. The exact methods will depend on the macromolecule that is delivered, but generally will rely on either determining the concentration of the macromolecule in the blood of the subject or in the biological compartment of the subject where the macromolecule exerts its effects. Alternatively or additionally, the effects of the macromolecule on the subject can be monitored.

For example, in certain embodiments of the present invention, the macromolecule that is delivered is insulin, e.g., human insulin. In such embodiments, the skilled artisan can determine whether a pharmaceutically effective amount of human insulin had been delivered to the subject by, for example, taking a plasma sample from the subject and determining the concentration of human insulin therein. One exemplary method for determining the concentration of human insulin is by performing an ELISA assay, but any other suitable assay known to the skilled artisan can be used.

Alternatively, one of skill in the art can determine if an effective amount of human insulin had been delivered to the subject by monitoring the blood sugar concentrations of the subject. As is well-known in the art, human insulin, among other activities, acts on hepatocytes to promote glycogen formation, thereby reducing plasma glucose concentrations. Accordingly, the subject's plasma glucose concentration can be monitored to determine whether an effective amount of insulin had been delivered.

Any effect of a macromolecule that is administered that is known by one of skill in the art, without limitation, can be assessed in determining whether an effective amount of the macromolecule has been administered. Exemplary effects include, but are not limited to, receptor binding, receptor activation, downstream effects of receptor binding, downstream effects of receptor activation, coordination of compounds, effective blood clotting, bone growth, wound healing, cellular proliferation, etc. The exact effect that is assessed will depend on the macromolecule that is delivered.

5.4. Polynucleotides Encoding Delivery Constructs

In another aspect, the invention provides polynucleotides comprising a nucleotide sequence encoding the delivery constructs. These polynucleotides are useful, for example, for making the delivery constructs. In yet another aspect, the invention provides an expression system that comprises a recombinant polynucleotide sequence encoding a receptor binding domain, a transcytosis domain, and a polylinker insertion site for a polynucleotide sequence encoding a macromolecule. The polylinker insertion site can be anywhere in the polynucleotide sequence so long as the polylinker insertion does not disrupt the receptor binding domain or the transcytosis domain. The polylinker insertion site should be oriented near a polynucleotide sequence that encodes a cleavable linker so that cleavage at the cleavable linker separates a macromolecule encoded by a nucleic acid inserted into the polylinker insertion site from the remainder of the encoded delivery construct. Thus, in embodiments where the polylinker insertion site is at an end of the encoded construct, the polynucleotide comprises one nucleotide sequence encoding a cleavable linker between the polylinker insertion site and the remainder of the polynucleotide. In embodiments where the polylinker insertion site is not at the end of the encoded construct, the polylinker insertion site can be flanked by nucleotide sequences that each encode a cleavable linker.

In certain embodiments, the recombinant polynucleotides are based on polynucleotides encoding PE, or portions or derivatives thereof. In other embodiments, the recombinant polynucleotides are based on polynucleotides that hybridize to a polynucleotide that encodes PE under stringent hybridization conditions. A nucleotide sequence encoding PE is presented as SEQ ID NO.:3. This sequence can be used to prepare PCR primers for isolating a nucleic acid that encodes any portion of this sequence that is desired. For example, PCR can be used to isolate a nucleic acid that encodes one or more of the functional domains of PE. A nucleic acid so isolated can then be joined to nucleic acids encoding other functional domains of the delivery constructs using standard recombinant techniques.

Other in vitro methods that can be used to prepare a polynucleotide encoding PE, PE domains, or any other functional domain useful in the delivery constructs of the invention include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of PE or a nucleotide encoding a receptor binding domain.

Guidance for using these cloning and in vitro amplification methodologies are described in, for example, U.S. Pat. No. 4,683,195; Mullis et al., 1987, *Cold Spring Harbor Symp. Quant. Biol.* 51:263; and Erlich, ed., 1989, *PCR Technology*, Stockton Press, NY. Polynucleotides encoding a delivery construct or a portion thereof also can be isolated by screening genomic or cDNA libraries with probes selected from the sequences of the desired polynucleotide under stringent, moderately stringent, or highly stringent hybridization conditions.

Construction of nucleic acids encoding the delivery constructs of the invention can be facilitated by introducing an insertion site for a nucleic acid encoding the macromolecule into the construct. In certain embodiments, an insertion site for the macromolecule can be introduced between the nucleotides encoding the cysteine residues of domain Ib. In other embodiments, the insertion site can be introduced anywhere in the nucleic acid encoding the construct so long as the insertion does not disrupt the functional domains encoded thereby. In certain embodiments, the insertion site can be in the ER retention domain.

In more specific embodiments, a nucleotide sequence encoding a portion of the Ib domain between the cysteine-encoding residues can be removed and replaced with a nucleotide sequence that includes a cloning site cleaved by a restriction enzyme. For example, the cloning site can be recognized and cleaved by PstI. In such examples, a polynucleotide encoding macromolecule that is flanked by PstI sequences can be inserted into the vector.

Further, the polynucleotides can also encode a secretory sequence at the amino terminus of the encoded delivery construct. Such constructs are useful for producing the delivery constructs in mammalian cells as they simplify isolation of the immunogen.

Furthermore, the polynucleotides of the invention also encompass derivative versions of polynucleotides encoding a delivery construct. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the delivery construct. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid.

Several site-specific mutations and deletions in chimeric molecules derived from PE have been made and characterized. For example, deletion of nucleotides encoding amino acids 1-252 of PE yields a construct referred to as "PE40." Deleting nucleotides encoding amino acids 1-279 of PE yields a construct referred to as "PE37." See U.S. Pat. No. 5,602,095. In both of these constructs, the receptor binding domain of PE, i.e., domain Ia, has been deleted. Nucleic acids encoding a receptor binding domain can be ligated to these constructs to produce delivery constructs that are targeted to the cell surface receptor recognized by the receptor binding domain. Of course, these recombinant polynucleotides are particularly useful for expressing delivery constructs that have a receptor binding domain that is not domain Ia of PE. The recombinant polynucleotides can optionally encode an amino-terminal methionine to assist in expression of the construct. In certain embodiments, the receptor binding domain can be ligated to the 5' end of the polynucleotide encoding the transcytosis domain.

Other nucleic acids encoding mutant forms of PE that can be used as a source of nucleic acids for constructing the delivery constructs of the invention include, but are not limited to, PEA553 and those described in U.S. Pat. Nos. 5,602,095; 5,512,658 and 5,458,878, and in Vasil et al., 1986, *Infect. Immunol.* 52:538-48.

Accordingly, in certain embodiments, the invention provides a polynucleotide that encodes a delivery construct. The delivery construct comprises a receptor binding domain, a transcytosis domain, a macromolecule to be delivered to a subject, and a cleavable linker. Cleavage at the cleavable linker can separate the macromolecule from the remainder of the construct. The cleavable linker can be cleaved by an enzyme that is present at a basal-lateral membrane of a polarized epithelial cell of the subject or in the plasma of the subject.

In certain embodiments, the polynucleotide hybridizes under stringent hybridization conditions to any polynucleotide of this invention. In further embodiments, the polynucleotide hybridizes under stringent conditions to a nucleic acid that encodes any delivery construct of the invention.

In certain embodiments, the polynucleotide encodes a delivery construct that further comprises a second cleavable linker. In certain embodiments, the first and/or second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10). In certain embodiments, the first and/or second cleavable linker encoded by the polynucleotide is cleavable by an enzyme that is selected from the group consisting of Cathepsin GI, Chymotrypsin I, Elastase I, Subtilisin AI, Subtilisin AII, Thrombin I, and Urokinase I.

In certain embodiments, the receptor binding domain encoded by the polynucleotide is selected from the group consisting of receptor binding domains from *Pseudomonas* exotoxin A, cholera toxin, diptheria toxin, shiga toxin, or shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; and IL-8. In certain embodiments, the receptor binding domain encoded by the polynucleotide binds to a cell-surface receptor that is selected from the group consisting of α2-macroglobulin receptor, EGFR, IGFR, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor. In further embodiments, the receptor binding domain encoded by the polynucleotide is Domain Ia of *Pseudomonas* exotoxin A. In yet further embodiments, the receptor binding domain encoded by the polynucleotide has an amino acid sequence that is SEQ ID NO.:1.

In certain embodiments, the transcytosis domain encoded by the polynucleotide is selected from the group consisting of transcytosis domains from *Pseudomonas* exotoxin A, diptheria toxin, pertussis toxin, cholera toxin, heat-labile *E. coli* enterotoxin, shiga toxin, and shiga-like toxin. In further embodiments, the transcytosis domain is *Pseudomonas* exotoxin A transcytosis domain. In still further embodiments, the *Pseudomonas* exotoxin A transcytosis domain has an amino acid sequence that is SEQ ID NO.:2.

In certain embodiments, the macromolecule encoded by the polynucleotide is selected from the group of a peptide, a polypeptide, and a protein. In certain embodiments, the polypeptide is selected from the group consisting of polypeptide hormones, cytokines, chemokines, growth factors, and clotting factors. In further embodiments, the polypeptide is selected from the group consisting of IGF-I, IGF-II, IGF-III, EGF, IFN-α, IFN-β, IFN-γ, G-CSF, GM-CSF, IL-1, IL-2, IL-3, IL-6, IL-8, IL-12, EPO, growth hormone, factor VII, vasopressin, calcitonin, parathyroid hormone, luteinizing hormone-releasing factor, tissue plasminogen activators, adrenocorticototropin, enkephalin, and glucagon-like peptide 1. In still further embodiments, the polypeptide is human growth hormone. In other embodiments, the protein is human insulin.

In other embodiments, the invention provides a polynucleotide that encodes a delivery construct that comprises a nucleic acid sequence encoding a receptor binding domain, a nucleic acid sequence encoding a transcytosis domain, a nucleic acid sequence encoding a cleavable linker, and a nucleic acid sequence comprising a polylinker insertion site. The polylinker insertion site can be oriented relative to the nucleic acid sequence encoding a cleavable linker to allow to cleavage of the cleavable linker to separate a macromolecule that is encoded by a nucleic acid inserted into the polylinker insertion site from the remainder of said delivery construct. The cleavable linker can be cleavable by an enzyme that is present at a basal-lateral membrane of a polarized epithelial cell of said subject or in the plasma of said subject.

5.5. Expression Vectors

In still another aspect, the invention provides expression vectors for expressing the delivery constructs. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning—A Laboratory Manual,* $3^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, N.Y.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the delivery constructs are expressed. Expression vectors useful for expressing delivery constructs include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNAl (Invitrogen, San Diego, Calif.), in which the expression control sequence comprises the CMV promoter, provides good rates of transfection and expression into such cells.

The expression vectors can be introduced into the cell for expression of the delivery constructs by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology, vol.* 185, Academic Press, Inc., CA; Krieger, 1990, *Gene Transfer and Expression—A Laboratory Manual*, Stockton Press, NY;

Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, N.Y.

The expression vectors can also contain a purification moiety that simplifies isolation of the delivery construct. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the delivery construct following purification. In other embodiments, the moiety does not interfere with the function of the functional domains of the delivery construct and thus need not be cleaved.

5.6. Cell for Expressing a Delivery Construct

In yet another aspect, the invention provides a cell comprising an expression vector for expression of the delivery constructs, or portions thereof. The cell is preferably selected for its ability to express high concentrations of the delivery construct to facilitate purification of the protein. In certain embodiments, the cell is a prokaryotic cell, for example, *E. coli*. As described in the examples, the delivery constructs are properly folded and comprise the appropriate disulfide linkages when expressed in *E. coli*.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the delivery constructs. For example, Chinese hamster ovary (CHO) cells can be used to express the delivery constructs.

5.7. Compositions Comprising Delivery Constructs

The delivery constructs of the invention can be formulated as compositions. The compositions are generally formulated appropriately for the immediate use intended for the delivery construct. For example, if the delivery construct is not to be administered immediately, the delivery construct can be formulated in a composition suitable for storage. One such composition is a lyophilized preparation of the delivery construct together with a suitable stabilizer. Alternatively, the delivery construct composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the delivery constructs may be found, for example, in U.S. Pat. Nos. 6,573,237, 6,525,102, 6,391,296, 6,255,284, 6,133, 229, 6,007,791, 5,997,856, and 5,917,021.

Further, the delivery construct compositions of the invention can be formulated for administration to a subject. Such vaccine compositions generally comprise one or more delivery constructs of the invention and a pharmaceutically acceptable excipient, diluent, carrier, or vehicle. Any such pharmaceutically acceptable excipient, diluent, carrier, or vehicle known to one of skill in the art without limitation can be used. Examples of a suitable excipient, diluent, carrier, or vehicle can be found in *Remington's Pharmaceutical Sciences*, 21st Ed. 2005, Mack Publishing Co., Easton.

In certain embodiments, the delivery construct compositions are formulated for oral administration. In such embodiments, the compositions are formulated to protect the delivery construct from acid and/or enzymatic degradation in the stomach. Upon passage to the neutral to alkaline environment of the duodenum, the delivery construct then contacts a mucous membrane and is transported across the polarized epithelial membrane. The delivery constructs may be formulated in such compositions by any method known by one of skill in the art, without limitation.

In certain embodiments, the oral formulation comprises a delivery construct and one or more compounds that can protect the delivery construct while it is in the stomach. For example, the protective compound should be able to prevent acid and/or enzymatic hydrolysis of the delivery construct. In certain embodiments, the oral formulation comprises a delivery construct and one or more compounds that can facilitate transit of the construct from the stomach to the small intestine. In certain embodiments, the one or more compounds that can protect the delivery construct from degradation in the stomach can also facilitate transit of the construct from the stomach to the small intestine. Preferably, the oral formulation comprises one or more compounds that can protect the delivery construct from degradation in the stomach and facilitate transit of the construct from the stomach to the small intestine. For example, inclusion of sodium bicarbonate can be useful in facilitating the rapid movement of intra-gastric delivered materials from the stomach to the duodenum as described in Mrsny et al., 1999, *Vaccine* 17:1425-1433.

Other methods for formulating compositions so that the delivery constructs can pass through the stomach and contact polarized epithelial membranes in the small intestine include, but are not limited to, enteric-coating technologies as described in DeYoung, 1989, *Int J Pancreatol.* 5 Suppl:31-6, and the methods provided in U.S. Pat. Nos. 6,613,332, 6,174, 529, 6,086,918, 5,922,680, and 5,807,832.

5.7.1. Kits Comprising Compositions

In yet another aspect, the invention provides a kit that comprises a composition of the invention. In certain embodiments, the kit further comprises instructions that direct administration of the composition to a mucous membrane of the subject to whom the composition is administered. In certain embodiments, the kit further comprises instructions that direct oral administration of the composition to the subject to whom the composition is administered.

In certain embodiments, the kit comprises a composition of the invention in more or more containers. In certain embodiments, the composition can be in a unit dosage form, e.g., a tablet, lozenge, capsule, etc. In certain embodiments, the composition can be provided in or with a device for administering the composition, such as, for example, a device configured to administer a single-unit dose of the composition, e.g., an inhaler.

5.8. Making and Testing Delivery Constructs

The delivery constructs of the invention are preferably produced recombinantly, as described below. However, the delivery constructs may also be produced by chemical synthesis using methods known to those of skill in the art.

5.8.1. Manufacture of Delivery Constructs

Methods for expressing and purifying the delivery constructs of the invention are described extensively in the examples below. Generally, the methods rely on introduction of an expression vector encoding the delivery construct to a cell that can express the delivery construct from the vector.

The delivery construct can then be purified for administration to a subject.

5.8.2. Testing Delivery Constructs

Having selected the domains of the delivery construct, the function of these domains, and of the delivery constructs as a whole, can be routinely tested to ensure that the constructs can deliver a macromolecule across mucous membranes of a subject free from the remainder of the construct. For example, the delivery constructs can be tested for cell recognition, transcytosis and cleavage using routine assays. The entire chimeric protein can be tested, or, the function of various domains can be tested by substituting them for native domains of the wild-type toxin.

5.8.2.1. Receptor Binding/Cell Recognition

Receptor binding domain function can be tested by monitoring the delivery construct's ability to bind to the target receptor. Such testing can be accomplished using cell-based assays, with the target receptor present on a cell surface, or in cell-free assays. For example, delivery construct binding to a target can be assessed with affinity chromatography. The construct can be attached to a matrix in an affinity column, and binding of the receptor to the matrix detected, or vice versa. Alternatively, if antibodies have been identified that bind to either the receptor binding domain or its cognate receptor, the antibodies can be used, for example, to detect the receptor binding domain in the delivery construct by immunoassay, or in a competition assay for the cognate receptor. An exemplary cell-based assay that detects delivery construct binding to receptors on cells comprises labeling the construct and detecting its binding to cells by, e.g., fluorescent cell sorting, autoradiography, etc.

5.8.2.2. Transcytosis

The function of the transcytosis domain can be tested as a function of the delivery construct's ability to pass through an epithelial membrane. Because transcytosis first requires binding to the cell, these assays can also be used to assess the function of the cell recognition domain.

The delivery construct's transcytosis activity can be tested by any method known by one of skill in the art, without limitation. In certain embodiments, transcytosis activity can be tested by assessing the ability of a delivery construct to enter a non-polarized cell to which it binds. Without intending to be bound to any particular theory or mechanism of action, it is believed that the same property that allows a transcytosis domain to pass through a polarized epithelial cell also allows molecules bearing the transcytosis domain to enter non-polarized cells. Thus, the delivery construct's ability to enter the cell can be assessed, for example, by detecting the physical presence of the construct in the interior of the cell. For example, the delivery construct can be labeled with, for example, a fluorescent marker, and the delivery construct exposed to the cell. Then, the cells can be washed, removing any delivery construct that has not entered the cell, and the amount of label remaining determined. Detecting the label in this fraction indicates that the delivery construct has entered the cell.

In other embodiments, the delivery construct's transcytosis ability can be tested by assessing the delivery construct's ability to pass through a polarized epithelial cell. For example, the delivery construct can be labeled with, for example, a fluorescent marker and contacted to the apical membranes of a layer of epithelial cells. Fluorescence detected on the basal-lateral side of the membrane formed by the epithelial cells indicates that the transcytosis domain is functioning properly.

5.8.2.3. Cleavable Linker Cleavage

The function of the cleavable linker can generally be tested in a cleavage assay. Any suitable cleavage assay known by one of skill in the art, without limitation, can be used to test the cleavable linkers. Both cell-based and cell-free assays can be used to test the ability of an enzyme to cleave the cleavable linkers.

An exemplary cell-free assay for testing cleavage of cleavable linkers comprises preparing extracts of polarized epithelial cells and exposing a labeled delivery construct bearing a cleavable linker to the fraction of the extract that corresponds to membrane-associated enzymes. In such assays, the label can be attached to either the macromolecule to be delivered or to the remainder of the delivery construct. Among these enzymes are cleavage enzymes found near the basal-lateral membrane of a polarized epithelial cell, as described above. Cleavage can be detected, for example, by binding the delivery construct with, for example, an antibody and washing off unbound molecules. If label is attached to the macromolecule to be delivered, then little or no label should be observed on the molecule bound to the antibodies. Alternatively, the binding agent used in the assay can be specific for the macromolecule, and the remainder of the construct can be labeled. In either case, cleavage can be assessed.

Cleavage can also be tested using cell-based assays that test cleavage by polarized epithelial cells assembled into membranes. For example, a labeled delivery construct, or portion of a delivery construct comprising the cleavable linker, can be contacted to either the apical or basolateral side of a monolayer of suitable epithelial cells, such as, for example, Coco-2 cells, under conditions that permit cleavage of the linker. Cleavage can be detected by detecting the presence or absence of the label using a reagent that specifically binds the delivery construct, or portion thereof. For example, an antibody specific for the delivery construct can be used to bind a delivery construct comprising a label distal to the cleavable linker in relation to the portion of the delivery construct bound by the antibody. Cleavage can then be assessed by detecting the presence of the label on molecules bound to the antibody. If cleavage has occurred, little or no label should be observed on the molecules bound to the antibody. By performing such experiments, enzymes that preferentially cleave at the basolateral membrane rather than the apical membrane can be identified, and, further, the ability of such enzymes to cleave the cleavable linker in a delivery construct can be confirmed.

Further, cleavage can also be tested using a fluorescence reporter assay as described in U.S. Pat. No. 6,759,207. Briefly, in such assays, the fluorescence reporter is contacted to the basolateral side of a monolayer of suitable epithelial cells under conditions that allow the cleaving enzyme to cleave the reporter. Cleavage of the reporter changes the structure of the fluorescence reporter, changing it from a non-fluorescent configuration to a fluorescent configuration. The amount of fluorescence observed indicates the activity of the cleaving enzyme present at the basolateral membrane.

Further, cleavage can also be tested using an intra-molecularly quenched molecular probe, such as those described in U.S. Pat. No. 6,592,847. Such probes generally comprise a fluorescent moiety that emits photons when excited with light of appropriate wavelength and a quencher moiety that absorbs such photons when in close proximity to the fluorescent moiety. Cleavage of the probe separates the quenching moiety from the fluorescent moiety, such that fluorescence can be detected, thereby indicating that cleavage has occurred. Thus, such probes can be used to identify and assess cleavage by particular cleaving enzymes by contacting the basolateral side of a monolayer of suitable epithelial cells with the probe under conditions that allow the cleaving enzyme to cleave the probe. The amount of fluorescence observed indicates the activity of the cleaving enzyme being tested.

6. EXAMPLES

The following examples merely illustrate the invention, and are not intended to limit the invention in any way.

6.1. Construction of a Delivery Construct

Five exemplary delivery construct expression vectors for delivering rat growth hormone (rGH) were constructed according to the following protocol. First, the rGH gene was amplified by PCR, incorporating restriction enzymes pairs of NdeI and EcoRI, PstI and PstI, AgeI and EcoRI, or PstI and EcoRI sites at two ends of the PCR products. After restriction enzyme digestion, the PCR products were cloned into pPE64-PstI-Δ553, which was digested with the corresponding restriction enzyme pairs. The resulting constructs were named as pPE-RGH(NdeI-EcoRI), pntPE-RGH(PstI), pntPE-RGH(AgeI-EcoRI), and pPE-RGH(PstI-EcoRI). These constructs thus comprise sequences encoding Domains I and II of ntPE (amino acids 26-372 as shown in FIG. 3) and rGH (Accession No. P01244; see Seeburg et al., 1977, Nature 270:486-494 and Page et al., 1981, Nucleic Acids Res. 9:2087-2104), and are also tagged with a 6-His motif at the N-terminus of the polypeptide to facilitate purification. The final plasmids were verified by restriction enzyme digestions and DNA sequencing.

Expression vectors comprising cleavable linkers were constructed by introducing sequences encoding the appropriate amino acid sequence. To do so, oligonucleotides that encode sequences complementary to appropriate restriction sites and one of the following amino acid sequences were synthesized, then ligated into an expression vector prepared as described above between the ntPE sequences and the rGH sequences. For Delivery Construct 1, the cleavable linker sequence was RQPRGGL. For Delivery Construct 2, the cleavable linker sequence was GGLRQPR. For Delivery Construct 3, the cleavable linker sequence was RQPREGR. For Delivery Construct 4, the cleavable linker sequence was RQPRVGR. For Delivery Construct 5, the cleavable linker sequence was RQPRARR.

To separate rGH from PE protein in the event that the fusion protein is taken up by antigen presenting cells, a protease furin site was also inserted between the cleavable linker and rGH. To do so, constructs containing a sequence encoding the furin site with the five different cleavable linkers were made. Oligonucleotide sequences for the five cleavable linkers and a furin clip site are shown in Table 3 below. Each of the oligo duplexes was inserted into PstI site of pPE-RGH(PstI-EcoRI). The final constructs, named as pPE-RGH-F1, pPE-RGH-F2, pPE-RGH-F3, pPE-RGH-F4, pPE-RGH-F5 were confirmed by restriction enzyme digestion and DNA sequencing.

TABLE 3

Oligonucleotide pairs for introducing a furin cleavage site and protease cleavage site pPE-RGH-1  1 F: AACTGCAGCGCCAGCCTCGAG (SEQ ID NO:24)
              GAGGATTACTGCAGAA
           1 R: TTCTGCAGTAATCCTCCTCGA (SEQ ID NO:25)
              GGCTGGCGCTGCAGTT pPE-RGH-2  2 F: AACTGCAGGGAGGCTTACGCC (SEQ ID NO:26)
              AGCCTCGACTGCAGAA TABLE 3-continued Oligonucleotide pairs for introducing a furin cleavage site and protease cleavage site

2 R: TTCTGCAGTCGAGGCTGGCGT (SEQ ID NO:27)
              AAGCCTCCCTGCAGTT pPE-RGH-3  3 F: AACTGCAGCGCCAGCCTCGAG (SEQ ID NO:28)
              AGGGCCGTCTGCAGAA
           3 R: TTCTGCAGACGGCCCTCTCGA (SEQ ID NO:29)
              GGCTGGCGCTGCAGTT pPE-RGH-4  4 F: AACTGCAGCGCCAGCCTCGAG (SEQ ID NO:30)
              TCGGCCGTCTGCAGAA
           4 R: TTCTGCAGACGGCCGACTCGA (SEQ ID NO:31)
              GGCTGGCGCTGCAGTT pPE-RGH-5  5 F: AACTGCAGCGCCAGCCTCGAG (SEQ ID NO:32)
              CACGTCGTCTGCAGAA
           5 R: TTCTGCAGACGACGTGCTCGA (SEQ ID NO:33)
              GGCTGGCGCTGCAGTT

6.2. Expression of Delivery Constructs

*E. coli* BL21(DE3) pLysS competent cells (Novagen, Madison, Wis.) were transformed using a standard heat-shock method in the presence of the appropriate plasmid to generate ntPE-rat Growth Hormone (rGH) expression cells, selected on ampicillin-containing media, and isolated and grown in Luria-Bertani broth (Difco; Becton Dickinson, Franklin Lakes, N.J.) with antibiotic, then induced for protein expression by the addition of 1 mM isopropyl-D-thiogalactopyranoside (IPTG) at OD 0.6. Two hours following IPTG induction, cells were harvested by centrifugation at 5,000 rpm for 10 min. Inclusion bodies were isolated following cell lysis and proteins were solubilized in the buffer containing 100 mM Tris_HCl (pH 8.0), 2 mM EDTA, 6 M guanidine HCl, and 65 mM dithiothreitol. Solubilized His ntPE-rGH is refolded in the presence of 0.1 M Tris, pH=7.4, 500 mM L-arginine, 0.9 mM GSSG, 2 mM EDTA. The refolded proteins were purified by Q sepharose Ion Exchange and Superdex 200 Gel Filtration chromatography (Amersham BioSciences, Inc., Sweden). The purity of proteins was assessed by SDS-PAGE and analytic HPLC (Agilent, Inc. Palo Alto, Calif.).

6.3. Characterization of a Delivery Construct

The following procedures can be used to assess proper refolding of a delivery construct. The protein refolding process is monitored by measuring, e.g., Delivery Construct 1 binding activity with ntPE binding receptor, CD 91 receptors, and rGH binding proteins on a Biacore SPR instrument (Biacore, Sweden) according to the manufacturer's instructions. Proper refolding of other macromolecules in exemplary constructs can be tested in similar binding assays with appropriate binding agents. By testing such binding affinities, the skilled artisan can assess the proper folding of each portion of the delivery construct.

6.4. Delivery Construct Cleavage Assays

This example describes experiments performed to identify and verify enzymes that can be used to cleave the cleavable linkers of the delivery constructs described herein. First, Caco-2 (ATCC Accession No. HTB-37) cells in passage 21 were obtained from American Type Culture Collection (Manassas, Va.). Human tracheal epithelial (HTE) cells were obtained from J. Whiddecombe of the Department of Physiology at the University of California, Davis Medical School. Caco-2 cells were routinely grown on 75 $cm^2$ plastic culture flasks (Becton Dickinson, Franklin Lakes, N.J.) in DMEM containing 10% fetal bovine serum and 1% penicillin-streptomycin at 37° C. in a 5% $CO_2$/95% air atmosphere. HTE cells were grown as described in Yamaya et al., 1992, *Am J Physiol.* 262(6 Pt 1):L713-24.

To identify suitable cleavable linkers, HTE or Caco-2 cells were seeded at a density of $5 \times 10^4$ cells/cm² onto 24-well collagen-coated polycarbonate transwell filters (Corning, Acton, Mass.) for 12-14 days. Confluent monolayers achieved a transepithelial resistance (TER) of >500 ohm cm², as measured using an EVOM epithelial voltohmmeter and STX2 electrode (World Precision Instruments, Sarasota, Fla.). To determine specific enzyme activity, substrates specific for the tested peptidase (500 μM or 1 mM substrate in 250 μl DMEM without FBS or antibiotics) were added to either the apical (AP) or basolateral (BL) side of the monolayers. Peptidase substrates were obtained from Calbiochem, Inc. (Division of EMD Biosciences, Inc., San Diego, Calif.). Cells were incubated for 2 hrs at 37° C. in a 5% $CO_2$/95% air atmosphere. Both the apical and basolateral media was then measured for its specific enzyme activity according to the manufacturer's instruction. Cleavage was assessed by detecting fluorescence of the substrates, which reflects cleavage because it separates of the quenching agent from the fluorescent agent present on the substrate, which separation allows fluorescence to be detected.

Table 4 presents a summary of the results of these assays using HTE cells, while Table 5 presents a summary of the results of these assays using Caco-2 cells. For all results, baseline control values were subtracted from substrate values before percentages were determined and tests were performed at least in duplicate. The percentages presented in the tables represent the percent increase observed in assay in the apical or basolateral media, which depends on which side of the membrane exhibits higher peptidase activity. It should be noted that, even when substrate was added to the media on the apical side of the membrane, peptidase activity can be observed on the basolateral side of the membrane because of diffusion of the substrate across the membrane.

TABLE 4

| Peptidase tested in HTE cells | % AP > BL | % BL > AP | AP A405 nm | BL A405 nm |
|---|---|---|---|---|
| AP-500 uM Cathepsin B I | 86% | | 0.37 | 0.20 |
| BL-500 uM Cathepsin B I | 64% | | 0.35 | 0.21 |
| AP-500 uM Cathepsin G I | 882% | | 0.04 | 0.004 |
| BL-500 uM Cathepsin G I | 6% | | 0.02 | 0.02 |
| AP-500 uM Cathepsin G II | 371% | | 0.02 | 0.01 |
| BL-500 uM Cathepsin G II | 0% | 0% | 0.02 | 0.02 |
| AP-500 uM Cathepsin G III | | 11% | 0.02 | 0.02 |
| BL-500 uM Cathepsin G III | | 400% | 0.01 | 0.03 |
| AP-500 uM Chymotrypsin I | 74% | | 0.04 | 0.02 |
| BL-500 uM Chymotrypsin I | | 36% | 0.03 | 0.04 |
| AP-500 uM Elastase I | 49% | | 0.05 | 0.03 |
| BL-500 uM Elastase I | | 23% | 0.02 | 0.03 |
| AP-500 uM Elastase II | 43% | | 0.29 | 0.20 |
| BL-500 uM Elastase II | 31% | | 0.18 | 0.13 |
| AP-500 uM Elastase III | 89% | | 0.04 | 0.02 |
| BL-500 uM Elastase III | 967% | | 0.03 | 0.003 |
| AP-500 uM Elastase IV | 84% | | 0.35 | 0.19 |
| BL-500 uM Elastase IV | 65% | | 0.23 | 0.14 |
| AP-500 uM Elastase VIII | 529% | | 0.16 | 0.03 |
| BL-500 uM Elastase VIII | 181% | | 0.09 | 0.03 |
| AP-500 uM Papain | 57% | | 0.02 | 0.02 |
| BL-500 uM Papain | 5% | | 0.03 | 0.03 |
| AP-500 uM Subtilisin A I | | 9% | 0.02 | 0.02 |
| BL-500 uM Subtilisin A I | | 3000% | 0.001 | 0.03 |
| AP-500 uM Subtilisin A II | 21% | | 0.02 | 0.02 |
| BL-500 uM Subtilisin A II | | 55% | 0.01 | 0.02 |
| AP-500 uM Thrombin I | 42% | | 0.15 | 0.11 |
| BL-500 uM Thrombin I | | 15% | 0.09 | 0.10 |
| AP-500 uM Thrombin II | 445% | | 0.40 | 0.07 |
| BL-500 uM Thrombin II | 741% | | 0.41 | 0.05 |
| AP-500 uM Urokinase I | 8% | | 0.11 | 0.10 |
| BL-500 uM Urokinase I | | 4% | 0.13 | 0.13 |
| AP-1 mM Cathepsin B I | 17% | | 0.18 | 0.15 |
| BL-1 mM Cathepsin B I | 42% | | 0.24 | 0.17 |
| AP-1 mM Cathepsin G I | 114% | | 0.05 | 0.02 |
| BL-1 mM Cathepsin G I | | 47% | 0.02 | 0.03 |
| AP-1 mM Cathepsin G II | 138% | | 0.05 | 0.02 |
| BL-1 mM Cathepsin G II | 19% | | 0.03 | 0.03 |
| AP-1 mM Cathepsin G III | 225% | | 0.07 | 0.02 |
| BL-1 mM Cathepsin G III | | 54% | 0.02 | 0.03 |
| AP-1 mM Chymotrypsin I | 35% | | 0.06 | 0.04 |
| BL-1 mM Chymotrypsin I | | 90% | 0.04 | 0.07 |
| AP-1 mM Elastase I | | 108% | 0.02 | 0.03 |
| BL-1 mM Elastase I | | 864% | 0.01 | 0.09 |
| AP-1 mM Elastase II | 62% | | 0.28 | 0.17 |
| BL-1 mM Elastase II | 42% | | 0.33 | 0.23 |
| AP-1 mM Elastase III | 318% | | 0.02 | 0.01 |
| BL-1 mM Elastase III | 131% | | 0.04 | 0.02 |
| AP-1 mM Elastase IV | 94% | | 0.41 | 0.21 |
| BL-1 mM Elastase IV | 61% | | 0.30 | 0.19 |
| AP-1 mM Elastase VIII | 233% | | 0.14 | 0.04 |
| BL-1 mM Elastase VIII | 41% | | 0.06 | 0.05 |
| AP-1 mM Papain | 424% | | 0.02 | 0.004 |
| BL-1 mM Papain | 141% | | 0.02 | 0.01 |
| AP-1 mM Subtilisin A I | 18% | | 0.03 | 0.03 |
| BL-1 mM Subtilisin A I | | 290% | 0.01 | 0.04 |
| AP-1 mM Subtilisin A II | 17% | | 0.03 | 0.02 |
| BL-1 mM Subtilisin A II | | 318% | 0.01 | 0.04 |
| AP-1 mM Thrombin I | 27% | | 0.17 | 0.14 |
| BL-1 mM Thrombin I | 28% | | 0.17 | 0.13 |
| AP-1 mM Thrombin II | 20% | | 0.12 | 0.10 |
| BL-1 mM Thrombin II | | 13% | 0.05 | 0.06 |
| AP-1 mM Urokinase I | | 14% | 0.19 | 0.21 |
| BL-1 mM Urokinase I | 4% | | 0.21 | 0.20 |

TABLE 5

| Peptidase tested in Caco-2 cells | % AP > BL | % BL > AP | AP A405 nm | BL A405 nm |
|---|---|---|---|---|
| AP-500 uM Cathepsin B I | 150% | | 0.14 | 0.06 |
| BL-500 uM Cathepsin B I | 34% | | 0.17 | 0.12 |
| AP-10 mM Cathepsin G I | 195% | | 0.31 | 0.10 |
| BL-10 mM Cathepsin G I | | 145% | 0.42 | 1.03 |
| AP-500 uM Cathepsin G III | 35% | | 0.014 | 0.01 |
| BL-500 uM Cathepsin G III | 185% | | 0.03 | 0.01 |
| AP-500 uM Cathepsin G I | 232% | | 0.05 | 0.01 |
| BL-500 uM Cathepsin G I | | 1709% | 0.01 | 0.15 |
| AP-500 uM Cathepsin G II | 3900% | | 0.01 | 0.0003 |
| BL-500 uM Cathepsin G II | | 1330% | 0.003 | 0.04 |
| AP-500 uM Chymotrypsin I | | 342% | 0.01 | 0.04 |
| BL-500 uM Chymotrypsin I | | 403% | 0.03 | 0.16 |
| AP-500 uM Elastase I | 73% | | 0.01 | 0.01 |
| BL-500 uM Elastase I | 295% | | 0.04 | 0.01 |
| AP-500 uM Elastase II | 59% | | 0.12 | 0.07 |
| BL-500 uM Elastase II | | 89% | 0.01 | 0.02 |
| AP-500 uM Elastase III | 85% | | 0.01 | 0.07 |
| BL-500 uM Elastase III | | 320% | 0.003 | 0.01 |
| AP-500 uM Elastase IV | 32% | | 0.11 | 0.08 |
| BL-500 uM Elastase IV | | 12% | 0.02 | 0.02 |
| AP-500 uM Elastase VIII | | 16% | 0.02 | 0.02 |
| BL-500 uM Elastase VIII | | 115% | 0.01 | 0.02 |
| AP-500 uM Papain | | 19% | 0.018 | 0.02 |
| BL-500 uM Papain | 339% | | 0.07 | 0.02 |
| AP-500 uM Subtilisin A I | | ***23% | — | 0.05 |
| BL-500 uM Subtilisin A I | | ***94% | — | 0.20 |
| AP-500 uM Subtilisin A II | N/A | | — | — |
| BL-500 uM Subtilisin A II | | ***11% | — | 0.02 |
| AP-500 uM Thrombin I | 81% | | 0.04 | 0.02 |
| BL-500 uM Thrombin I | | 254% | 0.01 | 0.04 |

TABLE 5-continued

| Peptidase tested in Caco-2 cells | % AP > BL | % BL > AP | AP A405 nm | BL A405 nm |
|---|---|---|---|---|
| AP-Thrombin II 500 uM | 42% | | 0.08 | 0.06 |
| BL-Thrombin II 500 uM | 62% | | 0.09 | 0.06 |
| AP-500 uM Urokinase I | 111% | | 0.12 | 0.06 |
| BL-500 uM Urokinase I | | 1044% | 0.005 | 0.05 |
| AP-1 mM Cathepsin B I | 109% | | 0.27 | 0.13 |
| BL-1 mM Cathepsin B I | | 58% | 0.12 | 0.2 |
| AP-20 mM Cathepsin G I | | 129% | 0.10 | 0.23 |
| BL-20 mM Cathepsin G I | | 540% | 0.11 | 0.70 |
| AP-1 mM Cathepsin G III | 37% | | 0.01 | 0.01 |
| BL-1 mM Cathepsin G III | 103% | | 0.07 | 0.03 |
| AP-1 mM Cathepsin G I | 107% | | 0.08 | 0.04 |
| BL-1 mM Cathepsin G I | 144% | | 0.12 | 0.05 |
| AP-1 mM Cathepsin G II | | 11% | 0.05 | 0.06 |
| BL-1 mM Cathepsin G II | | 7850% | 0.00 | 0.04 |
| AP-1 mM Chymotrypsin I | 107% | | 0.08 | 0.04 |
| BL-1 mM Chymotrypsin I | | 288% | 0.02 | 0.07 |
| AP-1 mM Elastase I | 217% | | 0.03 | 0.001 |
| BL-1 mM Elastase I | | 880% | 0.003 | 0.02 |
| AP-1 mM Elastase II | 27% | | 0.17 | 0.14 |
| BL-1 mM Elastase II | | 34% | 0.02 | 0.03 |
| AP-1 mM Elastase III | 192% | | 0.02 | 0.01 |
| BL-1 mM Elastase III | 77% | | 0.02 | 0.01 |
| AP-1 mM Elastase IV | 42% | | 0.16 | 0.11 |
| BL-1 mM Elastase IV | | 10% | 0.04 | 0.05 |
| AP-1 mM Elastase VIII | 70% | | 0.05 | 0.03 |
| BL-1 mM Elastase VIII | 332% | | 0.11 | 0.03 |
| AP-1 mM Papain | 61% | | 0.02 | 0.01 |
| BL-1 mM Papain | | 0% | 0.005 | 0.005 |
| AP-1 mM Subtilisin A I | | ***61% | — | 0.13 |
| BL-1 mM Subtilisin A I | | ***44% | — | 0.09 |
| AP-1 mM Subtilisin A II | N/A | | — | — |
| BL-1 mM Subtilisin A II | N/A | | — | — |
| AP-1 mM Thrombin I | 420% | | 0.11 | 0.02 |
| BL-1 mM Thrombin I | | 3400% | 0.005 | 0.16 |
| AP-Thrombin II 1 mM | 163% | | 0.14 | 0.05 |
| BL-Thrombin II 1 mM | 29% | | 0.11 | 0.09 |
| AP-1 mM Urokinase I | 57% | | 0.17 | 0.11 |
| BL-1 mM Urokinase I | | 230% | 0.05 | 0.15 |

***denotes % over baseline control only
"—" denotes values below baseline control

6.5. Delivery of an Exemplary Macromolecule—Green Fluorescent Protein

The following example describes experiments performed to assess the transcytosis of an exemplary delivery construct for delivering green fluorescent protein ("GFP") across a mouse epithelial membrane. It is noted that this exemplary delivery construct does not comprise a cleavable linker; however, the presence or absence of the cleavable linker should not affect transcytosis of the delivery construct.

Briefly, a nt-PE-GFP construct was applied to the trachea of anesthetized female balb/c mice which were approximately 8 weeks of age. The mice were anesthetized with inhaled isoflurane and the trachea was exposed. A small hole was made on the trachea to allow application of our GFP material. In our experiments, 100 μg of GFP alone or ntPE-GFP was used, respectively. The GFP material was slowly dripped directly onto the exposed trachea in a 100 μl volume. After 15 minutes, the mice were euthanized by $CO_2$ asphyxiation. The trachea was removed and frozen in OCT (cat#25608-930-Tissue Tek) using biopsy cryomolds (cat#4565-Tissue Tek). The samples were sectioned onto slides and visualized by fluorescence microscopy (Nikon model Eclipse E400).

Figure 1D:
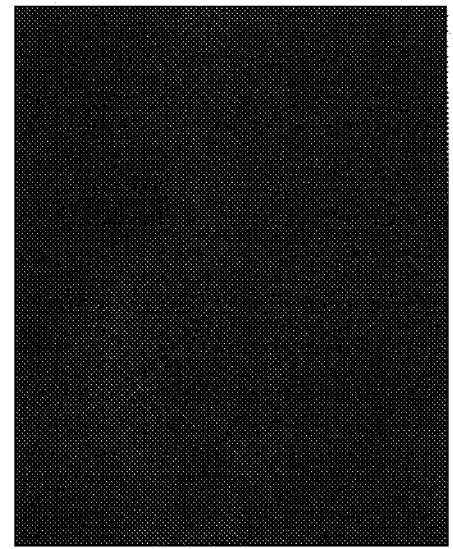
Figure 1A:
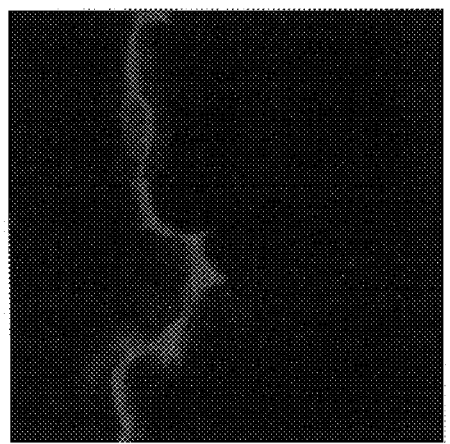
Figure 1C:
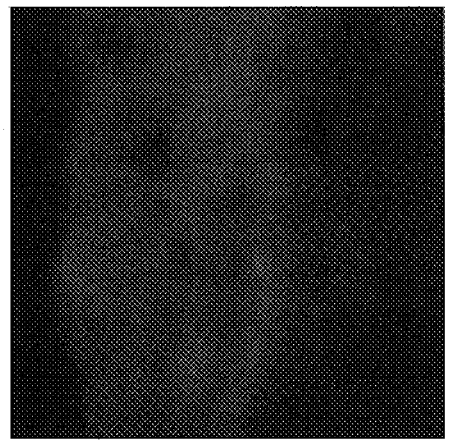

Micrographs of the epithelial sections are presented as FIGS. 1A-1C. FIG. 1A shows the nt-PE-GFP construct adhering strongly to the apical surface of the trachea epithelium. FIG. 1B shows transcytosis of the nt-PE-GFP construct across the trachea epithelium. FIG. 1C shows release of the nt-PE-GFP construct from the basolateral side of the trachea epithelium. FIG. 1D presents a micrograph of a negative control, a tracheal epithelial section from a mouse contacted with GFP alone. The tissues exposed for 15 minutes to obtain these micrographs.

The micrographs demonstrate that nt-PE-GFP interacts strongly with receptors on the apical surface of mouse tracheal epithelium, transcytoses across such epithelial tissue, and releases from the basolateral surface of the mouse tracheal epithelium.

In addition, plasma concentrations of the nt-PE-GFP construct were determined following administration of the delivery construct using an ELISA assay as described in Example 6.6.1, below. Serum samples were taken from anesthetized mice that had received intranasal administration of 100 μg of the nt-PE-GFP delivery construct every 30 minutes following administration. FIG. 2 presents the results of this experiment, demonstrating that peak plasma levels of the delivery construct reached between 500-900 ng/ml, indicating that the delivery construct displayed approximately 22% bioavailability following intranasal administration.

6.6. Detection of Growth Hormone Protein in Tissue by Histological Examination This example describes histological detection in tissues of a representative macromolecule for delivery, growth hormone. Following administration of a delivery construct, animals are euthanized by $CO_2$ asphyxiation and exanguinated by cardiac puncture. Specific tissues (lymph nodes, trachea, brain, spleen liver, GI tract) are removed, briefly rinsed in PBS to remove any residual blood and frozen in OCT. Sections (5 microns thick) are placed onto slides. Slides are fixed in acetone for 10 min and rinsed with PBS. Slides are incubated with 3% peroxidase for 5 min. Slides are then blocked with protein for an additional 5 min. Primary growth hormone antibody is incubated onto slides for 30 min at a 1:100 dilution followed by PBS washes. Biotin-labeled secondary antibody is then incubated for approximately 15 minutes followed by PBS washes. Streptavidin HRP label is incubated onto slides for 15 min followed by PBS washes. HRP Chromagen is applied for 5 min followed by several rinses in distilled $H_2O$. Finally, the slides are counterstained with hematoxylin for 1 min, coverslipped, and examined for the presence of GH.

6.7. Transport and Cleavage of an Exemplary Delivery Construct in an In Vitro System This example describes transport and cleavage of an exemplary delivery construct, Delivery Construct 2, comprising rat growth hormone (rGH) in an in vitro system using human tracheal epithelial cells.

6.7.1. Growth of Human Tracheal Epithelial Cells

Human tracheal epithelial (HTE) cells were isolated from tracheas as previously described and cultured on semi-permeable filter systems (0.45 um pore size; Corning, Acton, Mass.) coated with human placental collagen. See Yamaya et al., 1992, *Am J Physiol*, 262:L713-24 and Sachs et al., 2003, *In Vitro Cell Dev Biol Anim*, 39:56-62. Cell sheets were used at >10 days following plating, at which time they had a transepithelial resistance (TER) of >100 Ω·ohms·cm² as measured with a "chopstick" voltohmeter (Millicell ERS, Manassas, Va.).

Caco-2 cells in passage 21 were obtained from American Type Culture Collection (Manassas, Va.). Cells were routinely grown on 75 cm² plastic culture flasks (Becton Dickinson, Franklin Lakes, N.J.) in DMEM containing 10% fetal bovine serum (FBS) and 1% penicillin-streptomycin at 37° C. in a 5% $CO_2$/95% air atmosphere. For the transport and cleavage studies, Caco-2 cells were seeded at a density of $5 \times 10^4$ cells/cm$^2$ onto 24-well collagen-coated polycarbonate transwell filters (Corning, Acton Mass.) for 12-14 days. Confluent monolayers achieved a transepithelial resistance (TER) of >500 ohm·cm$^2$, as measured using the EVOM and STX2 electrode (World Precision Instruments).

6.7.2. Transport and Cleavage Assays

To determine transport and cleavage activity, Delivery Constructs 1 and 2 proteins (10 µg in 100 µl DMEM without phenol red, FBS or antibiotics) were added to the apical side of the epithelial monolayer. Cells were incubated for 4 hrs at 37° C. in a 5% CO$_2$/95% air atmosphere. Both the apical and basolateral media was then assayed for its transport and cleavage activity by testing for the presence of rGH cleaved from the delivery construct by western blot analysis, as described below. As a control, 10 µg of dextran fluorescein was also added to the apical wells in order to check for leakage.

Following the 4 hour incubation described above, apical and basolateral media samples were precipitated by the addition of trichloroacetic acid (TCA). The amount of TCA added to each sample was twenty percent relative to the sample volume. Each sample was vortexed and placed on ice for 30 minutes. After samples this incubation on ice, samples were centrifuged at 14,000 RPM for 10 minutes. Next, the supernatants from each sample were aspirated and tubes containing the remaining pellet were left open to air dry. 4 µl 0.2M NaOH was added to each pellet. Five minutes after the addition of NaOH, pellets were resuspended in 36 µl 8M Urea.

Next, 10 µl Sample Buffer containing DTT (Invitrogen NP0007, NP0009) was added to each sample. Samples were then placed on a 100° C. heating block for 5 minutes. Half (19 µl) of each sample was then loaded on to a 4%-12% Tris Bis Gel (Invitrogen NP3022BOX). For controls, recombinant rat GH (RDI R0125) and Delivery Construct 1 or Delivery Construct 2 proteins were also loaded directly into the gel. Electrophoresis was at 150V for 30 minutes. From the gel, samples were transferred onto nitrocellulose at 30V for 1 hour.

The Blocking Solution, Antibody Diluents, and Antibody Wash Solution from Invitrogen's WesternBreeze were used in subsequent steps. The nitrocellulose membrane was placed in blocking buffer and incubated at 4° C., overnight. The membrane was washed 3 times for 3 minutes each time. The membrane was then incubated at RT with 10 ml of 1:2000 rabbit anti growth hormone (RDI RDIRtGHabr). After one hour, the membrane was again rinsed 3 times for 3 minutes each. Membrane was incubated for 1 hour at room temperature with 10 ml of goat anti rabbit IgG AP (Pierce 31340) at 1:5000. The membrane was rinsed 3 times for 3 minutes per wash. 5 µl of substrate (Pierce 34042) was added to the membrane. After color development reached desired intensity, reaction was halted by the removal of substrate and the addition of purified water. Finally, the membrane was washed in purified water for 30 minutes and air dried.

Results of the Western Blot analysis are presented in FIG. 4. As seen in FIG. 4, media from the basolateral side of the epithelial cell layer contained protein consistent with cleaved rGH separated from the remainder of Delivery Construct 2. In contrast, media from the apical side of the epithelial cell layer contained largely intact delivery construct. Thus, application of Delivery Construct 2 to the apical side of the human epithelial cell membrane resulted in both transport to the basolateral side of the membrane and proper cleavage of the construct as shown by release of rGH detectable with anti-rGH antibody and of proper apparent molecular weight. Similar results were also observed for Delivery Construct 1 (data not shown).

6.8. Delivery of an Exemplary Macromolecule in an In Vivo System

This example describes use of exemplary Delivery Construct 2 in a mouse model, showing effective transport and cleavage of the delivery construct in vivo and the bioactivity of the macromolecule delivered by Delivery Construct 2, rGH.

6.8.1. Administration of a Delivery Construct Comprising Rat Growth Hormone

Using an animal feeding needle, 100 µg of Delivery Construct 2 (in 250 µl total volume) was orally delivered to female BALB/c mice, 5-6 weeks of age (Charles River Laboratories, Wilmington, Mass.). Delivery Construct 2 was diluted in 1 mg/ml bovine serum albumin (BSA) and phosphate buffered saline (PBS). As a positive control, control mice were subcutaneously (SC) injected on their dorsal side with 30 µg of recombinant rat growth hormone (rGH) diluted in PBS (100 µl total volume). At specific times after oral gavage and SC administration, mice were euthanized by CO$_2$ asphyxiation and exsanguinated. Whole blood and liver were collected and analyzed as described below. Because in the difference in molecular weights between Delivery Construct 2 and rGH, essentially the same number of rGH molecules were administered in both routes.

6.8.2. Pharmacokinetics of an Exemplary Macromolecule Administered with a Delivery Construct in an In Vivo System To assess the pharmacokinetics of an exemplary macromolecule delivered with a delivery construct, ELISA assays were used to measure serum concentrations of rGH at defined timepoints following administration. The serum concentration data thus obtained was used to compare the pharmacokinetics of rGH administered with Delivery Construct 2 to those observed with conventional subcutaneous administration. The ELISA assays were performed as follows.

Costar 9018 E.I.A./R.I.A. 96-well plates were coated overnight with 200 ng/well of goat anti-rGH (Diagnostics Systems Laboratories, Cat. No. R01235) in 0.2M NaHCO$_3$—Na$_2$CO$_3$, pH 9.4. Each 96-well plate was washed four times with PBS containing 0.05% Tween 20-0.01% thimerosal (wash buffer); blocked for 1 h with 200 µl/well of PBS/Tween 20 containing 0.5% BSA-0.01% thimerosal (assay buffer). The standard curve was prepared using recombinant rat GH (Diagnostics Systems Laboratories, Cat. No. R01205) diluted in assay buffer (PBST-0.5% BSA). The first point of the standard curve was prepared by adding 50 µl recombinant rat GH to 10 ml assay buffer (1:200), vortexed, and moved 200 µl to 800 µl assay buffer (1:5). For each plate, 0.5 ml was moved to 0.5 ml assay buffer by doing 1:2 serial dilutions for all the subsequent points. The 10 points of the standard curve are: 100, 50, 25, 12.5, 6.25, 3.125, 1.56, 0.78, 0.39 and 0.195 ng/well. Samples were diluted at 1:10 with assay buffer, loaded 100 µl/well in triplicates onto a 96-well plate, and incubated overnight. Each 96-well plate was then washed four times with wash buffer, loaded 100 µl/well of 2$^{nd}$ Ab (rabbit anti-rGH, Cell Sciences, Cat. No. PAAC1) at 1:300 in assay buffer (PBST-0.5% BSA) and incubate at RT for four hours. Each 96-well plate was then washed four times with wash buffer, loaded 100 µl/well of 3rd Ab (goat anti-rabbit IgG-horseradish peroxidase (HRP), Pierce, Cat. No. 31460) at 1:2000 in assay buffer (PBST-0.5% BSA) and incubated at room temperature for two hours. All incubation and coating steps were performed at room temperature on a shaker at 6 RPM. The HRP substrate, TMB (3,3',5,5'tetramethylbenzidine), used to quantify bound antibody, was measured at 450 nm.

ELISA results are reported as the averages of the triplicate OD (450 nm) value of each sample. Rat GH concentrations were determined by the exceeding mean value plus three times the standard error of the mean (SEM) of the appropriate control value.

The results of the ELISA assays are presented in FIGS. 5-7. FIG. 5 presents serum rGH concentrations in BALB/c mice which were dosed by subcutaneous (SC) injection of 30 µg of non-glycosylated recombinant rat GH. Individual mice sera were tested at a dilution of 1:10, and the group average of rGH concentration were reported (n=4 mice per time point). Standard error of the mean (SEM) was indicated by the error bars. As shown in FIG. 5, peak serum concentration of about 240 ng/ml rGH was observed 30 minutes after administration of subcutaneous rGH.

FIG. 6 presents serum rGH concentrations in BALB/c mice which were dosed orally with 100 µg of Delivery Construct 2. Individual mice sera were tested at a dilution of 1:10, and the group average of rGH concentration were reported (n=4 mice per time point). Standard error of the mean (SEM) was indicated by the error bars. As shown in FIG. 5, peak serum concentration of about 280 ng/ml rGH was observed 20 minutes after administration of Delivery Construct 2.

FIG. 7 presents a graphical representation comparing pharmacokinetics of rGH delivered subcutaneously and with Delivery Construct 2. The curve fitting comparison between rGH (SC) and Delivery Construct 2(Oral) was performed by evaluating ELISA data as described above using PK Solutions 2.0, Pharmacokinetics Data Analysis (Summit Research Services, Montrose, Colo.). As shown in FIG. 7, Delivery Construct 2 yields substantially higher peak serum rGH concentrations than subcutaneous administrations of rGH. Further, the peak serum concentration is achieved faster with Delivery Construct 2 relative to subcutaneous rGH. The bioavailability of rGH delivered with Delivery Construct 2 observed was about 60% relative to rGH administered by subcutaneous injection.

6.8.3. Assays Demonstrating Activity of a Macromolecule Following Delivery with a Delivery Construct This example describes analysis of the biological effects of an exemplary macromolecule, rGH, delivered with Delivery Construct 2 in an in vLvo system. In brief, insulin-like growth factor I-binding protein 3 (IGF-I-BP3), growth hormone (GH) receptor and insulin-like growth factor I (IGF-I) expression levels were assessed in liver tissue from mice administered either Delivery Construct 2 or subcutaneous rGH as described above. These transcripts were analyzed because of the well-characterized effects of GH binding to its receptor on IGF-I-BP3 and GH receptor levels. In particular, functional activation of the GH receptor following binding by GH is known to result in upregulation of IGF-I-BP3 and and downregulation of GH receptor expression. Of these, upregulation of IGF-I-BP3 mRNA expression is believed to be the most reliable indicator of GH receptor activation. See, e.g., Sondergaard et al., 2003, *Am J Physiol Endocrinol Metab* 285: E427-32.

Thus, Quantitative Real Time PCR was used to detect and quantify the amount of IGF-I-BP3, GH receptor, IGF-I, and glyceraldehyde-3-phosphate dehydrogenase (GAPDH) mRNA in approximately 30 mg of mouse liver tissue prepared as described above. Collected liver tissue was stored at −70° C. until further processing. Real-time detection of PCR was performed using the Applied Biosystems 7300 Real Time PCR system (Applied Biosystems, Foster City, Calif.). Total RNA from mouse liver was isolated according to the RNeasy Protect Mini Kit (Qiagen). Total RNA was used to generate cDNA for oligo dT oligodeoxynucleotide primer (T12-18) following the protocol for Omniscript Reverse Transcriptase (Qiagen). The primers used to amplify the cDNA were designed using Primer Express software (Applied Biosystems), synthesized by Operon (Alameda, Calif.), and are shown in Table 6;

TABLE 6

|  | RT-PCR Primers |
| --- | --- |
| IGF-I-BP3 (forward): | CGCAGAGAAATGGAGGACACA; |
| IGF-I-BP3 (reverse): | GGACGCCTCTGGGACTCA; |
| GH receptor (forward): | GTTGACGAAATAGTGCAACCTGAT; |
| GH receptor (reverse): | CACGAATCCCGGTCAAACTAA; |
| IGF-I (forward): | GCTATGGCTCCAGCATTCG; |
| IGF-I (reverse): | GCTCCGGAAGCAACACTCA |
| GAPDH (forward): | GCAACAGGGTGGTGGACCT |
| GAPDH (reverse): | GGATAGGGCCTCTCTTGCTCA |

Equal amounts of cDNA were used in duplicate and amplified with the SYBR Green I Master Mix (Applied Biosystems). The thermal cycling parameters were as follows: thermal activation for 10 min at 95° C, and 40 cycles of PCR (melting for 15 s at 95° C and annealing/extension for 1 min at 60° C.). A standard curve was constructed with a dilution curve (1:10, 1:100, 1:500, 1:1,000, 1:2,000) of total RNA from a control mouse liver sample. A "no template control" was included with each PCR. Amplification efficiencies were validated and normalized against GAPDH. Correct PCR product size was confirmed by electrophoresis through a 1% agarose gel stained with ethidium bromide. Purity of the amplified PCR products was determined by a heat-dissociation protocol.

The results of this analysis are shown in FIGS. 8-10. FIG. 8 shows expression levels of IGF-I-BP3 mRNA in the liver of female BALB/c mice treated with 30 µg recombinant rGH by subcutaneous injection or with 100 µg of Delivery Construct 2 by oral gavage. Total RNA extracted from the liver was subjected to quantitative RT-PCR using primers specific for IGF-I-BP3, as described above. Values were normalized to glyceraldehyde-3 phosphate dehydrogenase (GAPDH) and expressed as % of control. As shown in FIG. 8, administration of subcutaneous rGH resulted in an about 250% increase in IGF-1-BP3 mRNA expression levels in the liver at 60 minutes following administration. In contrast, Delivery Construct 2 caused an almost 400% increase in IGF-1-BP3 mRNA expression levels in the liver 30 minutes following administration. Thus, oral administration of Delivery Construct 2 effectively delivered rGH to the bloodstream of the test mice, thereby demonstrating that a delivery construct can effectively deliver an active macromolecule across a mucous membrane in an in vivo system. Moreover, Delivery Construct 2 delivered more active rGH to the liver than subcutaneous administration, and the effects of administration of rGH were observed substantially faster than possible with subcutaneous administration of rGH.

FIG. 9 shows expression levels of growth hormone (GH) receptor mRNA in the liver of female BALB/c mice treated with recombinant rat growth hormone (rGH) by subcutaneous injection (30 µg) or Delivery Construct 2 by oral gavage (100 µg). Total RNA extracted from the liver was subjected to quantitative RT-PCR using primers specific for GH receptor, shown above. Values were normalized to glyceraldehyde-3 phosphate dehydrogenase (GAPDH) and expressed as % of control. As shown in FIG. 9, administration of subcutaneous rGH resulted in a reduction in GH receptor mRNA expression levels in the liver at 60 minutes following administration to about 65% of those observed prior to administration. In contrast, Delivery Construct 2 caused such mRNA levels to decrease to about 15% of those observed prior to administration. Thus, these results confirm that oral administration of Delivery Construct 2 is effective to deliver rGH to the bloodstream of a subject, and further, that Delivery Construct 2 delivers significantly more active rGH to mouse liver than conventional subcutaneous administration of rGH as shown by the enhanced downregulation of GH receptor mRNA expression.

FIG. 10 shows expression levels of insulin-like growth factor I (IGF-I) mRNA in the liver of female BALB/c mice treated with recombinant rat growth hormone (rGH) by subcutaneous injection (30 µg) or Delivery Construct 2 by oral gavage (100 µg). Total RNA extracted from the liver was subjected to quantitative RT-PCR using primers specific for IGF-I, shown above. Values were normalized to glyceraldehyde-3 phosphate dehydrogenase (GAPDH) and expressed as % of control. As shown in FIG. 10, administration of either subcutaneous rGH or Delivery Construct 2 resulted in a reduction in IGF-1 mRNA expression levels in the liver at 30 minutes following administration to about 20% of those observed prior to administration. Thus, both subcutaneous rGH and orally-administered Delivery Construct 2 yielded the same effects, demonstrating that Delivery Construct 2 can deliver active rGH to the bloodstream of a 6.9. Reduced Immunogenicity of Macromolecules Administered with a Delivery Construct This example shows that an exemplary macromolecule, rGH, administered orally with Delivery Construct 2, is less immunogenic than rGH administered subcutaneously.

To assess the relative immunogenicity in mice for rGH administered a delivery construct relative to subcutaneous administration, the serum titer of anti-rGH IgG antibodies from oral administration of 3, 10, or 30 µg Delivery Construct 2 or 3 or 10 µg subcutaneous rGH was determined in an ELISA assay. To do so, 100 µl 1 ng/µl recombinant rGH diluted in coating buffer (0.2 M $NaHCO_3$—$Na_2CO_3$, pH 9.4) was added to Costar EIA/RIA plates, then incubated at room temperature for 16-24 hours. Next, the plates were washed 4 times with 300 µl wash buffer (phosphate-buffered saline). The plates were then blocked with 200 µl blocking buffer (0.5% BSA in phosphate-buffered saline) and incubated at room temperature for 1 hour. Next, the plates were again washed four times with 300 µL wash buffer.

After preparation of the plates, 100 µl diluted samples, standard positive control, or assay buffer as negative control was added to the appropriate well and incubated for one hour. Mouse serum samples and positive control (anti-rGH IgG) were diluted 1:20 in assay buffer (0.5% BSA in phosphate-buffered saline). The plates were then washed four times with 300 µl wash buffer. Next, 100 µl secondary antibody (goat anti-mouse IgG conjugated to horseradish peroxidase, 0.4 mg/ml, Pierce #31430, diluted at 1:6000 in assay buffer and incubated at room temperature for one hour. Next, the plates were again washed four times with 300 µl wash buffer. Next, 100 µl 3,3',5,5'-Tetramethylbenzidine substrate (Sigma) was added to each well and incubated for 2-10 minutes, depending on color development. 100 µl/well 1M $H_2SO_4$ was then added to stop the reaction and absorbance read at 450 nm. All assays were performed in triplicate and the results averaged.

Representative results of the ELISAs are shown in FIGS. 11A-D. The graphs presented in these figures demonstrate that 3, 10, and 30 µg Delivery Construct 2 administered orally elicited a lower titer of anti-rGH IgG antibodies than either 3 or 10 µg subcutaneous rGH. In particular, subcutaneous administration of 10 µg rGH caused a substantial anti-rGH IgG response in all eight mice, while the eight mice administered 3, 10, or 30 µg Delivery Construct 2 by oral gavage had minimal anti-rGH IgG responses. Further, these observations were consistent whether the sera were diluted 1:25 (FIGS. 11A and 11C) or 1:200 (FIGS. 11B and 11D). Finally, it should be noted that each mouse administered 3, 10, or 30 µg Delivery Construct 2 experienced a minimal immune response against rGH, as shown by the tight clustering of the data points in FIGS. 11C and D. Thus, these results demonstrate that oral administration of Delivery Construct 2 not only delivers more active rGH to the liver than possible with subcutaneous injection, but further, the active rGH is less immunogenic when administered orally with Delivery Construct 2 compared to subcutaneous administration.

6.10. Exemplary Delivery Construct for Delivery of Human Growth Hormone

This example describes construction of an exemplary delivery construct for delivering human growth hormone, termed Delivery Construct 6. Techniques similar to those described in Example 6.1, above, were used to construct a plasmid used to express Delivery Construct 6. The nucleotide sequence of the portion of this plasmid that encodes the exemplary delivery construct is presented as FIG. 12, while the amino acid sequence of the delivery construct is presented as FIG. 13.

6.11. Exemplary Delivery Construct for Delivering Inferferon Alpha

This example describes construction of an exemplary delivery construct for delivering IFNα (in this case, IFNα-2b), termed Delivery Construct 7. Techniques similar to those described in Example 6.1, above, were used to construct a plasmid used to express Delivery Construct 7. The nucleotide sequence of the portion of this plasmid that encodes the exemplary Delivery Construct 7 is presented as FIG. 14, while the amino acid sequence of Delivery Construct 7 is presented as FIG. 15.

6.12. Delivery of Interferon Alpha in an In Vivo System

This example demonstrates the use of Delivery Construct 7 to deliver IFNα-2b to the bloodstream of a subject in a mouse model system.

Using an animal feeding needle, 100 µg of Delivery Construct 7 (in 250 µl total volume) was orally administered to female BALB/c mice, 5-6 weeks of age (Charles River Laboratories, Wilmington, Mass.). Delivery Construct 7 was diluted in 1 mg/ml bovine serum albumin (BSA) and phosphate buffered saline (PBS). At specific times after oral gavage and SC administration, mice were euthanized by $CO_2$ asphyxiation and exsanguinated. Whole blood was collected and analyzed as described below.

ELISA assays were used to measure serum concentrations of IFNα-2b in one mouse immediately following administration and in three mice at 15, 30, and 75 minutes following administration. The ELISA assays were performed using R&D Systems Serum ELISA Kit No.41110-1 according to the manufacturer's instructions.

ELISA results are reported as the averages of the triplicate OD (450 nm) value of each sample. The results of the ELISA assays are presented in FIG. 16. As shown in FIG. 16, IFNα-2b was detected at low (about 3 ng/ml) concentration 15 minutes after administration. 30 minutes following administration, serum concentration of IFNα-2b was about 43 ng/ml. 45 minutes following administration, serum concentration of IFNα-2b had fallen to about 13 ng/ml.

6.13. Exemplary Delivery Construct for Delivering Proinsulin

This example describes construction of an exemplary delivery construct for delivering proinsulin, termed Delivery Construct 8. Techniques similar to those described in Example 6.1, above, are used to construct a plasmid used to express Delivery Construct 8. The amino acid sequence of Delivery Construct 8 is presented as FIG. 17.

6.14. Exemplary Delivery Construct for Delivering Insulin

This example describes construction of an exemplary delivery construct for delivering insulin, termed Delivery Construct 9. Techniques similar to those described in Example 6.1, above, are used to construct a plasmid used to express Delivery Construct 9, with certain modifications.

In particular, the scheme used to express Delivery Construct 9 is modified because insulin comprises two separate amino acid chains. In this example, the B-chain of insulin is expressed together with the remainder of the Delivery Construct, constructed according to the general scheme presented in Example 6.1. Amino acids corresponding to the A-chain are made either synthetically (e.g., chemically synthesizing the A-chain peptide from amino acids) or recombinantly (e.g., expressed in a suitable recombinant system such as, for example, *E. coli*, yeast, etc.) The two polypeptides are then combined under conditions that permit association of the A-chain and B-chain. Then, disulfide bonds are made between the two chains of insulin as found in native insulin by application of mildly oxidizing conditions. The amino acid sequence of the two amino acid chains of Delivery Construct 9 is presented as FIG. 17.

The present invention provides, inter alia, delivery constructs and methods of inducing an immune response in a subject. While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Citation of these documents is not an admission that any particular reference is "prior art" to this invention.

TABLE 7

Human Peptidases by Class

| Aspartic-type peptidases | Cysteine-type peptidases | Metallopeptidases | Serine-type peptidases | Threonine-type peptidases |
| --- | --- | --- | --- | --- |
| BAE1_HUMAN (P56817) | BLMH_HUMAN (Q13867) | AMPB_HUMAN (Q9H4A4) | ACRL_HUMAN (P58840) | PS7L_HUMAN (Q8TAA3) |
| BAE2_HUMAN (Q9Y5Z0) | CATB_HUMAN (P07858) | AMPE_HUMAN (Q07075) | ACRO_HUMAN (P10323) | PSA1_HUMAN (P25786) |
| CATD_HUMAN (P07339) | CATC_HUMAN (P53634) | AMPN_HUMAN (P15144) | APOA_HUMAN (P08519) | PSA2_HUMAN (P25787) |
| CATE_HUMAN (P14091) | CATF_HUMAN (Q9UBX1) | ART1_HUMAN (Q9NZ08) | BSS4_HUMAN (Q9GZN4) | PSA3_HUMAN (P25788) |
| NAP1_HUMAN (O96009) | CATH_HUMAN (P09668) | LCAP_HUMAN (Q9UIQ6) | C1R_HUMAN (P00736) | PSA4_HUMAN (P25789) |
| PEPA_HUMAN (P00790) | CATK_HUMAN (P43235) | LKHA_HUMAN (P09960) | C1S_HUMAN (P09871) | PSA5_HUMAN (P28066) |
| PEPC_HUMAN (P20142) | CATL_HUMAN (P07711) | PSA_HUMAN (P55786) | CAP7_HUMAN (P20160) | PSA6_HUMAN (P60900) |
| RENI_HUMAN (P00797) | CATO_HUMAN (P43234) | RNPL_HUMAN (Q9HAU8) | CATG_HUMAN (P08311) | PSA7_HUMAN (O14818) |
| VPRT_HUMAN (P10265) | CATS_HUMAN (P25774) | THDE_HUMAN (Q9UKU6) | CFAB_HUMAN (P00751) | PSB1_HUMAN (P20618) |
| Other Peptidases | CATW_HUMAN (P56202) | ACET_HUMAN (P22966) | CFAD_HUMAN (P00746) | PSB2_HUMAN (P49721) |
| FAC2_HUMAN (Q9Y256) | CATZ_HUMAN (Q9UBR2) | ACE_HUMAN (P12821) | CFAI_HUMAN (P05156) | PSB3_HUMAN (P49720) |
| | CSL2_HUMAN (O60911) | MEPD_HUMAN (P52888) | CLCR_HUMAN (Q99895) | PSB4_HUMAN (P28070) |
| | TNAG_HUMAN (Q9UJW2) | NEUL_HUMAN (Q9BYT8) | CO2_HUMAN (P06681) | PSB5_HUMAN (P28074) |
| | CAN1_HUMAN (P07384) | PMIP_HUMAN (Q99797) | CORI_HUMAN (Q9Y5Q5) | PSB6_HUMAN (P28072) |
| | CAN2_HUMAN (P17655) | MM01_HUMAN (P03956) | CRAR_HUMAN (P48740) | PSB7_HUMAN (Q99436) |
| | CAN3_HUMAN (P20807) | MM02_HUMAN (P08253) | CTRB_HUMAN (P17538) | PSB8_HUMAN (P28062) |
| | CAN5_HUMAN (O15484) | MM03_HUMAN (P08254) | CTRL_HUMAN (P40313) | PSB9_HUMAN (P28065) |
| | CAN6_HUMAN (Q9Y6Q1) | MM07_HUMAN (P09237) | DES1_HUMAN (Q9UL52) | PSBA_HUMAN (P40306) |
| | CAN7_HUMAN (Q9Y6W3) | MM08_HUMAN (P22894) | EL1_HUMAN (Q9UNI1) | |
| | CAN9_HUMAN (O14815) | MM09_HUMAN (P14780) | EL2A_HUMAN (P08217) | |
| | CANA_HUMAN (Q9HC96) | MM10_HUMAN (P09238) | EL2B_HUMAN (P08218) | |
| | CANB_HUMAN (Q9UMQ6) | MM11_HUMAN (P24347) | EL3A_HUMAN (P09093) | |
| | UBL1_HUMAN (P09936) | MM12_HUMAN (P39900) | EL3B_HUMAN (P08861) | |
| | UBL3_HUMAN (P15374) | MM13_HUMAN (P45452) | ELNE_HUMAN (P08246) | |
| | UBL5_HUMAN (Q9Y5K5) | MM14_HUMAN (P50281) | ENTK_HUMAN (P98073) | |
| | GPI8_HUMAN (Q92643) | MM15_HUMAN (P51511) | FA10_HUMAN (P00742) | |
| | LGMN_HUMAN (Q99538) | MM16_HUMAN (P51512) | FA11_HUMAN (P03951) | |
| | CFLA_HUMAN (O15519) | MM17_HUMAN (Q9ULZ9) | FA12_HUMAN (P00748) | |
| | I1BC_HUMAN (P29466) | MM19_HUMAN (Q99542) | FA7_HUMAN (P08709) | |
| | ICE2_HUMAN (P42575) | MM20_HUMAN (O60882) | FA9_HUMAN (P00740) | |
| | ICE3_HUMAN (P42574) | MM21_HUMAN (Q8N119) | GRAA_HUMAN (P12544) | |
| | ICE4_HUMAN (P49662) | MM24_HUMAN (Q9Y5R2) | GRAB_HUMAN (P10144) | |
| | ICE5_HUMAN (P51878) | MM25_HUMAN (Q9NPA2) | GRAH_HUMAN (P20718) | |
| | ICE6_HUMAN (P55212) | MM26_HUMAN (Q9NRE1) | GRAK_HUMAN (P49863) | |
| | ICE7_HUMAN (P55210) | MM28_HUMAN (Q9H239) | GRAM_HUMAN (P51124) | |
| | ICE8_HUMAN (Q14790) | BMP1_HUMAN (P13497) | HATT_HUMAN (O60235) | |
| | ICE9_HUMAN (P55211) | MEPA_HUMAN (Q16819) | HEPS_HUMAN (P05981) | |
| | ICEA_HUMAN (Q92851) | MEPB_HUMAN (Q16820) | HGFA_HUMAN (Q04756) | |
| | ICEE_HUMAN (P31944) | AD02_HUMAN (Q99965) | HGFL_HUMAN (P26927) | |
| | MLT1_HUMAN (Q9UDY8) | AD07_HUMAN (Q9H2U9) | HGF_HUMAN (P14210) | |
| | PGPI_HUMAN (Q9NXJ5) | AD08_HUMAN (P78325) | HPTR_HUMAN (P00739) | |
| | FAFX_HUMAN (Q93008) | AD09_HUMAN (Q13443) | HPT_HUMAN (P00738) | |
| | FAFY_HUMAN (O00507) | AD10_HUMAN (O14672) | KAL_HUMAN (P03952) | |

TABLE 7-continued

Human Peptidases by Class

| Aspartic-type peptidases | Cysteine-type peptidases | Metallopeptidases | Serine-type peptidases | Threonine-type peptidases |
|---|---|---|---|---|
| | UB10_HUMAN (Q14694) | AD11_HUMAN (O75078) | KLK1_HUMAN (P06870) | |
| | UB11_HUMAN (P51784) | AD12_HUMAN (O43184) | KLK2_HUMAN (P20151) | |
| | UB12_HUMAN (O75317) | AD15_HUMAN (Q13444) | KLK3_HUMAN (P07288) | |
| | UB13_HUMAN (Q92995) | AD17_HUMAN (P78536) | KLK4_HUMAN (Q9Y5K2) | |
| | UB14_HUMAN (P54578) | AD18_HUMAN (Q9Y3Q7) | KLK5_HUMAN (Q9Y337) | |
| | UB15_HUMAN (Q9Y4E8) | AD19_HUMAN (Q9H013) | KLK6_HUMAN (Q92876) | |
| | UB16_HUMAN (Q9Y5T5) | AD20_HUMAN (O43506) | KLK7_HUMAN (P49862) | |
| | UB18_HUMAN (Q9UMW8) | AD21_HUMAN (Q9UKJ8) | KLK8_HUMAN (O60259) | |
| | UB19_HUMAN (O94966) | AD22_HUMAN (Q9P0K1) | KLK9_HUMAN (Q9UKQ9) | |
| | UB20_HUMAN (Q9Y2K6) | AD28_HUMAN (Q9UKQ2) | KLKA_HUMAN (O43240) | |
| | UB21_HUMAN (Q9UK80) | AD29_HUMAN (Q9UKF5) | KLKB_HUMAN (Q9UBX7) | |
| | UB22_HUMAN (Q9UPT9) | AD30_HUMAN (Q9UKF2) | KLKC_HUMAN (Q9UKR0) | |
| | UB24_HUMAN (Q9UPU5) | AD33_HUMAN (Q9BZ11) | KLKD_HUMAN (Q9UKR3) | |
| | UB25_HUMAN (Q9UHP3) | AT10_HUMAN (Q9H324) | KLKE_HUMAN (Q9P0G3) | |
| | UB26_HUMAN (Q9BXU7) | AT12_HUMAN (P58397) | KLKF_HUMAN (Q9H2R5) | |
| | UB28_HUMAN (Q96RU2) | AT14_HUMAN (Q8WXS8) | LCLP_HUMAN (P34168) | |
| | UB29_HUMAN (Q9HBJ7) | AT15_HUMAN (Q8TE58) | MAS2_HUMAN (O00187) | |
| | UB32_HUMAN (Q8NFA0) | AT16_HUMAN (Q8TE57) | MCT1_HUMAN (P23946) | |
| | UB33_HUMAN (Q8TEY7) | AT17_HUMAN (Q8TE56) | NETR_HUMAN (P56730) | |
| | UB35_HUMAN (Q9P2H5) | AT18_HUMAN (Q8TE60) | PLMN_HUMAN (P00747) | |
| | UB36_HUMAN (Q9P275) | AT19_HUMAN (Q8TE59) | PR27_HUMAN (Q9BQR3) | |
| | UB37_HUMAN (Q86T82) | AT20_HUMAN (P59510) | PRN3_HUMAN (P24158) | |
| | UB38_HUMAN (Q8NB14) | ATS1_HUMAN (Q9UHI8) | PRTC_HUMAN (P04070) | |
| | UB40_HUMAN (Q9NVE5) | ATS2_HUMAN (O95450) | PRTZ_HUMAN (P22891) | |
| | UB42_HUMAN (Q9H9J4) | ATS3_HUMAN (O15072) | PS23_HUMAN (O95084) | |
| | UB44_HUMAN (Q9H0E7) | ATS4_HUMAN (O75173) | PSS8_HUMAN (Q16651) | |
| | UB46_HUMAN (P62068) | ATS5_HUMAN (Q9UNA0) | ST14_HUMAN (Q9Y5Y6) | |
| | UBP1_HUMAN (O94782) | ATS6_HUMAN (Q9UKP5) | TEST_HUMAN (Q9Y6M0) | |
| | UBP2_HUMAN (O75604) | ATS7_HUMAN (Q9UKP4) | THRB_HUMAN (P00734) | |
| | UBP3_HUMAN (Q9Y6I4) | ATS8_HUMAN (Q9UP79) | TMS2_HUMAN (O15393) | |
| | UBP4_HUMAN (Q13107) | ATS9_HUMAN (Q9P2N4) | TMS3_HUMAN (P57727) | |
| | UBP5_HUMAN (P45974) | ECE1_HUMAN (P42892) | TMS4_HUMAN (Q9NRS4) | |
| | UBP6_HUMAN (P35125) | ECE2_HUMAN (O60344) | TMS5_HUMAN (Q9H3S3) | |
| | UBP7_HUMAN (Q93009) | ECEL_HUMAN (O95672) | TMS6_HUMAN (Q8IU80) | |
| | UBP8_HUMAN (P40818) | KELL_HUMAN (P23276) | TPA_HUMAN (P00750) | |
| | GGH_HUMAN (Q92820) | NEP_HUMAN (P08473) | TRB1_HUMAN (Q15661) | |
| | SEN1_HUMAN (Q9P0U3) | PEX_HUMAN (P78562) | TRB2_HUMAN (P20231) | |
| | SEN3_HUMAN (Q9H4L4) | CBP1_HUMAN (P15085) | TRY1_HUMAN (P07477) | |
| | SEN5_HUMAN (Q96HI0) | CBP2_HUMAN (P48052) | TRY2_HUMAN (P07478) | |
| | SEN6_HUMAN (Q9GZR1) | CBP4_HUMAN (Q9UI42) | TRY3_HUMAN (P35030) | |
| | SEN7_HUMAN (Q9BQF6) | CBP5_HUMAN (Q8WXQ8) | TRYA_HUMAN (P15157) | |
| | SEN8_HUMAN (Q96LD8) | CBP6_HUMAN (Q8N4T0) | TRYD_HUMAN (Q9BZJ3) | |
| | SNP2_HUMAN (Q9HC62) | CBPB_HUMAN (P15086) | TRYG_HUMAN (Q9NRR2) | |
| | ESP1_HUMAN (Q14674) | CBPC_HUMAN (P15088) | TS50_HUMAN (Q9UI38) | |
| | | CBPD_HUMAN (O75976) | UROK_HUMAN (P00749) | |
| | | CBPE_HUMAN (P16870) | HRA1_HUMAN (Q92743) | |
| | | CBPM_HUMAN (P14384) | HRA2_HUMAN (O43464) | |
| | | CBPN_HUMAN (P15169) | HRA3_HUMAN (P83110) | |
| | | CPX2_HUMAN (Q8N436) | HRA4_HUMAN (P83105) | |
| | | CPXM_HUMAN (Q96SM3) | FURI_HUMAN (P09958) | |
| | | IDE_HUMAN (P14735) | MS1P_HUMAN (Q14703) | |
| | | MPPA_HUMAN (Q10713) | NEC1_HUMAN (P29120) | |
| | | MPPB_HUMAN (O75439) | NEC2_HUMAN (P16519) | |
| | | NRDC_HUMAN (O43847) | PCK5_HUMAN (Q92824) | |
| | | UCR1_HUMAN (P31930) | PCK6_HUMAN (P29122) | |
| | | UCR2_HUMAN (P22695) | PCK7_HUMAN (Q16549) | |
| | | AMPL_HUMAN (P28838) | PCK9_HUMAN (Q8NBP7) | |
| | | PEL1_HUMAN (Q8NDH3) | TPP2_HUMAN (P29144) | |
| | | DNPE_HUMAN (Q9ULA0) | PPCE_HUMAN (P48147) | |
| | | MDP1_HUMAN (P16444) | DPP4_HUMAN (P27487) | |
| | | CGL1_HUMAN (Q96KP4) | DPP6_HUMAN (P42658) | |
| | | CGL2_HUMAN (Q96KN2) | SEPR_HUMAN (Q12884) | |
| | | ACY1_HUMAN (Q03154) | ACPH_HUMAN (P13798) | |
| | | GCP_HUMAN (Q9NPF4) | CPVL_HUMAN (Q9H3G5) | |
| | | AMP1_HUMAN (P53582) | PRTP_HUMAN (P10619) | |
| | | PEPD_HUMAN (P12955) | RISC_HUMAN (Q9HB40) | |
| | | XPP2_HUMAN (O43895) | CLPP_HUMAN (Q16740) | |
| | | AMP2_HUMAN (P50579) | LONM_HUMAN (P36776) | |
| | | P2G4_HUMAN (Q9UQ80) | SPC3_HUMAN (Q9BY50) | |
| | | FOH1_HUMAN (Q04609) | SPC4_HUMAN (P21378) | |
| | | NLD2_HUMAN (Q9Y3Q0) | DPP2_HUMAN (Q9UHL4) | |
| | | NLDL_HUMAN (Q9UQQ1) | PCP_HUMAN (P42785) | |
| | | TFR1_HUMAN (P02786) | TSSP_HUMAN (Q9NQE7) | |
| | | TFR2_HUMAN (Q9UP52) | HYEP_HUMAN (P07099) | |
| | | AF31_HUMAN (O43931) | TPP1_HUMAN (O14773) | |

TABLE 7-continued

| Human Peptidases by Class | | | | |
|---|---|---|---|---|
| Aspartic-type peptidases | Cysteine-type peptidases | Metallopeptidases | Serine-type peptidases | Threonine-type peptidases |
| | | AF32_HUMAN (Q9Y4W6) | RHB1_HUMAN (O75783) | |
| | | SPG7_HUMAN (Q9UQ90) | RHB2_HUMAN (Q9NX52) | |
| | | YME1_HUMAN (Q96TA2) | RHB4_HUMAN (P58872) | |
| | | PAPA_HUMAN (Q13219) | | |
| | | FAC1_HUMAN (O75844) | | |
| | | DPP3_HUMAN (Q9NY33) | | |
| | | MS2P_HUMAN (O43462) | | |

What is claimed is:

1. An isolated delivery construct, comprising:
   a)—a receptor binding domain,
   b)—a transcytosis domain,
   c)—a peptide, polypeptide, or protein to be delivered to a subject, and
   d)—a cleavable linker,
   wherein upon transcytosis of said delivery construct across a normal, polarized epithelial cell in said subject, said cleavable linker is cleaved at a basal-lateral membrane of the polarized epithelial cell or in the plasma in said subject, and said peptide, polypeptide, or protein is separated from the receptor binding domain and the transcytosis domain, by an enzyme that i) exhibits greater activity at a basal-lateral membrane of a normal, polarized epithelial cell in said subject than at an apical membrane of the polarized epithelial cell, or ii) exhibits greater activity in the plasma in said subject than at an apical membrane of the polarized epithelial cell in the subject.

2. The delivery construct of claim 1, further comprising a second cleavable linker, wherein upon transcytosis of said delivery construct across a normal, polarized epithelial cell in said subject, said second cleavable linker is cleaved at a basal-lateral membrane of the polarized epithelial cell or in the plasma in said subject, and said peptide, polypeptide, or protein is separated from the receptor binding domain and the transcytosis domain, by an enzyme that i) exhibits greater activity at a basal-lateral membrane of a normal, polarized epithelial cell in said subject than at an apical membrane of the polarized epithelial cell, or ii) exhibits greater activity in the plasma in said subject than at an apical membrane of the polarized epithelial cell in the subject.

3. The delivery construct of claim 1, wherein said cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10).

4. The delivery construct of claim 1, wherein said enzyme that is present at a basal-lateral membrane of a normal, polarized epithelial cell is selected from the group consisting of Cathepsin GI, Chymotrypsin I, Elastase I, Subtilisin Al, Subtilisin All, Thrombin I, and Urokinase I.

5. The delivery construct of claim 1, wherein said receptor binding domain is selected from the group consisting of receptor binding domains from *Pseudomonas* exotoxin A, cholera toxin, botulinum toxin, diptheria toxin, shiga toxin, or shiga-like toxin; antibodies; TGF α; EGF; IGF-I; IGF-II; IGF-III; IL-1; IL-2; IL-3; IL-6; MIP-1a; MIP-1b; MCAF; and IL-8.

6. The delivery construct of claim 1, wherein said receptor binding domain binds to a cell-surface receptor that is selected from the group consisting of α2-macroglobulin receptor, epidermal growth factor receptor, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor.

7. The delivery construct of claim 5, wherein said receptor binding domain of *Pseudomonas* exotoxin A is Domain Ia of *Pseudomonas* exotoxin A.

8. The delivery construct of claim 7, wherein said receptor binding domain of *Pseudomonas* exotoxin A has an amino acid sequence that is SEQ ID NO.:1.

9. The delivery construct of claim 1, wherein said transcytosis domain is selected from the group consisting of transcytosis domains from *Pseudomonas* exotoxin A, botulinum toxin, diptheria toxin, pertussis toxin, cholera toxin, heat-labile *E. coli* enterotoxin, shiga toxin, and shiga-like toxin.

10. The delivery construct of claim 9, wherein said transcytosis domain is *Pseudomonas* exotoxin A transcytosis domain.

11. The delivery construct of claim 10, wherein said *Pseudomonas* exotoxin A transcytosis domain has an amino acid sequence that is SEQ ID NO.:2.

12. The delivery construct of claim 1, wherein said peptide, polypeptide, or protein is selected from the group consisting of a peptide and a polypeptide.

13. The delivery construct of claim 12, wherein said polypeptide is selected from the group consisting of polypeptide hormones, cytokines, chemokines, growth factors, and clotting factors.

14. The delivery construct of claim 13, wherein said polypeptide is selected from the group consisting of IGF-I, IGF-II, IGF-III, EGF, IFN-α, IFN-β, IFN-γ, G-CSF, GM-CSF, IL-1, IL-2, IL-3, IL-6, IL-8, IL-12, EPO, growth hormone, factor VII, vasopressin, calcitonin, parathyroid hormone, luteinizing hormone-releasing factor, tissue plasminogen activators, proinsulin, insulin, glucocorticoid, amylin, adrenocorticotropin, enkephalin, and glucagon-like peptide 1.

15. The delivery construct of claim 14, wherein said polypeptide is human growth hormone.

16. The delivery construct of claim 12, wherein said protein is human insulin.

17. The delivery construct of claim 12, wherein said protein is human IFN-α.

18. The delivery construct of claim 12, wherein said protein is human IFN-α2b.

19. The delivery construct of claim 12, wherein said protein is human proinsulin.

20. The delivery construct of claim 1, further comprising a second peptide, polypeptide, or protein and a second cleavable linker, wherein upon transcytosis of said delivery construct across a normal, polarized epithelial cell in said subject, said second cleavable linker is cleaved at a basal-lateral membrane of the polarized epithelial cell or in the plasma in said subject, and said second peptide, polypeptide, or protein is separated from the receptor binding domain and the transcytosis domain, by an enzyme that i) exhibits greater activity at a basal-lateral membrane of a normal, polarized epithelial cell in said subject than at an apical membrane of the polarized epithelial cell, or ii) exhibits greater activity in the plasma in said subject than at an apical membrane of the polarized epithelial cell in the subject.

21. The delivery construct of claim 20, wherein the peptide polypeptide, or protein and said second peptide, polypeptide, or protein associate to form a multimer.

22. The delivery construct of claim 21, wherein said multimer is a dimer, tetramer, or octamer.

23. The delivery construct of claim 22, wherein said dimer is an antibody.

24. A polynucleotide that encodes an isolated delivery construct, said delivery construct comprising:
   a)—a receptor binding domain,
   b)—a transcytosis domain,
   c)—a peptide, polypeptide, or protein to be delivered to a subject, and
   d)—a cleavable linker,
   wherein upon transcytosis of said delivery construct across a normal, polarized epithelial cell in said subject, said cleavable linker is cleaved at a basal-lateral membrane of the polarized epithelial cell or in the plasma in said subject, and said peptide, polypeptide, or protein is separated from the receptor binding domain and the transcytosis domain, by an enzyme that i) exhibits greater activity at a basal-lateral membrane of a normal, polarized epithelial cell in said subject than at an apical membrane of the polarized epithelial cell, or ii) exhibits greater activity in the plasma in said subject than at an apical membrane of the polarized epithelial cell in the subject.

25. A polynucleotide that encodes a delivery construct, said polynucleotide comprising:
   a)—a nucleic acid sequence encoding a receptor binding domain,
   b)—a nucleic acid sequence encoding a transcytosis domain,
   c)—a nucleic acid sequence encoding a cleavable linker, and
   d)—a nucleic acid sequence comprising a polylinker insertion site,
   wherein said polylinker insertion site is oriented relative to said nucleic acid sequence encoding a cleavable linker to allow cleavage of the cleavable linker to separate a peptide, polypeptide, or protein that is encoded by a nucleic acid inserted into said polylinker insertion site from the receptor binding domain and the transcytosis domain, and wherein upon transcytosis of said delivery construct across a normal, polarized epithelial cell in said subject, said cleavable linker is cleaved at a basal-lateral membrane of the polarized epithelial cell or in the plasma in said subject by an enzyme that i) exhibits greater activity at a basal-lateral membrane of a normal, polarized epithelial cell of a subject than at an apical membrane of the polarized epithelial cell, or ii) exhibits greater activity in the plasma in said subject than at an apical membrane of the polarized epithelial cell in the subject.

26. An expression vector comprising the polynucleotide of claim 24 or 25.

27. A cell comprising the expression vector of claim 26.

28. A composition comprising a delivery construct, said delivery construct comprising:
   a)—a receptor binding domain,
   b)—a transcytosis domain, c)—a peptide, polypeptide, or protein to be delivered to a subject, and d)—a cleavable linker, wherein upon transcytosis of said delivery construct across a normal, polarized epithelial cell in said subject, said cleavable linker is cleaved at a basal-lateral membrane of the polarized epithelial cell or in the plasma in said subject, and said peptide, polypeptide, or protein is separated from the receptor binding domain and the transcytosis domain, by an enzyme that i) exhibits greater activity at a basal-lateral membrane of a normal, polarized epithelial cell in said subject than at an apical membrane of the polarized epithelial cell, or ii) exhibits greater activity in the plasma in said subject than at an apical membrane of the polarized epithelial cell in the subject.

29. The composition of claim 28, wherein said composition further comprises a pharmaceutically acceptable diluent, excipient, vehicle, or carrier.

30. The composition of claim 28, wherein said composition is formulated for nasal or oral administration.

31. The delivery construct of claim 5, wherein said receptor binding domain of antibodies is a receptor binding domain of a monoclonal antibody or a single chain antibody.

* * * * *

SEQUENCE LISTING

<160> NUMBER OF SEQ ID NOS: 41

<210> SEQ ID NO 1
<211> LENGTH: 266
<212> TYPE: PRT
<213> ORGANISM: P. aeruginosa
<220> FEATURE:
<223> OTHER INFORMATION: Polypeptide

<400> SEQUENCE: 1

```
Met His Leu Ile Pro His Trp Ile Pro Leu Val Ala Ser Leu Gly Leu
 1               5                  10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255
```

Pro Ala Lys His Asp Leu Asp Ile Lys Pro
              260                 265

<210> SEQ ID NO 2
<211> LENGTH: 153
<212> TYPE: PRT
<213> ORGANISM: P. aeruginosa
<220> FEATURE:
<223> OTHER INFORMATION: Polypeptide

<400> SEQUENCE: 2

Thr Val Ile Ser His Arg Leu His Phe Pro Glu Gly Gly Ser Leu Ala
 1               5                  10                  15

Ala Leu Thr Ala His Gln Ala Cys His Leu Pro Leu Glu Thr Phe Thr
             20                  25                  30

Arg His Arg Gln Pro Arg Gly Trp Glu Gln Leu Glu Gln Cys Gly Tyr
         35                  40                  45

Pro Val Gln Arg Leu Val Ala Leu Tyr Leu Ala Ala Arg Leu Ser Trp
     50                  55                  60

Asn Gln Val Asp Gln Val Ile Arg Asn Ala Leu Ala Ser Pro Gly Ser
65                  70                  75                  80

Gly Gly Asp Leu Gly Glu Ala Ile Arg Glu Gln Pro Glu Gln Ala Arg
                 85                  90                  95

Leu Ala Leu Thr Leu Ala Ala Ala Glu Ser Glu Arg Phe Val Arg Gln
            100                 105                 110

Gly Thr Gly Asn Asp Glu Ala Gly Ala Ala Asn Ala Asp Val Val Ser
        115                 120                 125

Leu Thr Cys Pro Val Ala Ala Gly Glu Cys Ala Gly Pro Ala Asp Ser
    130                 135                 140

Gly Asp Ala Leu Leu Glu Arg Asn Tyr
145                 150

<210> SEQ ID NO 3
<211> LENGTH: 1839
<212> TYPE: DNA
<213> ORGANISM: P. aeruginosa
<220> FEATURE:
<223> OTHER INFORMATION: Polynucleotide

<400> SEQUENCE: 3
gccgaagaag ctttcgacct ctggaacgaa tgcgccaaag cctgcgtgct cgacctcaag      60
gacggcgtgc gttccagccg catgagcgtc gacccggcca tcgccgacac caacggccag     120
ggcgtgctgc actactccat ggtcctggag gcggcaacg acgcgctcaa gctggccatc     180
gacaacgccc tcagcatcac cagcgacggc ctgaccatcc gcctcgaagg cggcgtcgag     240
ccgaacaagc cggtgcgcta cagctacacg cgccaggcgc gcggcagttg gtcgctgaac     300
tggctggtac cgatcggcca cgagaagccc tcgaacatca aggtgttcat ccacgaactg     360
aacgccggca ccagctcag ccacatgtcg ccgatctaca ccatcgagat gggcgacgag     420
ttgctggcga gctggcgcg cgatgccacc ttcttcgtca gggcgcacga gagcaacgag     480
atgcagccga cgctcgccat cagccatgcc ggggtcagcg tggtcatggc ccagacccag     540
ccgcgccggg aaaagcgctg gagcgaatgg ccagcggca aggtgttgtg cctgctcgac      600
ccgctggacg gggtctacaa ctacctcgcc cagcaacgct gcaacctcga cgatacctgg     660
gaaggcaaga tctaccgggt gctcgccggc aacccggcga agcatgacct ggacatcaaa     720
cccacggtca tcagtcatcg cctgcacttt ccgagggcg gcagcctggc cgcgctgacc     780

```
gcgcaccagg cttgccacct gccgctggag actttcaccc gtcatcgcca gccgcgcggc    840
tgggaacaac tggagcagtg cggctatccg gtgcagcggc tggtcgccct ctacctggcg    900
gcgcggctgt cgtggaacca ggtcgaccag gtgatccgca acgccctggc cagccccggc    960
agcggcggcg acctgggcga agcgatccgc gagcagccgg agcaggcccg tctggccctg   1020
accctggccg ccgccgagag cgagcgcttc gtccggcagg gcaccggcaa cgacgaggcc   1080
ggcgcggcca acgccgacgt ggtgagcctg acctgcccgg tcgccgccgg tgaatgcgcg   1140
ggcccggcgg acagcggcga cgccctgctg gagcgcaact atcccactgg cgcggagttc   1200
ctcggcgacg gcgcgacgt cagcttcagc acccgcggca cgcagaactg gacggtggag   1260
cggctgctcc aggcgcaccg ccaactggag gagcgcggct atgtgttcgt cggctaccac   1320
ggcaccttcc tcgaagcggc gcaaagcatc gtcttcggcg gggtgcgcgc gcgcagccag   1380
gacctcgacg cgatctggcg cggtttctat atcgccggcg atccggcgct ggcctacggc   1440
tacgcccagg accaggaacc cgacgcacgc ggccggatcc gcaacggtgc cctgctgcgg   1500
gtctatgtgc cgcgctcgag cctgccgggc ttctaccgca ccagcctgac cctggccgcg   1560
ccggaggcgg cgggcgaggt cgaacggctg atcggccatc cgctgccgct gcgcctggac   1620
gccatcaccg ccccgaggga ggaaggcggg cgcctggaga ccattctcgg ctggccgctg   1680
gccgagcgca ccgtggtgat tccctcggcg atccccaccg accgcgcaa cgtcggcggc   1740 gacctcgacc cgtccagcat ccccgacaag gaacaggcga tcagcgccct gccggactac   1800
gccagccagc ccggcaaacc gccgcgcgag gacctgaag                          1839
```

<210> SEQ ID NO 4
<211> LENGTH: 4
<212> TYPE: PRT
<213> ORGANISM: P. aeruginosa
<220> FEATURE:
<223> OTHER INFORMATION: Peptide

<400> SEQUENCE: 4

Ala Ala Pro Phe
 1

<210> SEQ ID NO 5
<211> LENGTH: 3
<212> TYPE: PRT
<213> ORGANISM: P. aeruginosa
<220> FEATURE:
<223> OTHER INFORMATION: Peptide

<400> SEQUENCE: 5

Gly Gly Phe
 1

<210> SEQ ID NO 6
<211> LENGTH: 4
<212> TYPE: PRT
<213> ORGANISM: P. aeruginosa
<220> FEATURE:
<223> OTHER INFORMATION: Peptide

<400> SEQUENCE: 6

Ala Ala Pro Val
 1

<210> SEQ ID NO 7
<211> LENGTH: 3
<212> TYPE: PRT

```
<213> ORGANISM: P. aeruginosa
<220> FEATURE:
<223> OTHER INFORMATION: Peptide

<400> SEQUENCE: 7

Gly Gly Leu
 1

<210> SEQ ID NO 8
<211> LENGTH: 3
<212> TYPE: PRT
<213> ORGANISM: P. aeruginosa
<220> FEATURE:
<223> OTHER INFORMATION: Peptide

<400> SEQUENCE: 8

Ala Ala Leu
 1

<210> SEQ ID NO 9
<211> LENGTH: 3
<212> TYPE: PRT
<213> ORGANISM: P. aeruginosa
<220> FEATURE:
<223> OTHER INFORMATION: Peptide

<400> SEQUENCE: 9

Phe Val Arg
 1

<210> SEQ ID NO 10
<211> LENGTH: 3
<212> TYPE: PRT
<213> ORGANISM: P. aeruginosa
<220> FEATURE:
<223> OTHER INFORMATION: Peptide

<400> SEQUENCE: 10

Val Gly Arg
 1

<210> SEQ ID NO 11
<211> LENGTH: 5
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 5
<223> OTHER INFORMATION: Xaa = Any Amino Acid

<400> SEQUENCE: 11

Tyr Val Ala Asp Xaa
 1               5

<210> SEQ ID NO 12
<211> LENGTH: 5
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 2, 3, 5
<223> OTHER INFORMATION: Xaa = Any Amino Acid

<400> SEQUENCE: 12
```

```
Asp Xaa Xaa Asp Xaa
 1               5

<210> SEQ ID NO 13
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 2, 4
<223> OTHER INFORMATION: Xaa = Any Amino Acid

<400> SEQUENCE: 13

Arg Xaa Arg Xaa
 1

<210> SEQ ID NO 14
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 2, 4
<223> OTHER INFORMATION: Xaa = Any Amino Acid

<400> SEQUENCE: 14

Lys Xaa Arg Xaa
 1

<210> SEQ ID NO 15
<211> LENGTH: 6
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 6
<223> OTHER INFORMATION: Xaa = Any Amino Acid

<400> SEQUENCE: 15

Gly Arg Thr Lys Arg Xaa
 1               5

<210> SEQ ID NO 16
<211> LENGTH: 5
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 5
<223> OTHER INFORMATION: Xaa = Any Amino Acid

<400> SEQUENCE: 16

Arg Val Arg Arg Xaa
 1               5

<210> SEQ ID NO 17
<211> LENGTH: 6
<212> TYPE: PRT
<213> ORGANISM: P. aeruginosa
<220> FEATURE:
<223> OTHER INFORMATION: Peptide
<220> FEATURE:
```

-continued

```
<221> NAME/KEY: VARIANT
<222> LOCATION: 6
<223> OTHER INFORMATION: Xaa = Any Amino Acid

<400> SEQUENCE: 17

Asp Arg Val Arg Arg Xaa
 1               5

<210> SEQ ID NO 18
<211> LENGTH: 6
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 2, 6
<223> OTHER INFORMATION: Xaa = Any Amino Acid

<400> SEQUENCE: 18

Pro Xaa Trp Val Pro Xaa
 1               5

<210> SEQ ID NO 19
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 4
<223> OTHER INFORMATION: Xaa = Any Amino Acid

<400> SEQUENCE: 19

Trp Val Ala Xaa
 1

<210> SEQ ID NO 20
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 1, 3, 4
<223> OTHER INFORMATION: Xaa = Any Amino Acid

<400> SEQUENCE: 20

Xaa Phe Xaa Xaa
 1

<210> SEQ ID NO 21
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 1, 3, 4
<223> OTHER INFORMATION: Xaa = Any Amino Acid

<400> SEQUENCE: 21

Xaa Tyr Xaa Xaa
 1

<210> SEQ ID NO 22
```

```
<211> LENGTH: 4
<212> TYPE: PRT
<213> ORGANISM: P. aeruginosa
<220> FEATURE:
<223> OTHER INFORMATION: Peptide
<220> FEATURE:
<221> NAME/KEY: VARIANT
<222> LOCATION: 1, 3, 4
<223> OTHER INFORMATION: Xaa = Any Amino Acid

<400> SEQUENCE: 22

Xaa Trp Xaa Xaa
 1

<210> SEQ ID NO 23
<211> LENGTH: 16
<212> TYPE: PRT
<213> ORGANISM: P. aeruginosa
<220> FEATURE:
<223> OTHER INFORMATION: Peptide

<400> SEQUENCE: 23

Asp Arg Tyr Ile Pro Phe His Leu Leu Val Ala Pro Tyr Ser Pro Ala
 1               5                  10                  15

<210> SEQ ID NO 24
<211> LENGTH: 37
<212> TYPE: DNA
<213> ORGANISM: P. aeruginosa
<220> FEATURE:
<223> OTHER INFORMATION: Oligonucleotide

<400> SEQUENCE: 24
aactgcagcg ccagcctcga ggaggattac tgcagaa                           37

<210> SEQ ID NO 25
<211> LENGTH: 37
<212> TYPE: DNA
<213> ORGANISM: P. aeruginosa
<220> FEATURE:
<223> OTHER INFORMATION: Oligonucleotide

<400> SEQUENCE: 25
ttctgcagta atcctcctcg aggctggcgc tgcagtt                           37

<210> SEQ ID NO 26
<211> LENGTH: 37
<212> TYPE: DNA
<213> ORGANISM: P. aeruginosa
<220> FEATURE:
<223> OTHER INFORMATION: Oligonucleotide

<400> SEQUENCE: 26
aactgcaggg aggcttacgc cagcctcgac tgcagaa                           37

<210> SEQ ID NO 27
<211> LENGTH: 37
<212> TYPE: DNA
<213> ORGANISM: P. aeruginosa
<220> FEATURE:
<223> OTHER INFORMATION: Oligonucleotide

<400> SEQUENCE: 27
ttctgcagtc gaggctggcg taagcctccc tgcagtt                           37

<210> SEQ ID NO 28
<211> LENGTH: 37
```

```
<212> TYPE: DNA
<213> ORGANISM: P. aeruginosa
<220> FEATURE:
<223> OTHER INFORMATION: Oligonucleotide

<400> SEQUENCE: 28
aactgcagcg ccagcctcga gagggccgtc tgcagaa                                37

<210> SEQ ID NO 29
<211> LENGTH: 37
<212> TYPE: DNA
<213> ORGANISM: P. aeruginosa
<220> FEATURE:
<223> OTHER INFORMATION: Oligonucleotide

<400> SEQUENCE: 29
ttctgcagac ggccctctcg aggctggcgc tgcagtt                                37

<210> SEQ ID NO 30
<211> LENGTH: 37
<212> TYPE: DNA
<213> ORGANISM: P. aeruginosa
<220> FEATURE:
<223> OTHER INFORMATION: Oligonucleotide

<400> SEQUENCE: 30
aactgcagcg ccagcctcga gtcggccgtc tgcagaa                                37

<210> SEQ ID NO 31
<211> LENGTH: 37
<212> TYPE: DNA
<213> ORGANISM: P. aeruginosa
<220> FEATURE:
<223> OTHER INFORMATION: Oligonucleotide

<400> SEQUENCE: 31
ttctgcagac ggccgactcg aggctggcgc tgcagtt                                37

<210> SEQ ID NO 32
<211> LENGTH: 37
<212> TYPE: DNA
<213> ORGANISM: P. aeruginosa
<220> FEATURE:
<223> OTHER INFORMATION: Oligonucleotide

<400> SEQUENCE: 32
aactgcagcg ccagcctcga gcacgtcgtc tgcagaa                                37

<210> SEQ ID NO 33
<211> LENGTH: 37
<212> TYPE: DNA
<213> ORGANISM: P. aeruginosa
<220> FEATURE:
<223> OTHER INFORMATION: Oligonucleotide

<400> SEQUENCE: 33
ttctgcagac gacgtgctcg aggctggcgc tgcagtt                                37

<210> SEQ ID NO 34
<211> LENGTH: 1698
<212> TYPE: DNA
<213> ORGANISM: P. aeruginosa
<220> FEATURE:
<223> OTHER INFORMATION: Polynucleotide

<400> SEQUENCE: 34
```

```
atggccgaag aagctttcga cctctggaac gaatgcgcca agcctgcgt gctcgacctc        60 aaggacggcg tgcgttccag ccgcatgagc gtcgacccgg ccatcgccga caccaacggc       120
cagggcgtgc tgcactactc catggtcctg gagggcggca acgacgcgct caagctggcc       180
atcgacaacg ccctcagcat caccagcgac ggcctgacca tccgcctcga aggcggcgtc       240
gagccgaaca agccggtgcg ctacagctac acgcgccagg cgcgcggcag ttggtcgctg       300
aactggctgg taccgatcgg ccacgagaag ccctcgaaca tcaaggtgtt catccacgaa       360
ctgaacgccg gcaaccagct cagccacatg tcgccgatct acaccatcga gatgggcgac       420
gagttgctgg cgaagctggc gcgcgatgcc accttcttcg tcagggcgca cgagagcaac       480
gagatgcagc cgacgctcgc catcagccat gccggggtca gcgtggtcat ggcccagacc       540
cagccgcgcc gggaaaagcg ctggagcgaa tgggccagcg caaggtgtt gtgcctgctc        600 gacccgctgg acggggtcta caactacctc gcccagcaac gctgcaacct cgacgatacc       660
tgggaaggca agatctaccg ggtgctcgcc ggcaacccgg cgaagcatga cctggacatc       720
aaacccacgg tcatcagtca tcgcctgcac tttcccgagg gcggcagcct ggccgcgctg       780
accgcgcacc aggcttgcca cctgccgctg gagactttca cccgtcatcg ccagccgcgc       840
ggctgggaac aactcgagca gtgcggctat ccggtgcagc ggctggtcgc cctctacctg       900
gcggcgcggc tgtcgtggaa ccaggtcgac caggtgatcc gcaacgccct ggccagcccc       960
ggcagcggcg gcgacctggg cgaagcgatc cgcgagcagc cggagcaggc ccgtctggcc      1020
ctgaccctgg ccgccgccga gagcgagcgc ttcgtccggc agggcaccgg caacgacgag      1080
gccggcgcgg caaacctgca gggaggatta cgccagcctc gattcccgac catcccgctg      1140
tcccgtctgt tcgacaacgc tatgctgcgt gctcaccgtc tgcaccagct ggctttcgac      1200
acctaccagg agttcgaaga agcatacatc ccgaaagaac agaaatactc cttcctgcaa      1260
aacccgcaga cctccctgtg cttctccgaa tcgatcccga ccccgtccaa ccgtgaagaa      1320
acccagcaga aatccaacct ggagctcctg cgtatctccc tgctgctgat ccagtcctgg      1380
ctcgagccgg ttcagttcct gcgttccgtt ttcgctaact ccctggttta cggtgctagc      1440
gactccaacg tttacgacct gctgaaagac ctggaagaag gtatccagac cctgatgggt      1500
cgtctggaag acggttcccc gcgtaccggt cagatcttca acagacccta ctccaaattc      1560
gacaccaact cccacaacga cgacgctctg ctgaaaaact acggtctgct gtactgcttc      1620
cgtaaagaca tggacaaagt tgaaaccttc ctgcgtatcg ttcagtgccg ttccgttgaa      1680
ggttcctgcg gtttctaa                                                   1698
```

<210> SEQ ID NO 35
<211> LENGTH: 565
<212> TYPE: PRT
<213> ORGANISM: P. aeruginosa
<220> FEATURE:
<223> OTHER INFORMATION: Polypeptide

<400> SEQUENCE: 35

Met Ala Glu Glu Ala Phe Asp Leu Trp Asn Glu Cys Ala Lys Ala Cys
  1               5                  10                  15

Val Leu Asp Leu Lys Asp Gly Val Arg Ser Ser Arg Met Ser Val Asp
             20                  25                  30

Pro Ala Ile Ala Asp Thr Asn Gly Gln Gly Val Leu His Tyr Ser Met
         35                  40                  45

Val Leu Glu Gly Gly Asn Asp Ala Leu Lys Leu Ala Ile Asp Asn Ala
     50                  55                  60

-continued

```
Leu Ser Ile Thr Ser Asp Gly Leu Thr Ile Arg Leu Glu Gly Gly Val
 65                  70                  75                  80

Glu Pro Asn Lys Pro Val Arg Tyr Ser Tyr Thr Arg Gln Ala Arg Gly
                 85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Glu Ser Glu Arg Phe Val
            340                 345                 350

Arg Gln Gly Thr Gly Asn Asp Glu Ala Gly Ala Ala Asn Leu Gln Gly
        355                 360                 365

Gly Leu Arg Gln Pro Arg Phe Pro Thr Ile Pro Leu Ser Arg Leu Phe
370                 375                 380

Asp Asn Ala Met Leu Arg Ala His Arg Leu His Gln Leu Ala Phe Asp
385                 390                 395                 400

Thr Tyr Gln Glu Phe Glu Glu Ala Tyr Ile Pro Lys Glu Gln Lys Tyr
                405                 410                 415

Ser Phe Leu Gln Asn Pro Gln Thr Ser Leu Cys Phe Ser Glu Ser Ile
            420                 425                 430

Pro Thr Pro Ser Asn Arg Glu Glu Thr Gln Gln Lys Ser Asn Leu Glu
        435                 440                 445

Leu Leu Arg Ile Ser Leu Leu Leu Ile Gln Ser Trp Leu Glu Pro Val
450                 455                 460

Gln Phe Leu Arg Ser Val Phe Ala Asn Ser Leu Val Tyr Gly Ala Ser
465                 470                 475                 480
```

```
Asp Ser Asn Val Tyr Asp Leu Leu Lys Asp Leu Glu Glu Gly Ile Gln
            485                 490                 495
Thr Leu Met Gly Arg Leu Glu Asp Gly Ser Pro Arg Thr Gly Gln Ile
        500                 505                 510
Phe Lys Gln Thr Tyr Ser Lys Phe Asp Thr Asn Ser His Asn Asp Asp
        515                 520                 525
Ala Leu Leu Lys Asn Tyr Gly Leu Leu Tyr Cys Phe Arg Lys Asp Met
        530                 535                 540
Asp Lys Val Glu Thr Phe Leu Arg Ile Val Gln Cys Arg Ser Val Glu
545                 550                 555                 560
Gly Ser Cys Gly Phe
            565

<210> SEQ ID NO 36
<211> LENGTH: 1620
<212> TYPE: DNA
<213> ORGANISM: P. aeruginosa
<220> FEATURE:
<223> OTHER INFORMATION: Polynucleotide

<400> SEQUENCE: 36
atggccgaag aagctttcga cctctggaac gaatgcgcca aagcctgcgt gctcgacctc      60
aaggacggcg tgcgttccag ccgcatgagc gtcgacccgg ccatcgccga caccaacggc     120
cagggcgtgc tgcactactc catggtcctg gagggcggca cgacgcgct caagctggcc      180 atcgacaacg ccctcagcat caccagcgac ggcctgacca tccgcctcga aggcggcgtc     240
gagccgaaca agccggtgcg ctacagctac acgcgccagg cgcgcggcag ttggtcgctg     300
aactggctgg taccgatcgg ccacgagaag ccctcgaaca tcaaggtgtt catccacgaa     360
ctgaacgccg gcaaccagct cagccacatg tcgccgatct acaccatcga gatgggcgac     420
gagttgctgg cgaagctggc gcgcgatgcc accttcttcg tcagggcgca cgagagcaac     480
gagatgcagc cgacgctcgc catcagccat gccggggtca gcgtggtcat ggcccagacc     540
cagccgcgcc gggaaaagcg ctggagcgaa tgggccagcg gcaaggtgtt gtgcctgctc     600
gacccgctgg acggggtcta caactacctc gcccagcaac gctgcaacct cgacgatacc     660
tgggaaggca agatctaccg ggtgctcgcc ggcaacccgg cgaagcatga cctggacatc     720
aaacccacgg tcatcagtca tcgcctgcac tttcccgagg gcggcagcct ggccgcgctg     780
accgcgcacc aggcttgcca cctgccgctg gagactttca cccgtcatcg ccagccgcgc     840
ggctgggaac aactcgagca gtgcggctat ccggtgcagc ggctggtcgc cctctacctg     900
gcggcgcggc tgtcgtggaa ccaggtcgac caggtgatcc gcaacgccct ggccagcccc     960
ggcagcggcg cgaccctggg cgaagcgatc cgcgagcagc cggagcaggc ccgtctggcc    1020
ctgaccctgg ccgccgccga gagcgagcgc ttcgtccggc agggcaccgg caacgacgag    1080
gccgcgcgcg caaacctgca gggaggctta cgccagcctc gatgcgatct gcctcagacc    1140
cacagcctgg cagcaggag accctgatg ctgctggctc agatgaggag aatcagcctg      1200
tttagctgcc tgaaggatag gcacgatttt ggctttcctc aagaggagtt tggcaaccag    1260
tttcagaagg ctgagaccat ccctgtgctg cacgagatga tccagcagat ctttaacctg    1320
tttagcacca aggatagcag cgctgcttgg gatgagaccc tgctggataa gttttacacc    1380
gagctgtacc agcagctgaa cgatctggag gcttgcgtga tccagggcgt gggcgtgacc    1440
gagacccctc tgatgaagga ggatagcatc ctggctgtga ggaagtactt tcagaggatc    1500 acccctgtacc tgaaggagaa gaagtacagc ccctgcgctt gggaagtcgt gagggctgag    1560
```
atcatgagga gctttagcct gagcaccaac ctgcaagaga gcttgaggtc taaggagtaa    1620

<210> SEQ ID NO 37
<211> LENGTH: 539
<212> TYPE: PRT
<213> ORGANISM: P. aeruginosa
<220> FEATURE:
<223> OTHER INFORMATION: Polypeptide

<400> SEQUENCE: 37

```
Met Ala Glu Glu Ala Phe Asp Leu Trp Asn Glu Cys Ala Lys Ala Cys
 1               5                  10                  15

Val Leu Asp Leu Lys Asp Gly Val Arg Ser Ser Arg Met Ser Val Asp
                20                  25                  30

Pro Ala Ile Ala Asp Thr Asn Gly Gln Gly Val Leu His Tyr Ser Met
            35                  40                  45

Val Leu Glu Gly Gly Asn Asp Ala Leu Lys Leu Ala Ile Asp Asn Ala
        50                  55                  60

Leu Ser Ile Thr Ser Asp Gly Leu Thr Ile Arg Leu Glu Gly Gly Val
 65                 70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
    290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Ala Glu Ser Glu Arg Phe Val
            340                 345                 350
```

```
Arg Gln Gly Thr Gly Asn Asp Glu Ala Gly Ala Ala Asn Leu Gln Gly
            355                 360                 365

Gly Leu Arg Gln Pro Arg Cys Asp Leu Pro Gln Thr His Ser Leu Gly
        370                 375                 380

Ser Arg Arg Thr Leu Met Leu Ala Gln Met Arg Arg Ile Ser Leu
385                 390                 395                 400

Phe Ser Cys Leu Lys Asp Arg His Asp Phe Gly Phe Pro Gln Glu Glu
                405                 410                 415

Phe Gly Asn Gln Phe Gln Lys Ala Glu Thr Ile Pro Val Leu His Glu
            420                 425                 430

Met Ile Gln Gln Ile Phe Asn Leu Phe Ser Thr Lys Asp Ser Ser Ala
            435                 440                 445

Ala Trp Asp Glu Thr Leu Leu Asp Lys Phe Tyr Thr Glu Leu Tyr Gln
        450                 455                 460

Gln Leu Asn Asp Leu Glu Ala Cys Val Ile Gln Gly Val Gly Val Thr
465                 470                 475                 480

Glu Thr Pro Leu Met Lys Glu Asp Ser Ile Leu Ala Val Arg Lys Tyr
                485                 490                 495

Phe Gln Arg Ile Thr Leu Tyr Leu Lys Glu Lys Lys Tyr Ser Pro Cys
            500                 505                 510

Ala Trp Glu Val Val Arg Ala Glu Ile Met Arg Ser Phe Ser Leu Ser
        515                 520                 525

Thr Asn Leu Gln Glu Ser Leu Arg Ser Lys Glu
        530                 535

<210> SEQ ID NO 38
<211> LENGTH: 460
<212> TYPE: PRT
<213> ORGANISM: P. aeruginosa
<220> FEATURE:
<223> OTHER INFORMATION: Polypeptide

<400> SEQUENCE: 38

Met Ala Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Ser Met
        35                  40                  45

Val Leu Glu Gly Gly Asn Asp Ala Leu Lys Leu Ala Ile Asp Asn Ala
    50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175
```

```
Met Ala Gln Thr Gln Pro Arg Arg Glu Lys Arg Trp Ser Glu Trp Ala
                180                 185                 190

Ser Gly Lys Val Leu Cys Leu Leu Asp Pro Leu Asp Gly Val Tyr Asn
            195                 200                 205

Tyr Leu Ala Gln Gln Arg Cys Asn Leu Asp Asp Thr Trp Glu Gly Lys
        210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
        290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Ala Glu Ser Glu Arg Phe Val
            340                 345                 350

Arg Gln Gly Thr Gly Asn Asp Glu Ala Gly Ala Ala Asn Leu Gln Gly
        355                 360                 365

Gly Leu Arg Gln Pro Arg Phe Val Asn Gln His Leu Cys Gly Ser His
        370                 375                 380

Leu Val Glu Ala Leu Tyr Leu Val Cys Gly Glu Arg Gly Phe Phe Tyr
385                 390                 395                 400

Thr Pro Lys Thr Arg Arg Glu Ala Glu Asp Leu Gln Val Gly Gln Val
                405                 410                 415

Glu Leu Gly Gly Gly Pro Gly Ala Gly Ser Leu Gln Pro Leu Ala Leu
            420                 425                 430

Glu Gly Ser Leu Gln Lys Arg Gly Ile Val Glu Gln Cys Cys Thr Ser
        435                 440                 445

Ile Cys Ser Leu Tyr Gln Leu Glu Asn Tyr Cys Asn
    450                 455                 460

<210> SEQ ID NO 39
<211> LENGTH: 404
<212> TYPE: PRT
<213> ORGANISM: P. aeruginosa
<220> FEATURE:
<223> OTHER INFORMATION: Polypeptide

<400> SEQUENCE: 39

Met Ala Glu Glu Ala Phe Asp Leu Trp Asn Glu Cys Ala Lys Ala Cys
 1               5                  10                  15

Val Leu Asp Leu Lys Asp Gly Val Arg Ser Ser Arg Met Ser Val Asp
                20                  25                  30

Pro Ala Ile Ala Asp Thr Asn Gly Gln Gly Val Leu His Tyr Ser Met
            35                  40                  45

Val Leu Glu Gly Gly Asn Asp Ala Leu Lys Leu Ala Ile Asp Asn Ala
        50                  55                  60

Leu Ser Ile Thr Ser Asp Gly Leu Thr Ile Arg Leu Glu Gly Gly Val
65                  70                  75                  80
```

```
Glu Pro Asn Lys Pro Val Arg Tyr Ser Tyr Thr Arg Gln Ala Arg Gly
                85                  90                  95
Ser Trp Ser Leu Asn Trp Leu Val Pro Ile Gly His Glu Lys Pro Ser
            100                 105                 110
Asn Ile Lys Val Phe Ile His Glu Leu Asn Ala Gly Asn Gln Leu Ser
        115                 120                 125
His Met Ser Pro Ile Tyr Thr Ile Glu Met Gly Asp Glu Leu Leu Ala
    130                 135                 140
Lys Leu Ala Arg Asp Ala Thr Phe Phe Val Arg Ala His Glu Ser Asn
145                 150                 155                 160
Glu Met Gln Pro Thr Leu Ala Ile Ser His Ala Gly Val Ser Val Val
                165                 170                 175
Met Ala Gln Thr Gln Pro Arg Arg Glu Lys Arg Trp Ser Glu Trp Ala
            180                 185                 190
Ser Gly Lys Val Leu Cys Leu Leu Asp Pro Leu Asp Gly Val Tyr Asn
        195                 200                 205
Tyr Leu Ala Gln Gln Arg Cys Asn Leu Asp Asp Thr Trp Glu Gly Lys
    210                 215                 220
Ile Tyr Arg Val Leu Ala Gly Asn Pro Ala Lys His Asp Leu Asp Ile
225                 230                 235                 240
Lys Pro Thr Val Ile Ser His Arg Leu His Phe Pro Glu Gly Gly Ser
                245                 250                 255
Leu Ala Ala Leu Thr Ala His Gln Ala Cys His Leu Pro Leu Glu Thr
            260                 265                 270
Phe Thr Arg His Arg Gln Pro Arg Gly Trp Glu Gln Leu Glu Gln Cys
        275                 280                 285
Gly Tyr Pro Val Gln Arg Leu Val Ala Leu Tyr Leu Ala Ala Arg Leu
    290                 295                 300
Ser Trp Asn Gln Val Asp Gln Val Ile Arg Asn Ala Leu Ala Ser Pro
305                 310                 315                 320
Gly Ser Gly Gly Asp Leu Gly Glu Ala Ile Arg Glu Gln Pro Glu Gln
                325                 330                 335
Ala Arg Leu Ala Leu Thr Leu Ala Ala Glu Ser Glu Arg Phe Val
            340                 345                 350
Arg Gln Gly Thr Gly Asn Asp Glu Ala Gly Ala Ala Asn Leu Gln Gly
        355                 360                 365
Gly Leu Arg Gln Pro Arg Phe Val Asn Gln His Leu Cys Gly Ser His
    370                 375                 380
Leu Val Glu Ala Leu Tyr Leu Val Cys Gly Glu Arg Gly Phe Phe Tyr
385                 390                 395                 400
Thr Pro Lys Thr

<210> SEQ ID NO 40
<211> LENGTH: 21
<212> TYPE: PRT
<213> ORGANISM: P. aeruginosa
<220> FEATURE:
<223> OTHER INFORMATION: Polypeptide

<400> SEQUENCE: 40

Gly Ile Val Glu Gln Cys Cys Thr Ser Ile Cys Ser Leu Tyr Gln Leu
1               5                   10                  15

Glu Asn Tyr Cys Asn
            20
```

```
<210> SEQ ID NO 41
<211> LENGTH: 638
<212> TYPE: PRT
<213> ORGANISM: Pseudomonas Aeruginosa
<220> FEATURE:
<223> OTHER INFORMATION: P.Aeruginosa exotoxin A protein sequence

<400> SEQUENCE: 41
```

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
                20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
    115                 120                 125

Pro Ile Gly His Glu Lys Pro Ser Asn Ile Lys Val Phe Ile His Glu
130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
    195                 200                 205

Glu Lys Arg Trp Ser Glu Trp Ala Ser Gly Lys Val Leu Cys Leu Leu
210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
    275                 280                 285

Ala Cys His Leu Pro Leu Glu Thr Phe Thr Arg His Arg Gln Pro Arg
290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
    355                 360                 365

Ala Ala Glu Ser Glu Arg Phe Val Arg Gln Gly Thr Gly Asn Asp Glu

-continued

```
              370                 375                 380
Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Gly Asp Val
                420                 425                 430

Ser Phe Ser Thr Arg Gly Thr Gln Asn Trp Thr Val Glu Arg Leu Leu
                435                 440                 445

Gln Ala His Arg Gln Leu Glu Glu Arg Gly Tyr Val Phe Val Gly Tyr
450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
                500                 505                 510

Asp Ala Arg Gly Arg Ile Arg Asn Gly Ala Leu Leu Arg Val Tyr Val
                515                 520                 525

Pro Arg Ser Ser Leu Pro Gly Phe Tyr Arg Thr Ser Leu Thr Leu Ala
                530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Glu Gly Gly Arg
                565                 570                 575

Leu Glu Thr Ile Leu Gly Trp Pro Leu Ala Glu Arg Thr Val Val Ile
                580                 585                 590

Pro Ser Ala Ile Pro Thr Asp Pro Arg Asn Val Gly Gly Asp Leu Asp
                595                 600                 605

Pro Ser Ser Ile Pro Asp Lys Glu Gln Ala Ile Ser Ala Leu Pro Asp
                610                 615                 620

Tyr Ala Ser Gln Pro Gly Lys Pro Pro Arg Glu Asp Leu Lys
625                 630                 635
```